(12) United States Patent
Wieland et al.

(10) Patent No.: US 12,391,746 B2
(45) Date of Patent: Aug. 19, 2025

(54) HPV PROTEINS, ANTIBODIES, AND USES IN MANAGING ABNORMAL EPITHELIAL CELL GROWTH

(71) Applicant: Emory University, Atlanta, GA (US)

(72) Inventors: Andreas Wieland, Atlanta, GA (US); Rafi Ahmed, Atlanta, GA (US)

(73) Assignee: Emory University, Atlanta, GA (US)

( * ) Notice: Subject to any disclaimer, the term of this patent is extended or adjusted under 35 U.S.C. 154(b) by 1372 days.

(21) Appl. No.: 16/971,627

(22) PCT Filed: Feb. 20, 2019

(86) PCT No.: PCT/US2019/018798
§ 371 (c)(1),
(2) Date: Aug. 20, 2020

(87) PCT Pub. No.: WO2019/164970
PCT Pub. Date: Aug. 29, 2019

(65) Prior Publication Data
US 2020/0399348 A1    Dec. 24, 2020

Related U.S. Application Data

(60) Provisional application No. 62/632,777, filed on Feb. 20, 2018.

(51) Int. Cl.
| | |
|---|---|
| C07K 16/08 | (2006.01) |
| A61K 38/20 | (2006.01) |
| A61K 39/00 | (2006.01) |
| A61K 39/395 | (2006.01) |
| A61K 40/11 | (2025.01) |
| A61K 40/31 | (2025.01) |
| A61K 40/46 | (2025.01) |
| C12N 5/0783 | (2010.01) |

(52) U.S. Cl.
CPC ........ *C07K 16/084* (2013.01); *A61K 38/2013* (2013.01); *A61K 39/3955* (2013.01); *A61K 40/11* (2025.01); *A61K 40/31* (2025.01); *A61K 40/46* (2025.01); *C12N 5/0636* (2013.01); *C07K 2317/24* (2013.01); *C12N 2510/00* (2013.01)

(58) Field of Classification Search
CPC .............. C07K 16/084; C07K 2317/24; G01N 2333/025; A61K 40/46; A61K 39/12
See application file for complete search history.

(56) References Cited

U.S. PATENT DOCUMENTS

| 8,420,103 B2 | 4/2013 | Baudin |
| 2001/0034021 A1 | 10/2001 | Muller |
| 2004/0152074 A1 | 8/2004 | Muller |
| 2005/0226875 A1 | 10/2005 | Gomez-Navarro |
| 2009/0269732 A1 | 10/2009 | Ivey |
| 2009/0312527 A1 | 12/2009 | Cheng |
| 2010/0151466 A1 | 6/2010 | Schlegel |
| 2015/0153345 A1 | 6/2015 | Dixon |
| 2015/0218264 A1 | 8/2015 | Cattaneo |
| 2017/0007693 A1 | 1/2017 | Weiner |
| 2017/0028052 A1 | 2/2017 | Ramos |
| 2017/0247456 A1 | 8/2017 | Freeman |
| 2017/0281747 A1 | 10/2017 | Bunnik |

FOREIGN PATENT DOCUMENTS

| GB | 2379220 | 3/2003 |
| WO | 2015149051 | 10/2015 |

OTHER PUBLICATIONS

Liu et al (Fc-Engineering for Modulated Effector Functions-Improving Antibodies for Cancer Treatment. Antibodies (Basel). Nov. 17, 2020;9(4):64) (Year: 2020).*
Hezareh et al ( Effector function activities of a panel of mutants of a broadly neutralizing antibody against human immunodeficiency virus type 1. J Virol. Dec. 2001;75(24):12161-8) (Year: 2001).*
Rosales et al (Antibodies against human papillomavirus (HPV) type 16 and 18 E2, E6 and E7 proteins in sera: correlation with presence of papillomavirus DNA. J Med Virol. Dec. 2001;65(4):736-44) (Year: 2001).*
McCarthy et al. (J. Immunol. Methods, 251(1-2): 137-149, 2001) (Year: 2001).*
Lin et al. (African Journal of Biotechnology, 10(79):18294-18302, 2011) (Year: 2011).*
Bechtold et al. Human Papillomavirus Type 16 E2 Protein Has No. Effect on Transcription from Episomal Viral DNA, Journal of Virology, 2003, 77(3):2021-2028.
Eberhardt et al. Functional HPV-specific PD-1+ stem-like CD8 T cells in head and neck cancer, Nature, 2021, 597(7875):279-284.
Paolini et al. Human papillomavirus 16 E2 interacts with neuregulin receptor degradation protein 1 affecting ErbB-3 expression in vitro and in clinical samples of cervical lesions, European Journal of Cancer 58 (2016) 52-61.

(Continued)

*Primary Examiner* — Gregory S Emch
*Assistant Examiner* — Ashley H. Gao
(74) *Attorney, Agent, or Firm* — Emory Patent Group

(57) ABSTRACT

This disclosure relates to HPV proteins, antibodies, and uses in managing abnormal epithelial cell growth. In certain embodiments, this disclosure relates to detecting an HPV protein in a sample and correlating the presence as an indication that a subject is at risk of developing an HPV-related disease or condition. In certain embodiments, the HPV protein is E2 and/or E6. In certain embodiments, this disclosure relates to vaccinating or treating a subject for an HPV infection or related condition optionally in combination with immune-checkpoint inhibitors. In certain embodiments, this disclosure relates to HPV protein specific antibodies and binding agents for uses reported herein.

12 Claims, 4 Drawing Sheets
Specification includes a Sequence Listing.

(56) References Cited

OTHER PUBLICATIONS

Ruttkay-Nedecky et al. I Relevance of infection with human papillomavirus: The role of the p53 tumor suppressor protein and E6/E7 zinc finger proteins (Review), International Journal of Oncology 43: 1754-1762, 2013.
Thomas et al. Human papillomaviruses, cervical cancer and cell polarity, Oncogene, 2008, 27, 7018-7030.
Wieland et al. Defining HPV-specific B cell responses in patients with head and neck cancer, Nature, Sep. 2021;597(7875):274-278.

* cited by examiner

SEQUENCE LISTING

```
<160> NUMBER OF SEQ ID NOS: 179

<210> SEQ ID NO 1
<211> LENGTH: 365
<212> TYPE: PRT
<213> ORGANISM: Artificial
<220> FEATURE:
<223> OTHER INFORMATION: Synthetic construct

<400> SEQUENCE: 1

Met Glu Thr Leu Cys Gln Arg Leu Asn Val Cys Gln Asp Lys Ile Leu
1               5                   10                  15

Thr His Tyr Glu Asn Asp Ser Thr Asp Leu Arg Asp His Ile Asp Tyr
```

```
                  20                  25                  30
Trp Lys His Met Arg Leu Glu Cys Ala Ile Tyr Tyr Lys Ala Arg Glu
             35                  40                  45
Met Gly Phe Lys His Ile Asn His Gln Val Val Pro Thr Leu Ala Val
         50                  55                  60
Ser Lys Asn Lys Ala Leu Gln Ala Ile Glu Leu Gln Leu Thr Leu Glu
 65                  70                  75                  80
Thr Ile Tyr Asn Ser Gln Tyr Ser Asn Glu Lys Trp Thr Leu Gln Asp
                 85                  90                  95
Val Ser Leu Glu Val Tyr Leu Thr Ala Pro Thr Gly Cys Ile Lys Lys
            100                 105                 110
His Gly Tyr Thr Val Glu Val Gln Phe Asp Gly Asp Ile Cys Asn Thr
            115                 120                 125
Met His Tyr Thr Asn Trp Thr His Ile Tyr Ile Cys Glu Glu Ala Ser
            130                 135                 140
Val Thr Val Val Glu Gly Gln Val Asp Tyr Tyr Gly Leu Tyr Tyr Val
145                 150                 155                 160
His Glu Gly Ile Arg Thr Tyr Phe Val Gln Phe Lys Asp Asp Ala Glu
                165                 170                 175
Lys Tyr Ser Lys Asn Lys Val Trp Glu Val His Ala Gly Gly Gln Val
            180                 185                 190
Ile Leu Cys Pro Thr Ser Val Phe Ser Ser Asn Glu Val Ser Ser Pro
            195                 200                 205
Glu Ile Ile Arg Gln His Leu Ala Asn His Pro Ala Ala Thr His Thr
            210                 215                 220
Lys Ala Val Ala Leu Gly Thr Glu Glu Thr Gln Thr Thr Ile Gln Arg
225                 230                 235                 240
Pro Arg Ser Glu Pro Asp Thr Gly Asn Pro Cys His Thr Thr Lys Leu
                245                 250                 255
Leu His Arg Asp Ser Val Asp Ser Ala Pro Ile Leu Thr Ala Phe Asn
            260                 265                 270
Ser Ser His Lys Gly Arg Ile Asn Cys Asn Ser Asn Thr Thr Pro Ile
            275                 280                 285
Val His Leu Lys Gly Asp Ala Asn Thr Leu Lys Cys Leu Arg Tyr Arg
            290                 295                 300
Phe Lys Lys His Cys Thr Leu Tyr Thr Ala Val Ser Ser Thr Trp His
305                 310                 315                 320
Trp Thr Gly His Asn Val Lys His Lys Ser Ala Ile Val Thr Leu Thr
                325                 330                 335
Tyr Asp Ser Glu Trp Gln Arg Asp Gln Phe Leu Ser Gln Val Lys Ile
            340                 345                 350
Pro Lys Thr Ile Thr Val Ser Thr Gly Phe Met Ser Ile
            355                 360                 365

<210> SEQ ID NO 2
<211> LENGTH: 18
<212> TYPE: PRT
<213> ORGANISM: Artificial
<220> FEATURE:
<223> OTHER INFORMATION: Synthetic construct

<400> SEQUENCE: 2

Asp Lys Ile Leu Thr His Tyr Glu Asn Asp Ser Thr Asp Leu Arg Asp
 1               5                  10                  15

His Ile
```

```
<210> SEQ ID NO 3
<211> LENGTH: 11
<212> TYPE: PRT
<213> ORGANISM: Artificial
<220> FEATURE:
<223> OTHER INFORMATION: Synthetic construct

<400> SEQUENCE: 3

Asp Leu Arg Asp His Ile Asp Tyr Trp Lys His
1               5                   10

<210> SEQ ID NO 4
<211> LENGTH: 23
<212> TYPE: PRT
<213> ORGANISM: Artificial
<220> FEATURE:
<223> OTHER INFORMATION: Synthetic construct

<400> SEQUENCE: 4

Ala Ile Tyr Tyr Lys Ala Arg Glu Met Gly Phe Lys His Ile Asn His
1               5                   10                  15

Gln Val Val Pro Thr Leu Ala
            20

<210> SEQ ID NO 5
<211> LENGTH: 29
<212> TYPE: PRT
<213> ORGANISM: Artificial
<220> FEATURE:
<223> OTHER INFORMATION: Synthetic construct

<400> SEQUENCE: 5

Ala Ile Tyr Tyr Lys Ala Arg Glu Met Gly Phe Lys His Ile Asn His
1               5                   10                  15

Gln Val Val Pro Thr Leu Ala Val Ser Lys Lys Ala Leu
            20                  25

<210> SEQ ID NO 6
<211> LENGTH: 25
<212> TYPE: PRT
<213> ORGANISM: Artificial
<220> FEATURE:
<223> OTHER INFORMATION: Synthetic construct

<400> SEQUENCE: 6

Tyr Tyr Lys Ala Arg Glu Met Gly Phe Lys His Ile Asn His Gln Val
1               5                   10                  15

Val Pro Thr Leu Ala Val Ser Lys Asn
            20                  25

<210> SEQ ID NO 7
<211> LENGTH: 20
<212> TYPE: PRT
<213> ORGANISM: Artificial
<220> FEATURE:
<223> OTHER INFORMATION: Synthetic construct

<400> SEQUENCE: 7

Ile Asn His Gln Val Val Pro Thr Leu Ala Val Ser Lys Asn Lys Ala
1               5                   10                  15

Leu Gln Ala Ile
            20
```

```
<210> SEQ ID NO 8
<211> LENGTH: 17
<212> TYPE: PRT
<213> ORGANISM: Artificial
<220> FEATURE:
<223> OTHER INFORMATION: Synthetic construct

<400> SEQUENCE: 8

Ile Asn His Gln Val Val Pro Thr Leu Ala Val Ser Lys Asn Lys Ala
1               5                   10                  15

Leu

<210> SEQ ID NO 9
<211> LENGTH: 37
<212> TYPE: PRT
<213> ORGANISM: Artificial
<220> FEATURE:
<223> OTHER INFORMATION: Synthetic construct

<400> SEQUENCE: 9

Thr Leu Ala Val Ser Lys Asn Lys Ala Leu Gln Ala Ile Glu Leu Gln
1               5                   10                  15

Leu Thr Leu Glu Thr Ile Tyr Asn Ser Gln Tyr Ser Asn Glu Lys Trp
            20                  25                  30

Thr Leu Gln Asp Val
        35

<210> SEQ ID NO 10
<211> LENGTH: 25
<212> TYPE: PRT
<213> ORGANISM: Artificial
<220> FEATURE:
<223> OTHER INFORMATION: Synthetic construct

<400> SEQUENCE: 10

Gln Leu Thr Leu Glu Thr Ile Tyr Asn Ser Gln Tyr Ser Asn Glu Lys
1               5                   10                  15

Trp Thr Leu Gln Asp Val Ser Leu Glu
            20                  25

<210> SEQ ID NO 11
<211> LENGTH: 14
<212> TYPE: PRT
<213> ORGANISM: Artificial
<220> FEATURE:
<223> OTHER INFORMATION: Synthetic construct

<400> SEQUENCE: 11

Thr Leu Glu Thr Ile Tyr Asn Ser Gln Tyr Ser Asn Glu Lys
1               5                   10

<210> SEQ ID NO 12
<211> LENGTH: 15
<212> TYPE: PRT
<213> ORGANISM: Artificial
<220> FEATURE:
<223> OTHER INFORMATION: Synthetic construct

<400> SEQUENCE: 12

Thr Ser Val Phe Ser Ser Asn Glu Val Ser Ser Pro Glu Ile Ile
1               5                   10                  15

<210> SEQ ID NO 13
<211> LENGTH: 36
<212> TYPE: PRT
```

<213> ORGANISM: Artificial
<220> FEATURE:
<223> OTHER INFORMATION: Synthetic construct

<400> SEQUENCE: 13

Val Phe Ser Ser Asn Glu Val Ser Pro Glu Ile Ile Arg Gln His
1               5                   10                  15

Leu Ala Asn His Pro Ala Ala Thr His Thr Lys Ala Val Ala Leu Gly
            20                  25                  30

Thr Glu Glu Thr
        35

<210> SEQ ID NO 14
<211> LENGTH: 37
<212> TYPE: PRT
<213> ORGANISM: Artificial
<220> FEATURE:
<223> OTHER INFORMATION: Synthetic construct

<400> SEQUENCE: 14

Glu Ile Ile Arg Gln His Leu Ala Asn His Pro Ala Ala Thr His Thr
1               5                   10                  15

Lys Ala Val Ala Leu Gly Thr Glu Glu Thr Gln Thr Thr Ile Gln Arg
            20                  25                  30

Pro Arg Ser Glu Pro
        35

<210> SEQ ID NO 15
<211> LENGTH: 158
<212> TYPE: PRT
<213> ORGANISM: Artificial
<220> FEATURE:
<223> OTHER INFORMATION: Synthetic construct

<400> SEQUENCE: 15

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu
145                 150                 155

<210> SEQ ID NO 16
<211> LENGTH: 18
<212> TYPE: PRT
<213> ORGANISM: Artificial

```
<220> FEATURE:
<223> OTHER INFORMATION: Synthetic construct

<400> SEQUENCE: 16

Met His Gln Lys Arg Thr Ala Met Phe Gln Asp Pro Gln Glu Arg Pro
1               5                   10                  15
Arg Lys

<210> SEQ ID NO 17
<211> LENGTH: 19
<212> TYPE: PRT
<213> ORGANISM: Artificial
<220> FEATURE:
<223> OTHER INFORMATION: Synthetic construct

<400> SEQUENCE: 17

Leu Pro Gln Leu Cys Thr Glu Leu Gln Thr Thr Ile His Asp Ile Ile
1               5                   10                  15
Leu Glu Cys

<210> SEQ ID NO 18
<211> LENGTH: 14
<212> TYPE: PRT
<213> ORGANISM: Artificial
<220> FEATURE:
<223> OTHER INFORMATION: Synthetic construct

<400> SEQUENCE: 18

Val Tyr Cys Lys Gln Gln Leu Leu Arg Arg Glu Val Tyr Asp
1               5                   10

<210> SEQ ID NO 19
<211> LENGTH: 17
<212> TYPE: PRT
<213> ORGANISM: Artificial
<220> FEATURE:
<223> OTHER INFORMATION: Synthetic construct

<400> SEQUENCE: 19

Phe Ala Phe Arg Asp Leu Cys Ile Val Tyr Arg Asp Gly Asn Pro Tyr
1               5                   10                  15
Ala

<210> SEQ ID NO 20
<211> LENGTH: 18
<212> TYPE: PRT
<213> ORGANISM: Artificial
<220> FEATURE:
<223> OTHER INFORMATION: Synthetic construct

<400> SEQUENCE: 20

Val Cys Asp Lys Cys Leu Lys Phe Tyr Ser Lys Ile Ser Glu Tyr Arg
1               5                   10                  15
His Tyr

<210> SEQ ID NO 21
<211> LENGTH: 15
<212> TYPE: PRT
<213> ORGANISM: Artificial
<220> FEATURE:
<223> OTHER INFORMATION: Synthetic construct

<400> SEQUENCE: 21

Cys Tyr Ser Leu Tyr Gly Thr Thr Leu Glu Gln Gln Tyr Asn Lys
```

<210> SEQ ID NO 22
<211> LENGTH: 16
<212> TYPE: PRT
<213> ORGANISM: Artificial
<220> FEATURE:
<223> OTHER INFORMATION: Synthetic construct

<400> SEQUENCE: 22

Pro Leu Cys Asp Leu Leu Ile Arg Cys Ile Asn Cys Gln Lys Pro Leu
1               5                   10                  15

<210> SEQ ID NO 23
<211> LENGTH: 15
<212> TYPE: PRT
<213> ORGANISM: Artificial
<220> FEATURE:
<223> OTHER INFORMATION: Synthetic construct

<400> SEQUENCE: 23

Cys Pro Glu Glu Lys Gln Arg His Leu Asp Lys Lys Gln Arg Phe
1               5                   10                  15

<210> SEQ ID NO 24
<211> LENGTH: 13
<212> TYPE: PRT
<213> ORGANISM: Artificial
<220> FEATURE:
<223> OTHER INFORMATION: Synthetic construct

<400> SEQUENCE: 24

His Asn Ile Arg Gly Arg Trp Thr Gly Arg Cys Met Ser
1               5                   10

<210> SEQ ID NO 25
<211> LENGTH: 13
<212> TYPE: PRT
<213> ORGANISM: Artificial
<220> FEATURE:
<223> OTHER INFORMATION: Synthetic construct

<400> SEQUENCE: 25

Cys Cys Arg Ser Ser Arg Thr Arg Arg Glu Thr Gln Leu
1               5                   10

<210> SEQ ID NO 26
<211> LENGTH: 435
<212> TYPE: DNA
<213> ORGANISM: Artificial
<220> FEATURE:
<223> OTHER INFORMATION: Synthetic construct

<400> SEQUENCE: 26
atggactgga cctggaggat cctcttcttg gtggcagcag caacaggtgt ccactcccag      60
gtgcagctgg tgcaatctgg gtctgagttg aggaagcctg ggcctcagt dacggtttcc     120 tgcaaggcct ctggatacac cttcagtaac catgatatga gttgggtgcg acaggcccct     180
ggacaaggac ttgagtggat gggatggatc aacagcaaca ctgggaaccc gacatatgcc     240
cagggcttca caggacggtt tgtcttctcc ttggacacct ctgtcagcac ggcatatctg     300
cagatcagta gtctgaagtc tgaggacact gccgtctatt actgtgcgaa agggggggggg     360 atctgtagtg gtagtagatg ttattccgga tggtttgaca gttggggcaa gggaaccctg     420
gtcgccgtct cctca                                                    435

```
<210> SEQ ID NO 27
<211> LENGTH: 145
<212> TYPE: PRT
<213> ORGANISM: Artificial
<220> FEATURE:
<223> OTHER INFORMATION: Synthetic construct

<400> SEQUENCE: 27

Met Asp Trp Thr Trp Arg Ile Leu Phe Leu Val Ala Ala Thr Gly
1               5                   10                  15

Val His Ser Gln Val Gln Leu Val Gln Ser Gly Ser Glu Leu Arg Lys
            20                  25                  30

Pro Gly Ala Ser Val Thr Val Ser Cys Lys Ala Ser Gly Tyr Thr Phe
        35                  40                  45

Ser Asn His Asp Met Ser Trp Val Arg Gln Ala Pro Gly Gln Gly Leu
    50                  55                  60

Glu Trp Met Gly Trp Ile Asn Ser Asn Thr Gly Asn Pro Thr Tyr Ala
65                  70                  75                  80

Gln Gly Phe Thr Gly Arg Phe Val Phe Ser Leu Asp Thr Ser Val Ser
                85                  90                  95

Thr Ala Tyr Leu Gln Ile Ser Ser Leu Lys Ser Glu Asp Thr Ala Val
            100                 105                 110

Tyr Tyr Cys Ala Lys Gly Gly Gly Ile Cys Ser Gly Ser Arg Cys Tyr
        115                 120                 125

Ser Gly Trp Phe Asp Ser Trp Gly Lys Gly Thr Leu Val Ala Val Ser
    130                 135                 140

Ser
145

<210> SEQ ID NO 28
<211> LENGTH: 8
<212> TYPE: PRT
<213> ORGANISM: Artificial
<220> FEATURE:
<223> OTHER INFORMATION: Synthetic construct

<400> SEQUENCE: 28

Gly Tyr Thr Phe Ser Asn His Asp
1               5

<210> SEQ ID NO 29
<211> LENGTH: 8
<212> TYPE: PRT
<213> ORGANISM: Artificial
<220> FEATURE:
<223> OTHER INFORMATION: Synthetic construct

<400> SEQUENCE: 29

Ile Asn Ser Asn Thr Gly Asn Pro
1               5

<210> SEQ ID NO 30
<211> LENGTH: 19
<212> TYPE: PRT
<213> ORGANISM: Artificial
<220> FEATURE:
<223> OTHER INFORMATION: Synthetic construct

<400> SEQUENCE: 30

Ala Lys Gly Gly Gly Ile Cys Ser Gly Ser Arg Cys Tyr Ser Gly Trp
1               5                   10                  15
```

Phe Asp Ser

<210> SEQ ID NO 31
<211> LENGTH: 396
<212> TYPE: DNA
<213> ORGANISM: Artificial
<220> FEATURE:
<223> OTHER INFORMATION: Synthetic construct

<400> SEQUENCE: 31

```
atggcttgga ccccactcct cttcctcacc ctcctcctcc actgcacagg gtctctctcc    60
cagcttgtgc tgactcaatc gccctctgcc tctgcctccc tgggagcctc ggtcaaactc   120
acctgcactc tgagcagtgg gcacagcggc tacgccatcg catggcatca gcagcagccg   180
gagaagggcc ctcggtactt gatgaagctt aacagtgatg gcacccacac caaggggac   240
gggatccctg atcgcttctc aggctccagc tctggggctg agcgctacct caccatctcc   300
agcctccagt ctgaggatga ggctgactat tactgtcaga cctggggcac tggcattcaa   360
gtcttcggaa ctgggaccaa ggtcaccatc ctaggt                             396
```

<210> SEQ ID NO 32
<211> LENGTH: 132
<212> TYPE: PRT
<213> ORGANISM: Artificial
<220> FEATURE:
<223> OTHER INFORMATION: Synthetic construct

<400> SEQUENCE: 32

```
Met Ala Trp Thr Pro Leu Leu Phe Leu Thr Leu Leu Leu His Cys Thr
1               5                   10                  15

Gly Ser Leu Ser Gln Leu Val Leu Thr Gln Ser Pro Ser Ala Ser Ala
            20                  25                  30

Ser Leu Gly Ala Ser Val Lys Leu Thr Cys Thr Leu Ser Ser Gly His
        35                  40                  45

Ser Gly Tyr Ala Ile Ala Trp His Gln Gln Gln Pro Glu Lys Gly Pro
    50                  55                  60

Arg Tyr Leu Met Lys Leu Asn Ser Asp Gly Thr His Thr Lys Gly Asp
65                  70                  75                  80

Gly Ile Pro Asp Arg Phe Ser Gly Ser Ser Ser Gly Ala Glu Arg Tyr
                85                  90                  95

Leu Thr Ile Ser Ser Leu Gln Ser Glu Asp Glu Ala Asp Tyr Tyr Cys
            100                 105                 110

Gln Thr Trp Gly Thr Gly Ile Gln Val Phe Gly Thr Gly Thr Lys Val
        115                 120                 125

Thr Ile Leu Gly
    130
```

<210> SEQ ID NO 33
<211> LENGTH: 7
<212> TYPE: PRT
<213> ORGANISM: Artificial
<220> FEATURE:
<223> OTHER INFORMATION: Synthetic construct

<400> SEQUENCE: 33

```
Ser Gly His Ser Gly Tyr Ala
1               5
```

<210> SEQ ID NO 34

```
<211> LENGTH: 7
<212> TYPE: PRT
<213> ORGANISM: Artificial
<220> FEATURE:
<223> OTHER INFORMATION: Synthetic construct

<400> SEQUENCE: 34

Leu Asn Ser Asp Gly Thr His
1               5

<210> SEQ ID NO 35
<211> LENGTH: 9
<212> TYPE: PRT
<213> ORGANISM: Artificial
<220> FEATURE:
<223> OTHER INFORMATION: Synthetic construct

<400> SEQUENCE: 35

Gln Thr Trp Gly Thr Gly Ile Gln Val
1               5

<210> SEQ ID NO 36
<211> LENGTH: 138
<212> TYPE: PRT
<213> ORGANISM: Artificial
<220> FEATURE:
<223> OTHER INFORMATION: Synthetic construct

<400> SEQUENCE: 36

Met Asp Trp Thr Trp Arg Ile Leu Phe Leu Val Ala Ala Ala Thr Gly
1               5                   10                  15

Val His Ser Gln Val Gln Leu Val Gln Ser Gly Ala Glu Val Thr Lys
            20                  25                  30

Pro Gly Ala Ser Val Lys Val Ser Cys Lys Ala Ser Gly Tyr Thr Phe
        35                  40                  45

Thr Glu Tyr Tyr Met His Trp Val Arg Gln Ala Pro Gly Gln Gly Leu
    50                  55                  60

Glu Trp Met Gly Arg Ile Asn Pro Asn Ser Gly Gly Thr Lys Tyr Ala
65                  70                  75                  80

Gln Lys Phe Gln Gly Arg Val Thr Met Thr Arg Asp Thr Thr Ile Ser
                85                  90                  95

Thr Val Tyr Met Glu Leu Thr Ser Ala Leu Ser Asp Asp Thr Ala Val
            100                 105                 110

Tyr Ser Cys Val Arg Ala Asp Asn Asn Gly Tyr Thr Tyr Thr Tyr Trp
        115                 120                 125

Gly Gln Gly Thr Leu Val Thr Val Ser Ser
    130                 135

<210> SEQ ID NO 37
<211> LENGTH: 8
<212> TYPE: PRT
<213> ORGANISM: Artificial
<220> FEATURE:
<223> OTHER INFORMATION: Synthetic construct

<400> SEQUENCE: 37

Gly Tyr Thr Phe Thr Glu Tyr Tyr
1               5

<210> SEQ ID NO 38
<211> LENGTH: 8
<212> TYPE: PRT
<213> ORGANISM: Artificial
```

<220> FEATURE:
<223> OTHER INFORMATION: Synthetic construct

<400> SEQUENCE: 38

Ile Asn Pro Asn Ser Gly Gly Thr
1               5

<210> SEQ ID NO 39
<211> LENGTH: 12
<212> TYPE: PRT
<213> ORGANISM: Artificial
<220> FEATURE:
<223> OTHER INFORMATION: Synthetic construct

<400> SEQUENCE: 39

Val Arg Ala Asp Asn Asn Gly Tyr Thr Tyr Thr Tyr
1               5                   10

<210> SEQ ID NO 40
<211> LENGTH: 393
<212> TYPE: DNA
<213> ORGANISM: Artificial
<220> FEATURE:
<223> OTHER INFORMATION: Synthetic construct

<400> SEQUENCE: 40

```
atggaagccc cagctcagct tctcttcctc ctgctactct ggctcccaga tatcaccgga    60
gaaattgtgt tgacacagtc tccagccacc ctgtctttgt ctcctgggga agagccacc   120
ctctcctgtc gggccagtca gagtgttagc agctacttag cctggtacca acagaaacct   180
ggccaggctc ccaggctcct catttatgat gcatctaaga gggccactgg catcccagcc   240
aggttcagtg gcagtgggtc tgggacagac ttcactctca ccatcagcag cctagagcct   300
gaagattttg cagtttattt ctgtcagctg cgtagcaact ggcctccgca cgagagggtc   360
actttcggcc ctgggaccaa agtggatttc aaa                                393
```

<210> SEQ ID NO 41
<211> LENGTH: 131
<212> TYPE: PRT
<213> ORGANISM: Artificial
<220> FEATURE:
<223> OTHER INFORMATION: Synthetic construct

<400> SEQUENCE: 41

Met Glu Ala Pro Ala Gln Leu Leu Phe Leu Leu Leu Trp Leu Pro
1               5                   10                  15

Asp Ile Thr Gly Glu Ile Val Leu Thr Gln Ser Pro Ala Thr Leu Ser
                20                  25                  30

Leu Ser Pro Gly Glu Arg Ala Thr Leu Ser Cys Arg Ala Ser Gln Ser
            35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Lys Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Phe Cys Gln Leu Arg Ser
            100                 105                 110

Asn Trp Pro Pro His Glu Arg Val Thr Phe Gly Pro Gly Thr Lys Val
        115                 120                 125

```
<210> SEQ ID NO 42
<211> LENGTH: 6
<212> TYPE: PRT
<213> ORGANISM: Artificial
<220> FEATURE:
<223> OTHER INFORMATION: Synthetic construct

<400> SEQUENCE: 42

Gln Ser Val Ser Ser Tyr
1               5

<210> SEQ ID NO 43
<211> LENGTH: 4
<212> TYPE: PRT
<213> ORGANISM: Artificial
<220> FEATURE:
<223> OTHER INFORMATION: Synthetic construct

<400> SEQUENCE: 43

Asp Ala Ser Lys
1

<210> SEQ ID NO 44
<211> LENGTH: 10
<212> TYPE: PRT
<213> ORGANISM: Artificial
<220> FEATURE:
<223> OTHER INFORMATION: Synthetic construct

<400> SEQUENCE: 44

Gln Leu Arg Ser Asn Trp Pro Pro His Glu
1               5                   10

<210> SEQ ID NO 45
<211> LENGTH: 408
<212> TYPE: DNA
<213> ORGANISM: Artificial
<220> FEATURE:
<223> OTHER INFORMATION: Synthetic construct

<400> SEQUENCE: 45
atggactgga cctggaggat cctcttcttg gtggcagcag ccacaggagc ccactcccag    60
gtgcagctgg tgcagtctgg gactgaggtg aaaaagcctg ggcctcagt gagggtctcc    120 tgcaaggctt ctggatacac cttcaccgag tactatttgc actgggtgcg acaggcccca   180
ggacaaggcc ttgagtggat gggacggatc aaccctaaca gtggcaacac aaactatgca   240
cagaaattta cggaagggt caccatgacc agtgatacgt ccgtcaattt agcctatttg    300
gaggtgagcg gctgacatc tgacgacacg gccatatatt attgtacgag agacgatagt   360
ggggctttcg tttactgggg ccagggaacc ctggtcaccg tctcttca              408

<210> SEQ ID NO 46
<211> LENGTH: 136
<212> TYPE: PRT
<213> ORGANISM: Artificial
<220> FEATURE:
<223> OTHER INFORMATION: Synthetic construct

<400> SEQUENCE: 46

Met Asp Trp Thr Trp Arg Ile Leu Phe Leu Val Ala Ala Ala Thr Gly
1               5                   10                  15
```

Ala His Ser Gln Val Gln Leu Val Gln Ser Gly Thr Glu Val Lys Lys
            20                  25                  30

Pro Gly Ala Ser Val Arg Val Ser Cys Lys Ala Ser Gly Tyr Thr Phe
        35                  40                  45

Thr Glu Tyr Tyr Leu His Trp Val Arg Gln Ala Pro Gly Gln Gly Leu
    50                  55                  60

Glu Trp Met Gly Arg Ile Asn Pro Asn Ser Gly Asn Thr Asn Tyr Ala
65                  70                  75                  80

Gln Lys Phe Asn Gly Arg Val Thr Met Thr Ser Asp Thr Ser Val Asn
                85                  90                  95

Leu Ala Tyr Leu Glu Val Ser Gly Leu Thr Ser Asp Asp Thr Ala Ile
            100                 105                 110

Tyr Tyr Cys Thr Arg Asp Asp Ser Gly Ala Phe Val Tyr Trp Gly Gln
        115                 120                 125

Gly Thr Leu Val Thr Val Ser Ser
    130                 135

<210> SEQ ID NO 47
<211> LENGTH: 13
<212> TYPE: PRT
<213> ORGANISM: Artificial
<220> FEATURE:
<223> OTHER INFORMATION: Synthetic construct

<400> SEQUENCE: 47

Gln Gln Arg Ile Asn Trp Pro Pro Arg Glu Lys Ile Thr
1               5                   10

<210> SEQ ID NO 48
<211> LENGTH: 8
<212> TYPE: PRT
<213> ORGANISM: Artificial
<220> FEATURE:
<223> OTHER INFORMATION: Synthetic construct

<400> SEQUENCE: 48

Ile Asn Pro Asn Ser Gly Asn Thr
1               5

<210> SEQ ID NO 49
<211> LENGTH: 10
<212> TYPE: PRT
<213> ORGANISM: Artificial
<220> FEATURE:
<223> OTHER INFORMATION: Synthetic construct

<400> SEQUENCE: 49

Thr Arg Asp Asp Ser Gly Ala Phe Val Tyr
1               5                   10

<210> SEQ ID NO 50
<211> LENGTH: 399
<212> TYPE: DNA
<213> ORGANISM: Artificial
<220> FEATURE:
<223> OTHER INFORMATION: Synthetic construct

<400> SEQUENCE: 50
atggaagccc cagctcagct tctcttcctc ctgctactct gcctcccagt tcagagacc      60 accggagaga ctgtgttgac acagtctcca gccaccctgt ctttgtctcc aggagaaaga    120
gccaccctct cctgcaggtc cagtcaggtt atcagcagct acttagcctg gttccaacaa    180

```
aaacctggcc aggctcccag gctcctcatc tatgatacat ccaacagggc cactggcatc    240
ccagccaggt tcagtggcag tgggtctggg acagacttca ctctcaccat cagtagccta    300
gagcctgagg attttgccgt ttattactgt cagcagcgta ccaactggcc tccgcgcgag    360
aaaatcactt tcggccctgg gaccaaagtg gatatcaag                           399
```

```
<210> SEQ ID NO 51
<211> LENGTH: 133
<212> TYPE: PRT
<213> ORGANISM: Artificial
<220> FEATURE:
<223> OTHER INFORMATION: Synthetic construct

<400> SEQUENCE: 51

Met Glu Ala Pro Ala Gln Leu Leu Phe Leu Leu Leu Leu Cys Leu Pro
1               5                   10                  15

Val Ser Glu Thr Thr Gly Glu Thr Val Leu Thr Gln Ser Pro Ala Thr
            20                  25                  30

Leu Ser Leu Ser Pro Gly Glu Arg Ala Thr Leu Ser Cys Arg Ser Ser
        35                  40                  45

Gln Val Ile Ser Ser Tyr Leu Ala Trp Phe Gln Gln Lys Pro Gly Gln
    50                  55                  60

Ala Pro Arg Leu Leu Ile Tyr Asp Thr Ser Asn Arg Ala Thr Gly Ile
65                  70                  75                  80

Pro Ala Arg Phe Ser Gly Ser Gly Ser Gly Thr Asp Phe Thr Leu Thr
                85                  90                  95

Ile Ser Ser Leu Glu Pro Glu Asp Phe Ala Val Tyr Tyr Cys Gln Gln
            100                 105                 110

Arg Thr Asn Trp Pro Pro Arg Glu Lys Ile Thr Phe Gly Pro Gly Thr
        115                 120                 125

Lys Val Asp Ile Lys
    130
```

```
<210> SEQ ID NO 52
<211> LENGTH: 6
<212> TYPE: PRT
<213> ORGANISM: Artificial
<220> FEATURE:
<223> OTHER INFORMATION: Synthetic construct

<400> SEQUENCE: 52

Gln Val Ile Ser Ser Tyr
1               5
```

```
<210> SEQ ID NO 53
<211> LENGTH: 4
<212> TYPE: PRT
<213> ORGANISM: Artificial
<220> FEATURE:
<223> OTHER INFORMATION: Synthetic construct

<400> SEQUENCE: 53

Asp Thr Ser Asn
1
```

```
<210> SEQ ID NO 54
<211> LENGTH: 13
<212> TYPE: PRT
<213> ORGANISM: Artificial
<220> FEATURE:
<223> OTHER INFORMATION: Synthetic construct
```

<400> SEQUENCE: 54

Gln Gln Arg Thr Asn Trp Pro Pro Arg Glu Lys Ile Thr
1               5                   10

<210> SEQ ID NO 55
<211> LENGTH: 447
<212> TYPE: DNA
<213> ORGANISM: Artificial
<220> FEATURE:
<223> OTHER INFORMATION: Synthetic construct

<400> SEQUENCE: 55

```
atggtgatca ggactgaaca gagagaactc accatggagt ttgggctgaa ctggcttttt      60
cttgtggcta tttaaaagg agtccagtgt gaggcgcagt tgttccagtc tggggggggc     120
ttggtccagc cggggggggtc cctgagactc acctgtgcaa cctctggctt caccttcacg     180
aattatgccc taagctgggt ccgccaggct ccagggaggg ggctggagtg ggtctcttct     240
attaccgata cgctgatgc acatactac gcagactccg tgaggggccg cttcaccatc     300
tccagagaca tcccaaaaa caccctatat ctgcagatgg acagcctaac agcccacgac     360
acggccattt atttctgtgc gaaacaccac cacagagacg atgcttttga tgtctggggc     420
caagggacaa tgatcaccgt ctcttca                                         447
```

<210> SEQ ID NO 56
<211> LENGTH: 149
<212> TYPE: PRT
<213> ORGANISM: Artificial
<220> FEATURE:
<223> OTHER INFORMATION: Synthetic construct

<400> SEQUENCE: 56

Met Val Ile Arg Thr Glu Gln Arg Glu Leu Thr Met Glu Phe Gly Leu
1               5                   10                  15

Asn Trp Leu Phe Leu Val Ala Ile Leu Lys Gly Val Gln Cys Glu Ala
                20                  25                  30

Gln Leu Phe Gln Ser Gly Gly Gly Leu Val Gln Pro Gly Gly Ser Leu
            35                  40                  45

Arg Leu Thr Cys Ala Thr Ser Gly Phe Thr Phe Thr Asn Tyr Ala Leu
        50                  55                  60

Ser Trp Val Arg Gln Ala Pro Gly Arg Gly Leu Glu Trp Val Ser Ser
65                  70                  75                  80

Ile Thr Asp Asn Ala Asp Ala Thr Tyr Tyr Ala Asp Ser Val Arg Gly
                85                  90                  95

Arg Phe Thr Ile Ser Arg Asp Asn Pro Lys Asn Thr Leu Tyr Leu Gln
            100                 105                 110

Met Asp Ser Leu Thr Ala His Asp Thr Ala Ile Tyr Phe Cys Ala Lys
        115                 120                 125

His His His Arg Asp Asp Ala Phe Asp Val Trp Gly Gln Gly Thr Met
    130                 135                 140

Ile Thr Val Ser Ser
145

<210> SEQ ID NO 57
<211> LENGTH: 8
<212> TYPE: PRT
<213> ORGANISM: Artificial
<220> FEATURE:
<223> OTHER INFORMATION: Synthetic construct

<400> SEQUENCE: 57

Gly Phe Thr Phe Thr Asn Tyr Ala
1               5

<210> SEQ ID NO 58
<211> LENGTH: 8
<212> TYPE: PRT
<213> ORGANISM: Artificial
<220> FEATURE:
<223> OTHER INFORMATION: Synthetic construct

<400> SEQUENCE: 58

Ile Thr Asp Asn Ala Asp Ala Thr
1               5

<210> SEQ ID NO 59
<211> LENGTH: 12
<212> TYPE: PRT
<213> ORGANISM: Artificial
<220> FEATURE:
<223> OTHER INFORMATION: Synthetic construct

<400> SEQUENCE: 59

Ala Lys His His His Arg Asp Asp Ala Phe Asp Val
1               5                   10

<210> SEQ ID NO 60
<211> LENGTH: 396
<212> TYPE: DNA
<213> ORGANISM: Artificial
<220> FEATURE:
<223> OTHER INFORMATION: Synthetic construct

<400> SEQUENCE: 60
atggcttgga cccccactcct cttcctcacc ctcctcctcc actgcacagg gtctctctcc      60
cagcctgtgg tgactcaatc gccctctgcc tctgcctccc tgggagcctc ggtcaggctc     120
acctgcactc tgagtagtgg ccgcacaacc ttcgccgtcg catggcatca gcagcagcca     180
cagaaggccc ctcgattctt gatgagaatt tataatgatg gcagccactt caagggggcc     240
gggattcctg atcgcttctc aggctccagt tctgggctg agcgctacct caccatctcc      300
agcctccagt ctgatgatga ggctgactat tactgtcaga cgtggggcag tggcagtgta     360
atgttcggcg agggaccaa ggtgaccgtc ctaggt                                396

<210> SEQ ID NO 61
<211> LENGTH: 132
<212> TYPE: PRT
<213> ORGANISM: Artificial
<220> FEATURE:
<223> OTHER INFORMATION: Synthetic construct

<400> SEQUENCE: 61

Met Ala Trp Thr Pro Leu Leu Phe Leu Thr Leu Leu Leu His Cys Thr
1               5                   10                  15

Gly Ser Leu Ser Gln Pro Val Val Thr Gln Ser Pro Ser Ala Ser Ala
                20                  25                  30

Ser Leu Gly Ala Ser Val Arg Leu Thr Cys Thr Leu Ser Ser Gly Arg
            35                  40                  45

Thr Thr Phe Ala Val Ala Trp His Gln Gln Gln Pro Gln Lys Ala Pro
        50                  55                  60

Arg Phe Leu Met Arg Ile Tyr Asn Asp Gly Ser His Phe Lys Gly Ala
65                  70                  75                  80

Gly Ile Pro Asp Arg Phe Ser Gly Ser Ser Gly Ala Glu Arg Tyr
                85                  90                  95

Leu Thr Ile Ser Ser Leu Gln Ser Asp Asp Glu Ala Asp Tyr Tyr Cys
            100                 105                 110

Gln Thr Trp Gly Ser Gly Ser Val Met Phe Gly Gly Gly Thr Lys Val
        115                 120                 125

Thr Val Leu Gly
    130

<210> SEQ ID NO 62
<211> LENGTH: 7
<212> TYPE: PRT
<213> ORGANISM: Artificial
<220> FEATURE:
<223> OTHER INFORMATION: Synthetic construct

<400> SEQUENCE: 62

Ser Gly Arg Thr Thr Phe Ala
1               5

<210> SEQ ID NO 63
<211> LENGTH: 7
<212> TYPE: PRT
<213> ORGANISM: Artificial
<220> FEATURE:
<223> OTHER INFORMATION: Synthetic construct

<400> SEQUENCE: 63

Ile Tyr Asn Asp Gly Ser His
1               5

<210> SEQ ID NO 64
<211> LENGTH: 9
<212> TYPE: PRT
<213> ORGANISM: Artificial
<220> FEATURE:
<223> OTHER INFORMATION: Synthetic construct

<400> SEQUENCE: 64

Gln Thr Trp Gly Ser Gly Ser Val Met
1               5

<210> SEQ ID NO 65
<211> LENGTH: 435
<212> TYPE: DNA
<213> ORGANISM: Artificial
<220> FEATURE:
<223> OTHER INFORMATION: Synthetic construct

<400> SEQUENCE: 65
atggactgga cctggaggat cctcttcttg gtggcagcag caacaggtgt ccactcccag    60
atgcagctgg aacaatctgg gtctgagttg aagaagcctg ggcctcagt gaaggtctcc    120 tgcaaggctt ctggatacac gttcactagt tatcctatga attgggtgcg acaggcccct    180
ggacaaggac ttgagtggat gggatggatc aacaccaaca acgggaaccc aacctatgcc    240
cgggacttca caggacgatt tgtcttctcc ttggacgcct ctgtcaacac ggcacatctg    300
cagatcacca gcctagaggc tgaggacacc gccgtctatt actgtgcgag agccggtttc    360
gaaatatatg gtgatgcgtt cacctactac gggatggacg tctggggcca gggaaccacg    420
gtcaccgtct cttca                                                    435

```
<210> SEQ ID NO 66
<211> LENGTH: 145
<212> TYPE: PRT
<213> ORGANISM: Artificial
<220> FEATURE:
<223> OTHER INFORMATION: Synthetic construct

<400> SEQUENCE: 66

Met Asp Trp Thr Trp Arg Ile Leu Phe Leu Val Ala Ala Thr Gly
1               5                   10                  15

Val His Ser Gln Met Gln Leu Glu Gln Ser Gly Ser Glu Leu Lys Lys
            20                  25                  30

Pro Gly Ala Ser Val Lys Val Ser Cys Lys Ala Ser Gly Tyr Thr Phe
        35                  40                  45

Thr Ser Tyr Pro Met Asn Trp Val Arg Gln Ala Pro Gly Gln Gly Leu
    50                  55                  60

Glu Trp Met Gly Trp Ile Asn Thr Asn Asn Gly Asn Pro Thr Tyr Ala
65                  70                  75                  80

Arg Asp Phe Thr Gly Arg Phe Val Phe Ser Leu Asp Ala Ser Val Asn
                85                  90                  95

Thr Ala His Leu Gln Ile Thr Ser Leu Glu Ala Glu Asp Thr Ala Val
            100                 105                 110

Tyr Tyr Cys Ala Arg Ala Gly Phe Glu Ile Tyr Gly Asp Ala Phe Thr
        115                 120                 125

Tyr Tyr Gly Met Asp Val Trp Gly Gln Gly Thr Thr Val Thr Val Ser
    130                 135                 140

Ser
145

<210> SEQ ID NO 67
<211> LENGTH: 8
<212> TYPE: PRT
<213> ORGANISM: Artificial
<220> FEATURE:
<223> OTHER INFORMATION: Synthetic construct

<400> SEQUENCE: 67

Gly Tyr Thr Phe Thr Ser Tyr Pro
1               5

<210> SEQ ID NO 68
<211> LENGTH: 8
<212> TYPE: PRT
<213> ORGANISM: Artificial
<220> FEATURE:
<223> OTHER INFORMATION: Synthetic construct

<400> SEQUENCE: 68

Ile Asn Thr Asn Asn Gly Asn Pro
1               5

<210> SEQ ID NO 69
<211> LENGTH: 19
<212> TYPE: PRT
<213> ORGANISM: Artificial
<220> FEATURE:
<223> OTHER INFORMATION: Synthetic construct

<400> SEQUENCE: 69

Ala Arg Ala Gly Phe Glu Ile Tyr Gly Asp Ala Phe Thr Tyr Tyr Gly
1               5                   10                  15

Met Asp Val
```

<210> SEQ ID NO 70
<211> LENGTH: 387
<212> TYPE: DNA
<213> ORGANISM: Artificial
<220> FEATURE:
<223> OTHER INFORMATION: Synthetic construct

<400> SEQUENCE: 70

```
atggcctggg ctctgctgct cctcaccctc ctcactcagg gcacagggtc ctgggcccag      60
tctgccctga ctcagcctgc ctccgtgtct gggtctcctg gacagttgat caccatctcc     120
tgcattggat ccaccggaga cattggcgct tataaatttg tctcctggta ccaacaatac     180
cccgggaagg cccccaagct catgatttat gaggtcagta atcggccctc aggaatctct     240
agtcgcttct ctggctccaa gtctggcaat acggcctccc tgaccatctc tgggctgcag     300
gtggacgacg aggctgatta ttattgtagt tcatatagag caacactac tctcttcggc     360 ggagggacca agctgaccgt cctaggt                                         387
```

<210> SEQ ID NO 71
<211> LENGTH: 129
<212> TYPE: PRT
<213> ORGANISM: Artificial
<220> FEATURE:
<223> OTHER INFORMATION: Synthetic construct

<400> SEQUENCE: 71

Met Ala Trp Ala Leu Leu Leu Thr Leu Leu Thr Gln Gly Thr Gly
1               5                   10                  15

Ser Trp Ala Gln Ser Ala Leu Thr Gln Pro Ala Ser Val Ser Gly Ser
            20                  25                  30

Pro Gly Gln Leu Ile Thr Ile Ser Cys Ile Gly Ser Thr Gly Asp Ile
        35                  40                  45

Gly Ala Tyr Lys Phe Val Ser Trp Tyr Gln Gln Tyr Pro Gly Lys Ala
    50                  55                  60

Pro Lys Leu Met Ile Tyr Glu Val Ser Asn Arg Pro Ser Gly Ile Ser
65                  70                  75                  80

Ser Arg Phe Ser Gly Ser Lys Ser Gly Asn Thr Ala Ser Leu Thr Ile
                85                  90                  95

Ser Gly Leu Gln Val Asp Asp Glu Ala Asp Tyr Tyr Cys Ser Ser Tyr
            100                 105                 110

Arg Gly Asn Thr Thr Leu Phe Gly Gly Thr Lys Leu Thr Val Leu
        115                 120                 125

Gly

<210> SEQ ID NO 72
<211> LENGTH: 9
<212> TYPE: PRT
<213> ORGANISM: Artificial
<220> FEATURE:
<223> OTHER INFORMATION: Synthetic construct

<400> SEQUENCE: 72

Thr Gly Asp Ile Gly Ala Tyr Lys Phe
1               5

<210> SEQ ID NO 73
<211> LENGTH: 4
<212> TYPE: PRT
<213> ORGANISM: Artificial

<220> FEATURE:
<223> OTHER INFORMATION: Synthetic construct

<400> SEQUENCE: 73

Glu Val Ser Asn
1

<210> SEQ ID NO 74
<211> LENGTH: 9
<212> TYPE: PRT
<213> ORGANISM: Artificial
<220> FEATURE:
<223> OTHER INFORMATION: Synthetic construct

<400> SEQUENCE: 74

Ser Ser Tyr Arg Gly Asn Thr Thr Leu
1               5

<210> SEQ ID NO 75
<211> LENGTH: 417
<212> TYPE: DNA
<213> ORGANISM: Artificial
<220> FEATURE:
<223> OTHER INFORMATION: Synthetic construct

<400> SEQUENCE: 75
atggactgga cctggagggt cttctgcttg ctggctgtag ctccaggtgc tcactcccag    60
gtgcagttgg tgcagtctgg ggctgaggtg aagaagcctg gggcctcagt gaaggtttcc   120
tgcaggacat ctggatacag tttcactagg tactatattc actgggtgcg acagtctcct   180
gggcgggggc ttgagtggat gggaataatc gatcctaaca atggtggcac aacgtccgca   240
aagaccttgc tgggcaaggt ctccatgacc agagacacgt ccacgagcac agcacacctg   300
gagttgacca gcctgggacc tgaagacacg gccgtctatt attgtgctat tttgtacagt   360
aacggcttgg aggtctggga ctactggggc cagggcaccc tggtcaccgt ctcctca     417

<210> SEQ ID NO 76
<211> LENGTH: 139
<212> TYPE: PRT
<213> ORGANISM: Artificial
<220> FEATURE:
<223> OTHER INFORMATION: Synthetic construct

<400> SEQUENCE: 76

Met Asp Trp Thr Trp Arg Val Phe Cys Leu Leu Ala Val Ala Pro Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Arg Thr Ser Gly Tyr Ser Phe
        35                  40                  45

Thr Arg Tyr Tyr Ile His Trp Val Arg Gln Ser Pro Gly Arg Gly Leu
    50                  55                  60

Glu Trp Met Gly Ile Ile Asp Pro Asn Asn Gly Gly Thr Thr Ser Ala
65                  70                  75                  80

Lys Thr Leu Leu Gly Lys Val Ser Met Thr Arg Asp Thr Ser Thr Ser
                85                  90                  95

Thr Ala His Leu Glu Leu Thr Ser Leu Gly Pro Glu Asp Thr Ala Val
            100                 105                 110

Tyr Tyr Cys Ala Ile Leu Tyr Ser Asn Gly Leu Glu Val Trp Asp Tyr
        115                 120                 125

Trp Gly Gln Gly Thr Leu Val Thr Val Ser Ser
        130                 135

<210> SEQ ID NO 77
<211> LENGTH: 8
<212> TYPE: PRT
<213> ORGANISM: Artificial
<220> FEATURE:
<223> OTHER INFORMATION: Synthetic construct

<400> SEQUENCE: 77

Gly Tyr Ser Phe Thr Arg Tyr Tyr
1               5

<210> SEQ ID NO 78
<211> LENGTH: 8
<212> TYPE: PRT
<213> ORGANISM: Artificial
<220> FEATURE:
<223> OTHER INFORMATION: Synthetic construct

<400> SEQUENCE: 78

Ile Asp Pro Asn Asn Gly Gly Thr
1               5

<210> SEQ ID NO 79
<211> LENGTH: 13
<212> TYPE: PRT
<213> ORGANISM: Artificial
<220> FEATURE:
<223> OTHER INFORMATION: Synthetic construct

<400> SEQUENCE: 79

Ala Ile Leu Tyr Ser Asn Gly Leu Glu Val Trp Asp Tyr
1               5                   10

<210> SEQ ID NO 80
<211> LENGTH: 378
<212> TYPE: DNA
<213> ORGANISM: Artificial
<220> FEATURE:
<223> OTHER INFORMATION: Synthetic construct

<400> SEQUENCE: 80
atggcctgga cccctctcct gctccccctc ctcactttct gcacagtctc tgcggcctcc      60
catgagctga cacagcctcc ctcggtgtca gtgtccccag acaaacggcc ccagatcacc     120
tgctctggag atactttgcc agataattat gcttattggt accagcagag gtcaggccag     180
gcccctgtac tggtcgtcta tgaggacaac aaacgaccct ccgggatccc tgagagattc     240
tctggctcca gctcagggac aatggccacc ttgactatca gtggggccca ggtggaggat     300
gatgctgact actattgtta ctcatcagac agaagtaaca acttcttcgg cggagggacc     360
aagttgaccg tcctgagt                                                    378

<210> SEQ ID NO 81
<211> LENGTH: 126
<212> TYPE: PRT
<213> ORGANISM: Artificial
<220> FEATURE:
<223> OTHER INFORMATION: Synthetic construct

<400> SEQUENCE: 81

Met Ala Trp Thr Pro Leu Leu Leu Pro Leu Leu Thr Phe Cys Thr Val
1               5                   10                  15

```
Ser Ala Ala Ser His Glu Leu Thr Gln Pro Pro Val Ser Val Ser
                20                  25                  30

Pro Gly Gln Thr Ala Gln Ile Thr Cys Ser Gly Asp Thr Leu Pro Asp
            35                  40                  45

Asn Tyr Ala Tyr Trp Tyr Gln Gln Arg Ser Gly Gln Ala Pro Val Leu
        50                  55                  60

Val Val Tyr Glu Asp Asn Lys Arg Pro Ser Gly Ile Pro Glu Arg Phe
65                  70                  75                  80

Ser Gly Ser Ser Ser Gly Thr Met Ala Thr Leu Thr Ile Ser Gly Ala
                85                  90                  95

Gln Val Glu Asp Asp Ala Asp Tyr Tyr Cys Tyr Ser Ser Asp Arg Ser
            100                 105                 110

Asn Asn Phe Phe Gly Gly Gly Thr Lys Leu Thr Val Leu Ser
        115                 120                 125

<210> SEQ ID NO 82
<211> LENGTH: 6
<212> TYPE: PRT
<213> ORGANISM: Artificial
<220> FEATURE:
<223> OTHER INFORMATION: Synthetic construct

<400> SEQUENCE: 82

Thr Leu Pro Asp Asn Tyr
1               5

<210> SEQ ID NO 83
<211> LENGTH: 4
<212> TYPE: PRT
<213> ORGANISM: Artificial
<220> FEATURE:
<223> OTHER INFORMATION: Synthetic construct

<400> SEQUENCE: 83

Glu Asp Asn Lys
1

<210> SEQ ID NO 84
<211> LENGTH: 9
<212> TYPE: PRT
<213> ORGANISM: Artificial
<220> FEATURE:
<223> OTHER INFORMATION: Synthetic construct

<400> SEQUENCE: 84

Tyr Ser Ser Asp Arg Ser Asn Asn Phe
1               5

<210> SEQ ID NO 85
<211> LENGTH: 426
<212> TYPE: DNA
<213> ORGANISM: Artificial
<220> FEATURE:
<223> OTHER INFORMATION: Synthetic construct

<400> SEQUENCE: 85
atggagtttg ggctgagctg gcttttctt gcggctattt taaaagggat gcactgtgag      60
gtgcagttgt tggagtctgg gggaggcttg gtacagccgg ggggtccct aagactctcc    120 tgtgcagcct ctggattcgc cttcagtagt tttggcatga gttgggtccg ccaggctcca    180
gggaaggggc tggagtgggt ctcaagtatt agtgacggcg gtgttgacac atacaacgca    240
gactccgtga agggccgctt caccatctcc agagacaagt ccaacagagt gtatctgcaa    300
```

```
atgaccagcc tgagagccga ggacacggcc gtgtattact gtgcgagaat tcgacctaat    360
tatgtcacgg tcaaccgtgt gggcctggac tactggggcc agggaatcca ggtcaccgtc    420
tcttca                                                              426
```

<210> SEQ ID NO 86
<211> LENGTH: 142
<212> TYPE: PRT
<213> ORGANISM: Artificial
<220> FEATURE:
<223> OTHER INFORMATION: Synthetic construct

<400> SEQUENCE: 86

```
Met Glu Phe Gly Leu Ser Trp Leu Phe Leu Ala Ala Ile Leu Lys Gly
1               5                   10                  15

Met His Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Ala Phe
        35                  40                  45

Ser Ser Phe Gly Met Ser Trp Val Arg Gln Ala Pro Gly Lys Gly Leu
    50                  55                  60

Glu Trp Val Ser Ser Ile Ser Asp Gly Gly Val Asp Thr Tyr Asn Ala
65                  70                  75                  80

Asp Ser Val Lys Gly Arg Phe Thr Ile Ser Arg Asp Lys Ser Asn Arg
                85                  90                  95

Val Tyr Leu Gln Met Thr Ser Leu Arg Ala Glu Asp Thr Ala Val Tyr
            100                 105                 110

Tyr Cys Ala Arg Ile Arg Pro Asn Tyr Val Thr Val Asn Arg Val Gly
        115                 120                 125

Leu Asp Tyr Trp Gly Gln Gly Ile Gln Val Thr Val Ser Ser
    130                 135                 140
```

<210> SEQ ID NO 87
<211> LENGTH: 8
<212> TYPE: PRT
<213> ORGANISM: Artificial
<220> FEATURE:
<223> OTHER INFORMATION: Synthetic construct

<400> SEQUENCE: 87

```
Gly Phe Ala Phe Ser Ser Phe Gly
1               5
```

<210> SEQ ID NO 88
<211> LENGTH: 7
<212> TYPE: PRT
<213> ORGANISM: Artificial
<220> FEATURE:
<223> OTHER INFORMATION: Synthetic construct

<400> SEQUENCE: 88

```
Ile Ser Asp Gly Gly Val Asp
1               5
```

<210> SEQ ID NO 89
<211> LENGTH: 17
<212> TYPE: PRT
<213> ORGANISM: Artificial
<220> FEATURE:
<223> OTHER INFORMATION: Synthetic construct

<400> SEQUENCE: 89

Ala Arg Ile Arg Pro Asn Tyr Val Thr Val Asn Arg Val Gly Leu Asp
1               5                   10                  15

Tyr

<210> SEQ ID NO 90
<211> LENGTH: 396
<212> TYPE: DNA
<213> ORGANISM: Artificial
<220> FEATURE:
<223> OTHER INFORMATION: Synthetic construct

<400> SEQUENCE: 90
atgaggctcc ctgctcagct cctggggctg ctaatgctct gggtctctgg atccagtggg      60
gatattgtga tgactcagtc ttcactctcc ctgcccgtca ccctggaga gccggcctcc      120 atctcctgca ggtctagtca gagcctcctg catagtaatg gatacaacta tttggattgg     180
tacctgcaga agccagggca gtctccacag ctcctgatct atttgacttc ttatcgggcc     240
cccggggtcc ctgacaggtt cagtggcagt ggatcaggca cagatttcac actgaaaatc     300
agcagagtgg aggctgagga tgttggggtt tattactgca tgcaagctct acaaagtcct     360
cccactttcg gccctgggac caaagtggat atcaaa                               396

<210> SEQ ID NO 91
<211> LENGTH: 132
<212> TYPE: PRT
<213> ORGANISM: Artificial
<220> FEATURE:
<223> OTHER INFORMATION: Synthetic construct

<400> SEQUENCE: 91

Met Arg Leu Pro Ala Gln Leu Leu Gly Leu Leu Met Leu Trp Val Ser
1               5                   10                  15

Gly Ser Ser Gly Asp Ile Val Met Thr Gln Ser Ser Leu Ser Leu Pro
                20                  25                  30

Val Thr Pro Gly Glu Pro Ala Ser Ile Ser Cys Arg Ser Ser Gln Ser
            35                  40                  45

Leu Leu His Ser Asn Gly Tyr Asn Tyr Leu Asp Trp Tyr Leu Gln Lys
        50                  55                  60

Pro Gly Gln Ser Pro Gln Leu Leu Ile Tyr Leu Thr Ser Tyr Arg Ala
65                  70                  75                  80

Pro Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Met Gln Ala Leu Gln Ser Pro Pro Thr Phe Gly Pro Gly Thr Lys
        115                 120                 125

Val Asp Ile Lys
    130

<210> SEQ ID NO 92
<211> LENGTH: 11
<212> TYPE: PRT
<213> ORGANISM: Artificial
<220> FEATURE:
<223> OTHER INFORMATION: Synthetic construct

<400> SEQUENCE: 92

Gln Ser Leu Leu His Ser Asn Gly Tyr Asn Tyr
1               5                   10

<210> SEQ ID NO 93
<211> LENGTH: 4
<212> TYPE: PRT
<213> ORGANISM: Artificial
<220> FEATURE:
<223> OTHER INFORMATION: Synthetic construct

<400> SEQUENCE: 93

Leu Thr Ser Tyr
1

<210> SEQ ID NO 94
<211> LENGTH: 9
<212> TYPE: PRT
<213> ORGANISM: Artificial
<220> FEATURE:
<223> OTHER INFORMATION: Synthetic construct

<400> SEQUENCE: 94

Met Gln Ala Leu Gln Ser Pro Pro Thr
1               5

<210> SEQ ID NO 95
<211> LENGTH: 429
<212> TYPE: DNA
<213> ORGANISM: Artificial
<220> FEATURE:
<223> OTHER INFORMATION: Synthetic construct

<400> SEQUENCE: 95

```
atggagtttg ggctgagctg ggttttcctc gttgctcttt taagagctgt ccagtgtcag     60
gtgcagctgg aggagtctgg gggaggcgtg gtccagcctg gaggtccct gagactctcc    120
tgtgcagcct ctggattcac cttcagtaga tttggcatgc actgggtccg ccaggctcca    180
ggcaggggc tggagtgggt ggcagttata tcaaatgatg gaaattataa atattctgct    240
gactccgtga ggggccgatt caccatctcc agagacaatt ccaggaacac cctgtatctc    300
caaatgaaca gcctgagaat tgaggacacg gctgtgtatt actgtgcgaa agtcatgtat    360
gacttcggtc cttactacta ctacggtctc gacgtctggg gccaagggc cacggtcacc    420
gtctcttca                                                             429
```

<210> SEQ ID NO 96
<211> LENGTH: 143
<212> TYPE: PRT
<213> ORGANISM: Artificial
<220> FEATURE:
<223> OTHER INFORMATION: Synthetic construct

<400> SEQUENCE: 96

Met Glu Phe Gly Leu Ser Trp Val Phe Leu Val Ala Leu Leu Arg Ala
1               5                   10                  15

Val Gln Cys Gln Val Gln Leu Glu Glu Ser Gly Gly Gly Val Val Gln
                20                  25                  30

Pro Gly Arg Ser Leu Arg Leu Ser Cys Ala Ala Ser Gly Phe Thr Phe
            35                  40                  45

Ser Arg Phe Gly Met His Trp Val Arg Gln Ala Pro Gly Arg Gly Leu
        50                  55                  60

Glu Trp Val Ala Val Ile Ser Asn Asp Gly Asn Tyr Lys Tyr Ser Ala
65                  70                  75                  80

Asp Ser Val Arg Gly Arg Phe Thr Ile Ser Arg Asp Asn Ser Arg Asn

```
                    85                  90                  95
Thr Leu Tyr Leu Gln Met Asn Ser Leu Arg Ile Glu Asp Thr Ala Val
            100                 105                 110

Tyr Tyr Cys Ala Lys Val Met Tyr Asp Phe Gly Pro Tyr Tyr Tyr Tyr
        115                 120                 125

Gly Leu Asp Val Trp Gly Gln Gly Ala Thr Val Thr Val Ser Ser
    130                 135                 140
```

<210> SEQ ID NO 97
<211> LENGTH: 8
<212> TYPE: PRT
<213> ORGANISM: Artificial
<220> FEATURE:
<223> OTHER INFORMATION: Synthetic construct

<400> SEQUENCE: 97

```
Gly Phe Thr Phe Ser Arg Phe Gly
1               5
```

<210> SEQ ID NO 98
<211> LENGTH: 8
<212> TYPE: PRT
<213> ORGANISM: Artificial
<220> FEATURE:
<223> OTHER INFORMATION: Synthetic construct

<400> SEQUENCE: 98

```
Ile Ser Asn Asp Gly Asn Tyr Lys
1               5
```

<210> SEQ ID NO 99
<211> LENGTH: 17
<212> TYPE: PRT
<213> ORGANISM: Artificial
<220> FEATURE:
<223> OTHER INFORMATION: Synthetic construct

<400> SEQUENCE: 99

```
Ala Lys Val Met Tyr Asp Phe Gly Pro Tyr Tyr Tyr Tyr Gly Leu Asp
1               5                   10                  15

Val
```

<210> SEQ ID NO 100
<211> LENGTH: 384
<212> TYPE: DNA
<213> ORGANISM: Artificial
<220> FEATURE:
<223> OTHER INFORMATION: Synthetic construct

<400> SEQUENCE: 100

```
atggcctgga ccgttctcct cctcggcctc ctctctcact gcacaggctc tgtgacctcc      60
tatgtgctga ctcagccacc ctcggtgtca gtggccccag acagacggc caggattacc      120 tgtggggaa acaacattgg aaataataga atacactggt accagcagaa gccaggccag      180
gcccctgtgc tggtcgtcta tgccaatatc gaccggccct cagggatccc tgagcgattt      240
tctggctcca actctgggaa cacgccacc ctgaccatca ataggtcga ggccggggat      300 gaggccgact attactgtca ggtgtgggat agtggtagtg atcattgggt gttcggcgga      360
gggaccatgc tgaccgtcct aggt                                            384
```

<210> SEQ ID NO 101
<211> LENGTH: 128

<212> TYPE: PRT
<213> ORGANISM: Artificial
<220> FEATURE:
<223> OTHER INFORMATION: Synthetic construct

<400> SEQUENCE: 101

Met Ala Trp Thr Val Leu Leu Leu Gly Leu Leu Ser His Cys Thr Gly
1               5                   10                  15

Ser Val Thr Ser Tyr Val Leu Thr Gln Pro Pro Ser Val Ser Val Ala
                20                  25                  30

Pro Gly Gln Thr Ala Arg Ile Thr Cys Gly Gly Asn Asn Ile Gly Asn
            35                  40                  45

Asn Arg Ile His Trp Tyr Gln Gln Lys Pro Gly Gln Ala Pro Val Leu
        50                  55                  60

Val Val Tyr Ala Asn Ile Asp Arg Pro Ser Gly Ile Pro Glu Arg Phe
65                  70                  75                  80

Ser Gly Ser Asn Ser Gly Asn Thr Ala Thr Leu Thr Ile Asn Arg Val
                85                  90                  95

Glu Ala Gly Asp Glu Ala Asp Tyr Tyr Cys Gln Val Trp Asp Ser Gly
            100                 105                 110

Ser Asp His Trp Val Phe Gly Gly Gly Thr Met Leu Thr Val Leu Gly
        115                 120                 125

<210> SEQ ID NO 102
<211> LENGTH: 6
<212> TYPE: PRT
<213> ORGANISM: Artificial
<220> FEATURE:
<223> OTHER INFORMATION: Synthetic construct

<400> SEQUENCE: 102

Asn Ile Gly Asn Asn Arg
1               5

<210> SEQ ID NO 103
<211> LENGTH: 4
<212> TYPE: PRT
<213> ORGANISM: Artificial
<220> FEATURE:
<223> OTHER INFORMATION: Synthetic construct

<400> SEQUENCE: 103

Ala Asn Ile Asp
1

<210> SEQ ID NO 104
<211> LENGTH: 11
<212> TYPE: PRT
<213> ORGANISM: Artificial
<220> FEATURE:
<223> OTHER INFORMATION: Synthetic construct

<400> SEQUENCE: 104

Gln Val Trp Asp Ser Gly Ser Asp His Trp Val
1               5                   10

<210> SEQ ID NO 105
<211> LENGTH: 447
<212> TYPE: DNA
<213> ORGANISM: Artificial
<220> FEATURE:
<223> OTHER INFORMATION: Synthetic construct

<400> SEQUENCE: 105

-continued

```
atggactgga cctggaggtt cctctttgtg gtggcagcag ctacaggtgt ccagtcccag    60
gtccagctgg tgcagtctgg ggctgaggtg aagaggcctg gtcctcggt gaaagtctcc    120 tgcaaggctt ctggagacaa cttcaacaac tatgccttcc actgggtgcg ccaggcccct   180
ggacaagggc ttgagtggat ggggcggacc atccctttcc ttggtttaac aagctactca   240
ccgaatatcc agggcagagt ctccatttcc gcggacaaat ccacggccac agccttcatg   300
gagatgagcg gcctgaggtc tgaggacacg gccatgtatt actgtgcgag cagcattcga   360
ttgggggact ttttatatag agcctcttac tactactcct cccctctgga cgtctggggc   420
caagggacca cggtcaccgt ctcctca                                      447
```

<210> SEQ ID NO 106
<211> LENGTH: 149
<212> TYPE: PRT
<213> ORGANISM: Artificial
<220> FEATURE:
<223> OTHER INFORMATION: Synthetic construct

<400> SEQUENCE: 106

```
Met Asp Trp Thr Trp Arg Phe Leu Phe Val Val Ala Ala Ala Thr Gly
1               5                   10                  15

Val Gln Ser Gln Val Gln Leu Val Gln Ser Gly Ala Glu Val Lys Arg
            20                  25                  30

Pro Gly Ser Ser Val Lys Val Ser Cys Lys Ala Ser Gly Asp Asn Phe
        35                  40                  45

Asn Asn Tyr Ala Phe His Trp Val Arg Gln Ala Pro Gly Gln Gly Leu
    50                  55                  60

Glu Trp Met Gly Arg Thr Ile Pro Phe Leu Gly Leu Thr Ser Tyr Ser
65                  70                  75                  80

Pro Asn Ile Gln Gly Arg Val Ser Ile Ser Ala Asp Lys Ser Thr Ala
                85                  90                  95

Thr Ala Phe Met Glu Met Ser Gly Leu Arg Ser Glu Asp Thr Ala Met
            100                 105                 110

Tyr Tyr Cys Ala Ser Ser Ile Arg Leu Gly Asp Phe Leu Tyr Arg Ala
        115                 120                 125

Ser Tyr Tyr Tyr Ser Ser Pro Leu Asp Val Trp Gly Gln Gly Thr Thr
    130                 135                 140

Val Thr Val Ser Ser
145
```

<210> SEQ ID NO 107
<211> LENGTH: 8
<212> TYPE: PRT
<213> ORGANISM: Artificial
<220> FEATURE:
<223> OTHER INFORMATION: Synthetic construct

<400> SEQUENCE: 107

```
Gly Asp Asn Phe Asn Asn Tyr Ala
1               5
```

<210> SEQ ID NO 108
<211> LENGTH: 8
<212> TYPE: PRT
<213> ORGANISM: Artificial
<220> FEATURE:
<223> OTHER INFORMATION: Synthetic construct

<400> SEQUENCE: 108

Thr Ile Pro Phe Leu Gly Leu Thr
1               5

<210> SEQ ID NO 109
<211> LENGTH: 23
<212> TYPE: PRT
<213> ORGANISM: Artificial
<220> FEATURE:
<223> OTHER INFORMATION: Synthetic construct

<400> SEQUENCE: 109

Ala Ser Ser Ile Arg Leu Gly Asp Phe Leu Tyr Arg Ala Ser Tyr Tyr
1               5                   10                  15

Tyr Ser Ser Pro Leu Asp Val
            20

<210> SEQ ID NO 110
<211> LENGTH: 381
<212> TYPE: DNA
<213> ORGANISM: Artificial
<220> FEATURE:
<223> OTHER INFORMATION: Synthetic construct

<400> SEQUENCE: 110
atggaaaccc cagcgcagct tctcctcctc ctgctactct ggctcccaga taccaccgga      60
gaagttgtgt tgacgcagtc tccaggcacc ctgtctttgt ctccagggga tagagccacc     120
ctgacctgca gggccggtca gactattagc aacagttact tagcctggta ccagcagaaa     180
cctggccagg ctcccaggct cctcatctct ggtgtgtcca gtagggccac tggcatccca     240
gacaggttca gtggcagtgg gtctgggaca gacttcactc tcaccatcag cagactggag     300
cctgaagatt ttgcagtata ttactgtcag ctgtatggta actcaccctc tttcggccaa     360
gggacacgac tggagattaa a                                               381

<210> SEQ ID NO 111
<211> LENGTH: 127
<212> TYPE: PRT
<213> ORGANISM: Artificial
<220> FEATURE:
<223> OTHER INFORMATION: Synthetic construct

<400> SEQUENCE: 111

Met Glu Thr Pro Ala Gln Leu Leu Leu Leu Leu Leu Trp Leu Pro
1               5                   10                  15

Asp Thr Thr Gly Glu Val Val Leu Thr Gln Ser Pro Gly Thr Leu Ser
            20                  25                  30

Leu Ser Pro Gly Asp Arg Ala Thr Leu Thr Cys Arg Ala Gly Gln Thr
        35                  40                  45

Ile Ser Asn Ser Tyr Leu Ala Trp Tyr Gln Gln Lys Pro Gly Gln Ala
    50                  55                  60

Pro Arg Leu Leu Ile Ser Gly Val Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Leu Tyr
            100                 105                 110

Gly Asn Ser Pro Ser Phe Gly Gln Gly Thr Arg Leu Glu Ile Lys
        115                 120                 125

<210> SEQ ID NO 112
<211> LENGTH: 7
<212> TYPE: PRT
<213> ORGANISM: Artificial
<220> FEATURE:
<223> OTHER INFORMATION: Synthetic construct

<400> SEQUENCE: 112

Gln Thr Ile Ser Asn Ser Tyr
1               5

<210> SEQ ID NO 113
<211> LENGTH: 4
<212> TYPE: PRT
<213> ORGANISM: Artificial
<220> FEATURE:
<223> OTHER INFORMATION: Synthetic construct

<400> SEQUENCE: 113

Gly Val Ser Ser
1

<210> SEQ ID NO 114
<211> LENGTH: 8
<212> TYPE: PRT
<213> ORGANISM: Artificial
<220> FEATURE:
<223> OTHER INFORMATION: Synthetic construct

<400> SEQUENCE: 114

Gln Leu Tyr Gly Asn Ser Pro Ser
1               5

<210> SEQ ID NO 115
<211> LENGTH: 417
<212> TYPE: DNA
<213> ORGANISM: Artificial
<220> FEATURE:
<223> OTHER INFORMATION: Synthetic construct

<400> SEQUENCE: 115
atggagtttg ggctgagctg ggttttcctt gttgcaatgt taaaaggtgt ccagtgcgag      60
gtgcaggtgg tggagtctgg gggaggcttg gtccagccgg ggggtccat gagactctcc     120 tgtgcagcct ctggattcac cgtcaatagc aaattcatga cctgggtccg ccaggctcca     180
gggacggggc tggagtgcgt ctcgattatt tataacgatg gtaccacata ctataaagac     240
tccgtgaagg gccggttcac catctccaga gacaattcca agaacacgtt gtatcttcaa     300
atgaacaggc tgagacctga ggacacggct gtctatttct gtgcgagaag gggattttc     360 ggggggaatg aagcttttga tatctggggc caagggacac tggtcaccgt ctcttca        417

<210> SEQ ID NO 116
<211> LENGTH: 139
<212> TYPE: PRT
<213> ORGANISM: Artificial
<220> FEATURE:
<223> OTHER INFORMATION: Synthetic construct

<400> SEQUENCE: 116

Met Glu Phe Gly Leu Ser Trp Val Phe Leu Val Ala Met Leu Lys Gly
1               5                   10                  15

Val Gln Cys Glu Val Gln Val Val Glu Ser Gly Gly Gly Leu Val Gln
            20                  25                  30

Pro Gly Gly Ser Met Arg Leu Ser Cys Ala Ala Ser Gly Phe Thr Val

```
           35                  40                  45
Asn Ser Lys Phe Met Thr Trp Val Arg Gln Ala Pro Gly Thr Gly Leu
     50                  55                  60

Glu Cys Val Ser Ile Ile Tyr Asn Asp Gly Thr Thr Tyr Tyr Lys Asp
 65                  70                  75                  80

Ser Val Lys Gly Arg Phe Thr Ile Ser Arg Asp Asn Ser Lys Asn Thr
                 85                  90                  95

Leu Tyr Leu Gln Met Asn Arg Leu Arg Pro Glu Asp Thr Ala Val Tyr
                100                 105                 110

Phe Cys Ala Arg Arg Gly Phe Phe Gly Gly Asn Glu Ala Phe Asp Ile
            115                 120                 125

Trp Gly Gln Gly Thr Leu Val Thr Val Ser Ser
    130                 135
```

```
<210> SEQ ID NO 117
<211> LENGTH: 8
<212> TYPE: PRT
<213> ORGANISM: Artificial
<220> FEATURE:
<223> OTHER INFORMATION: Synthetic construct

<400> SEQUENCE: 117

Gly Phe Thr Val Asn Ser Lys Phe
1               5

<210> SEQ ID NO 118
<211> LENGTH: 7
<212> TYPE: PRT
<213> ORGANISM: Artificial
<220> FEATURE:
<223> OTHER INFORMATION: Synthetic construct

<400> SEQUENCE: 118

Ile Tyr Asn Asp Gly Thr Thr
1               5

<210> SEQ ID NO 119
<211> LENGTH: 14
<212> TYPE: PRT
<213> ORGANISM: Artificial
<220> FEATURE:
<223> OTHER INFORMATION: Synthetic construct

<400> SEQUENCE: 119

Ala Arg Arg Gly Phe Phe Gly Gly Asn Glu Ala Phe Asp Ile
1               5                   10

<210> SEQ ID NO 120
<211> LENGTH: 384
<212> TYPE: DNA
<213> ORGANISM: Artificial
<220> FEATURE:
<223> OTHER INFORMATION: Synthetic construct

<400> SEQUENCE: 120
atggaaaccc cagcgcagct tctcttcctc ctgctactct ggctcccaga tactaccgga      60
gaaattgtgt tgacgcagtc tccaggcacc ctgtctttgt ctccagggga aagagccacc     120
ctctcctgca gggccggtca gagtgttagc agcagctact tagcctggta ccaacagaga     180
cctggccagc ctcccaggct cctcgtctat ggtacatcca acagggccac tggcgtccca     240
gacagattca gtggcagcgg gtctgggaca gactccactc tcaccatcag cagactggag     300
```

```
cctgaagatt ttgcagtcta ttactgtcac cagtatagta gctcacttcc gacgttcggc    360
ccagggacca aggtggaaat caaa                                           384
```

<210> SEQ ID NO 121
<211> LENGTH: 128
<212> TYPE: PRT
<213> ORGANISM: Artificial
<220> FEATURE:
<223> OTHER INFORMATION: Synthetic construct

<400> SEQUENCE: 121

```
Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
                20                  25                  30

Leu Ser Pro Gly Glu Arg Ala Thr Leu Ser Cys Arg Ala Gly Gln Ser
            35                  40                  45

Val Ser Ser Ser Tyr Leu Ala Trp Tyr Gln Gln Arg Pro Gly Gln Pro
        50                  55                  60

Pro Arg Leu Leu Val Tyr Gly Thr Ser Asn Arg Ala Thr Gly Val Pro
65                  70                  75                  80

Asp Arg Phe Ser Gly Ser Gly Ser Gly Thr Asp Ser Thr Leu Thr Ile
                85                  90                  95

Ser Arg Leu Glu Pro Glu Asp Phe Ala Val Tyr Tyr Cys His Gln Tyr
            100                 105                 110

Ser Ser Ser Leu Pro Thr Phe Gly Pro Gly Thr Lys Val Glu Ile Lys
        115                 120                 125
```

<210> SEQ ID NO 122
<211> LENGTH: 7
<212> TYPE: PRT
<213> ORGANISM: Artificial
<220> FEATURE:
<223> OTHER INFORMATION: Synthetic construct

<400> SEQUENCE: 122

```
Gln Ser Val Ser Ser Ser Tyr
1               5
```

<210> SEQ ID NO 123
<211> LENGTH: 4
<212> TYPE: PRT
<213> ORGANISM: Artificial
<220> FEATURE:
<223> OTHER INFORMATION: Synthetic construct

<400> SEQUENCE: 123

```
Gly Thr Ser Asn
1
```

<210> SEQ ID NO 124
<211> LENGTH: 9
<212> TYPE: PRT
<213> ORGANISM: Artificial
<220> FEATURE:
<223> OTHER INFORMATION: Synthetic construct

<400> SEQUENCE: 124

```
His Gln Tyr Ser Ser Ser Leu Pro Thr
1               5
```

<210> SEQ ID NO 125

-continued

<211> LENGTH: 408
<212> TYPE: DNA
<213> ORGANISM: Artificial
<220> FEATURE:
<223> OTHER INFORMATION: Synthetic construct

<400> SEQUENCE: 125

```
atggactgga cctggaggat cctcttcttg gtggcagcag ccacaggagc ccactcccag    60
gtgcagctgg tgcagtctgg gactgaggtg aaaaagcctg gggcctcagt gagggtctcc   120
tgcaaggctt ctggatacag cttcaccgag tactatttgc actgggtgcg acaggcccca   180
ggacaaggcc ttgagtggat gggacggatc aaccctaaga gtggcaacac aaactatgca   240
cagaaactta acggaagggt caccatgacc agtgatacgt ccgtcaatgt agcctatttg   300
gaggtgagcg gcctgacatc tgacgacacg gccatatatt attgtacgag agacgataat   360
ggggctttcg tttactgggg ccagggaacc ctggtcaccg tctcctca              408
```

<210> SEQ ID NO 126
<211> LENGTH: 136
<212> TYPE: PRT
<213> ORGANISM: Artificial
<220> FEATURE:
<223> OTHER INFORMATION: Synthetic construct

<400> SEQUENCE: 126

Met Asp Trp Thr Trp Arg Ile Leu Phe Leu Val Ala Ala Thr Gly
1               5                   10                  15

Ala His Ser Gln Val Gln Leu Val Gln Ser Gly Thr Glu Val Lys Lys
            20                  25                  30

Pro Gly Ala Ser Val Arg Val Ser Cys Lys Ala Ser Gly Tyr Ser Phe
        35                  40                  45

Thr Glu Tyr Tyr Leu His Trp Val Arg Gln Ala Pro Gly Gln Gly Leu
    50                  55                  60

Glu Trp Met Gly Arg Ile Asn Pro Lys Ser Gly Asn Thr Asn Tyr Ala
65                  70                  75                  80

Gln Lys Leu Asn Gly Arg Val Thr Met Thr Ser Asp Thr Ser Val Asn
                85                  90                  95

Val Ala Tyr Leu Glu Val Ser Gly Leu Thr Ser Asp Asp Thr Ala Ile
            100                 105                 110

Tyr Tyr Cys Thr Arg Asp Asp Asn Gly Ala Phe Val Tyr Trp Gly Gln
        115                 120                 125

Gly Thr Leu Val Thr Val Ser Ser
    130                 135

<210> SEQ ID NO 127
<211> LENGTH: 8
<212> TYPE: PRT
<213> ORGANISM: Artificial
<220> FEATURE:
<223> OTHER INFORMATION: Synthetic construct

<400> SEQUENCE: 127

Gly Tyr Ser Phe Thr Glu Tyr Tyr
1               5

<210> SEQ ID NO 128
<211> LENGTH: 8
<212> TYPE: PRT
<213> ORGANISM: Artificial
<220> FEATURE:
<223> OTHER INFORMATION: Synthetic construct

<400> SEQUENCE: 128

Ile Asn Pro Lys Ser Gly Asn Thr
1               5

<210> SEQ ID NO 129
<211> LENGTH: 10
<212> TYPE: PRT
<213> ORGANISM: Artificial
<220> FEATURE:
<223> OTHER INFORMATION: Synthetic construct

<400> SEQUENCE: 129

Thr Arg Asp Asp Asn Gly Ala Phe Val Tyr
1               5                   10

<210> SEQ ID NO 130
<211> LENGTH: 399
<212> TYPE: DNA
<213> ORGANISM: Artificial
<220> FEATURE:
<223> OTHER INFORMATION: Synthetic construct

<400> SEQUENCE: 130

```
atggaagccc cagctcagct tctcttcctc ctgctactct gcctcccagt ttcagagacc    60
accggagaga ctgtgttgac acagtctcca gccaccctgt ctttgtctcc aggagaaaga   120
gccaccctct cctgcaggtc cagtcaggtt atcagcagct acttagcctg gttccaacaa   180
aaacctggcc aggctcccag gctcctcatc tatgatacat ccaacagggc cactggcatc   240
ccagccaggt tcagtggcag tgggtctggg acagacttca ctctcaccat cagtagccta   300
gagcctgagg attttgccgt ttattactgt cagcagcgta tcaactggcc tccgcgcgag   360
aaaatcacct tcggccctgg gaccaaggtg gatatcagg                          399
```

<210> SEQ ID NO 131
<211> LENGTH: 133
<212> TYPE: PRT
<213> ORGANISM: Artificial
<220> FEATURE:
<223> OTHER INFORMATION: Synthetic construct

<400> SEQUENCE: 131

Met Glu Ala Pro Ala Gln Leu Leu Phe Leu Leu Leu Leu Cys Leu Pro
1               5                   10                  15

Val Ser Glu Thr Thr Gly Glu Thr Val Leu Thr Gln Ser Pro Ala Thr
            20                  25                  30

Leu Ser Leu Ser Pro Gly Glu Arg Ala Thr Leu Ser Cys Arg Ser Ser
        35                  40                  45

Gln Val Ile Ser Ser Tyr Leu Ala Trp Phe Gln Gln Lys Pro Gly Gln
    50                  55                  60

Ala Pro Arg Leu Leu Ile Tyr Asp Thr Ser Asn Arg Ala Thr Gly Ile
65                  70                  75                  80

Pro Ala Arg Phe Ser Gly Ser Gly Ser Gly Thr Asp Phe Thr Leu Thr
                85                  90                  95

Ile Ser Ser Leu Glu Pro Glu Asp Phe Ala Val Tyr Tyr Cys Gln Gln
            100                 105                 110

Arg Ile Asn Trp Pro Pro Arg Glu Lys Ile Thr Phe Gly Pro Gly Thr
        115                 120                 125

Lys Val Asp Ile Arg
    130

<210> SEQ ID NO 132
<211> LENGTH: 417
<212> TYPE: DNA
<213> ORGANISM: Artificial
<220> FEATURE:
<223> OTHER INFORMATION: Synthetic construct

<400> SEQUENCE: 132

```
atggactgga cctggagggt cttctgcttg ctggctgtag ctccaggtgc tcactcccag      60
gtgcagatgg tgcaatctgg gactgaggtg aagaagcctg gggcctcagt gaaggtttcc     120
tgcaaggcgt ctggatacga cttcgccaaa tactatatat cctgggtgcg acaggccccc     180 ggacagggc tagagtggat gggaatgatc aaccctcaga acggagtcac aacctacaca      240
cagaaagtcc agggcaggt caccctgacc agggacacgt ccacgaccac agtttacatg      300
gagctcagca gcctgagatt tgaggacacg gccgtctatt attgtaatat tctctatatc     360
agtggttcga acgtttggga ttattggggc agggaaccc tggtcaccgt ctcttca        417
```

<210> SEQ ID NO 133
<211> LENGTH: 139
<212> TYPE: PRT
<213> ORGANISM: Artificial
<220> FEATURE:
<223> OTHER INFORMATION: Synthetic construct

<400> SEQUENCE: 133

Met Asp Trp Thr Trp Arg Val Phe Cys Leu Leu Ala Val Ala Pro Gly
1               5                   10                  15

Ala His Ser Gln Val Gln Met Val Gln Ser Gly Thr Glu Val Lys Lys
            20                  25                  30

Pro Gly Ala Ser Val Lys Val Ser Cys Lys Ala Ser Gly Tyr Asp Phe
        35                  40                  45

Ala Lys Tyr Tyr Ile Ser Trp Val Arg Gln Ala Pro Gly Gln Gly Leu
    50                  55                  60

Glu Trp Met Gly Met Ile Asn Pro Gln Asn Gly Val Thr Thr Tyr Thr
65                  70                  75                  80

Gln Lys Val Gln Gly Arg Val Thr Leu Thr Arg Asp Thr Ser Thr Thr
                85                  90                  95

Thr Val Tyr Met Glu Leu Ser Ser Leu Arg Phe Glu Asp Thr Ala Val
            100                 105                 110

Tyr Tyr Cys Asn Ile Leu Tyr Ile Ser Gly Ser Asn Val Trp Asp Tyr
        115                 120                 125

Trp Gly Gln Gly Thr Leu Val Thr Val Ser Ser
    130                 135

<210> SEQ ID NO 134
<211> LENGTH: 8
<212> TYPE: PRT
<213> ORGANISM: Artificial
<220> FEATURE:
<223> OTHER INFORMATION: Synthetic construct

<400> SEQUENCE: 134

Gly Tyr Asp Phe Ala Lys Tyr Tyr
1               5

<210> SEQ ID NO 135
<211> LENGTH: 8
<212> TYPE: PRT

<213> ORGANISM: Artificial
<220> FEATURE:
<223> OTHER INFORMATION: Synthetic construct

<400> SEQUENCE: 135

Ile Asn Pro Gln Asn Gly Val Thr
1               5

<210> SEQ ID NO 136
<211> LENGTH: 13
<212> TYPE: PRT
<213> ORGANISM: Artificial
<220> FEATURE:
<223> OTHER INFORMATION: Synthetic construct

<400> SEQUENCE: 136

Asn Ile Leu Tyr Ile Ser Gly Ser Asn Val Trp Asp Tyr
1               5                   10

<210> SEQ ID NO 137
<211> LENGTH: 378
<212> TYPE: DNA
<213> ORGANISM: Artificial
<220> FEATURE:
<223> OTHER INFORMATION: Synthetic construct

<400> SEQUENCE: 137
atggcctgga cccctctcct gctccccctc ctcactttct gcacagtctc tgaggcctcc    60
tctgagctga cacagccacc ctcggtgtca gtttccccag acaaacggc caggatcacc    120
tgctctggag atgttttgcc aaaaaaatat gcttattggt accaacagaa gtcaggccag    180
gcccctgtgc tggtcgtcta tgaggacacc aaacgaccct ccgggatccc tgagagattc    240
tctggctcca gctcagggac aatggccacc ttgactatca gtggggccca ggtgggtgat    300
gaaggtgact actactgtta ctcaacagac agtagtggta atttcttcgg tggagggacc    360
aagttgaccg tcctaggt                                                  378

<210> SEQ ID NO 138
<211> LENGTH: 126
<212> TYPE: PRT
<213> ORGANISM: Artificial
<220> FEATURE:
<223> OTHER INFORMATION: Synthetic construct

<400> SEQUENCE: 138

Met Ala Trp Thr Pro Leu Leu Pro Leu Leu Thr Phe Cys Thr Val
1               5                   10                  15

Ser Glu Ala Ser Ser Glu Leu Thr Gln Pro Pro Ser Val Ser Val Ser
                20                  25                  30

Pro Gly Gln Thr Ala Arg Ile Thr Cys Ser Gly Asp Val Leu Pro Lys
            35                  40                  45

Lys Tyr Ala Tyr Trp Tyr Gln Gln Lys Ser Gly Gln Ala Pro Val Leu
        50                  55                  60

Val Val Tyr Glu Asp Thr Lys Arg Pro Ser Gly Ile Pro Glu Arg Phe
65                  70                  75                  80

Ser Gly Ser Ser Ser Gly Thr Met Ala Thr Leu Thr Ile Ser Gly Ala
                85                  90                  95

Gln Val Gly Asp Glu Gly Asp Tyr Tyr Cys Tyr Ser Thr Asp Ser Ser
            100                 105                 110

Gly Asn Phe Phe Gly Gly Gly Thr Lys Leu Thr Val Leu Gly
        115                 120                 125

<210> SEQ ID NO 139
<211> LENGTH: 417
<212> TYPE: DNA
<213> ORGANISM: Artificial
<220> FEATURE:
<223> OTHER INFORMATION: Synthetic construct

<400> SEQUENCE: 139

```
atggagtctg ggctgagctg ggttttcctt gttgcaatct taaaaggtgt ccagtgtgag    60
gtgcaggtgg tggagtctgg gggaggcttg gtccagccgg gggggtccct gagactctcc   120
tgtgcagcct ctggattcac cgtcaatagc aaattcatga cctgggtccg ccaggctcca   180
gggacggggc tggagtgcgt ctcgattatt tataacgatg gcagcacata ctatgcagac   240
tctgtgaagg gccggttcac catctccaga gacaattcca agaacacgtt gtatcttcaa   300
atgaacaggc tgcgacctga ggacacggct gtgtattttt gtgcgagaag gcatttttc   360
gggggaaatg atgattttga tatctggggc caagggacac tggtcaccgt ctcttca      417
```

<210> SEQ ID NO 140
<211> LENGTH: 139
<212> TYPE: PRT
<213> ORGANISM: Artificial
<220> FEATURE:
<223> OTHER INFORMATION: Synthetic construct

<400> SEQUENCE: 140

```
Met Glu Ser Gly Leu Ser Trp Val Phe Leu Val Ala Ile Leu Lys Gly
1               5                   10                  15
Val Gln Cys Glu Val Gln Val Val Glu Ser Gly Gly Gly Leu Val Gln
                20                  25                  30
Pro Gly Gly Ser Leu Arg Leu Ser Cys Ala Ala Ser Gly Phe Thr Val
            35                  40                  45
Asn Ser Lys Phe Met Thr Trp Val Arg Gln Ala Pro Gly Thr Gly Leu
        50                  55                  60
Glu Cys Val Ser Ile Ile Tyr Asn Asp Gly Ser Thr Tyr Tyr Ala Asp
65                  70                  75                  80
Ser Val Lys Gly Arg Phe Thr Ile Ser Arg Asp Asn Ser Lys Asn Thr
                85                  90                  95
Leu Tyr Leu Gln Met Asn Arg Leu Arg Pro Glu Asp Thr Ala Val Tyr
            100                 105                 110
Phe Cys Ala Arg Arg Ala Phe Phe Gly Gly Asn Asp Asp Phe Asp Ile
        115                 120                 125
Trp Gly Gln Gly Thr Leu Val Thr Val Ser Ser
    130                 135
```

<210> SEQ ID NO 141
<211> LENGTH: 7
<212> TYPE: PRT
<213> ORGANISM: Artificial
<220> FEATURE:
<223> OTHER INFORMATION: Synthetic construct

<400> SEQUENCE: 141

```
Ile Tyr Asn Asp Gly Ser Thr
1               5
```

<210> SEQ ID NO 142
<211> LENGTH: 14
<212> TYPE: PRT

<213> ORGANISM: Artificial
<220> FEATURE:
<223> OTHER INFORMATION: Synthetic construct

<400> SEQUENCE: 142

```
Ala Arg Arg Ala Phe Phe Gly Gly Asn Asp Asp Phe Asp Ile
1               5                   10
```

<210> SEQ ID NO 143
<211> LENGTH: 384
<212> TYPE: DNA
<213> ORGANISM: Artificial
<220> FEATURE:
<223> OTHER INFORMATION: Synthetic construct

<400> SEQUENCE: 143

```
atggaaaccc cagcgcagct tctcttcctc ctgctactct ggctcccaga taccagcgga     60
gaaattgtgt tgacgcagtc tccaggcacc ctgtctttgt ctccagggga cagagccacc    120
ctctcctgca gggccggtca gagtgttagc agcagcttct tagcctggta ccaacagaga    180
cctggccagc tcccaggct cctcatctat ggtgcatcca gcagggccac tgacatccca    240
gacagattca gtggcagcgg gtctgggaca gacttcactc tcaccatcag cagactggag    300
cctgaagatt ttgcagtcta ttactgtcat cagtatagta gctcacttcc gacgttcggc    360
ccagggacca aggtggaaat caaa                                          384
```

<210> SEQ ID NO 144
<211> LENGTH: 128
<212> TYPE: PRT
<213> ORGANISM: Artificial
<220> FEATURE:
<223> OTHER INFORMATION: Synthetic construct

<400> SEQUENCE: 144

```
Met Glu Thr Pro Ala Gln Leu Leu Phe Leu Leu Leu Trp Leu Pro
1               5                   10                  15

Asp Thr Ser Gly Glu Ile Val Leu Thr Gln Ser Pro Gly Thr Leu Ser
                20                  25                  30

Leu Ser Pro Gly Asp Arg Ala Thr Leu Ser Cys Arg Ala Gly Gln Ser
            35                  40                  45

Val Ser Ser Ser Phe Leu Ala Trp Tyr Gln Gln Arg Pro Gly Gln Pro
        50                  55                  60

Pro Arg Leu Leu Ile Tyr Gly Ala Ser Ser Arg Ala Thr Asp Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys His Gln Tyr
            100                 105                 110

Ser Ser Ser Leu Pro Thr Phe Gly Pro Gly Thr Lys Val Glu Ile Lys
        115                 120                 125
```

<210> SEQ ID NO 145
<211> LENGTH: 7
<212> TYPE: PRT
<213> ORGANISM: Artificial
<220> FEATURE:
<223> OTHER INFORMATION: Synthetic construct

<400> SEQUENCE: 145

```
Gln Ser Val Ser Ser Ser Phe
1               5
```

```
<210> SEQ ID NO 146
<211> LENGTH: 4
<212> TYPE: PRT
<213> ORGANISM: Artificial
<220> FEATURE:
<223> OTHER INFORMATION: Synthetic construct

<400> SEQUENCE: 146

Gly Ala Ser Ser
1

<210> SEQ ID NO 147
<211> LENGTH: 435
<212> TYPE: DNA
<213> ORGANISM: Artificial
<220> FEATURE:
<223> OTHER INFORMATION: Synthetic construct

<400> SEQUENCE: 147
atggagtttg ggctgagctg gcttttctt gtggctattt taaaaggtgt ccagtgtgac      60
gtgcagctgg cggagtctgg gggaggcctg gtacaacccg gggattccct gacactctcc     120
tgtgcagcct ctggattcat ctttaacaat tatttcatga gttgggtccg ccagactcca     180
gggaaggggc tggagtgggt ctcaggatt agtgctaatg gtgagaggtc gatatacgca      240
gactccgtga agggccggtt caccatctcc agagacaatt ccaagaaaac agtgtctctc     300
caaatgaaca gcctgagcgc gaggacacg gccatatatt actgtgcgag agcgggctgt      360
gacagcacca gctgctatgc ccgagttggg tggttcggcc cctggggcca gggaatcctg     420
gtcaccgtct cctca                                                     435

<210> SEQ ID NO 148
<211> LENGTH: 145
<212> TYPE: PRT
<213> ORGANISM: Artificial
<220> FEATURE:
<223> OTHER INFORMATION: Synthetic construct

<400> SEQUENCE: 148

Met Glu Phe Gly Leu Ser Trp Leu Phe Leu Val Ala Ile Leu Lys Gly
1               5                   10                  15

Val Gln Cys Asp Val Gln Leu Ala Glu Ser Gly Gly Gly Leu Val Gln
            20                  25                  30

Pro Gly Asp Ser Leu Thr Leu Ser Cys Ala Ala Ser Gly Phe Ile Phe
        35                  40                  45

Asn Asn Tyr Phe Met Ser Trp Val Arg Gln Thr Pro Gly Lys Gly Leu
    50                  55                  60

Glu Trp Val Ser Gly Ile Ser Ala Asn Gly Glu Arg Ser Ile Tyr Ala
65                  70                  75                  80

Asp Ser Val Lys Gly Arg Phe Thr Ile Ser Arg Asp Asn Ser Lys Lys
                85                  90                  95

Thr Val Ser Leu Gln Met Asn Ser Leu Ser Ala Glu Asp Thr Ala Ile
            100                 105                 110

Tyr Tyr Cys Ala Arg Ala Gly Cys Asp Ser Thr Ser Cys Tyr Ala Arg
        115                 120                 125

Val Gly Trp Phe Gly Pro Trp Gly Gln Gly Ile Leu Val Thr Val Ser
    130                 135                 140

Ser
145
```

<210> SEQ ID NO 149
<211> LENGTH: 8
<212> TYPE: PRT
<213> ORGANISM: Artificial
<220> FEATURE:
<223> OTHER INFORMATION: Synthetic construct

<400> SEQUENCE: 149

Gly Phe Ile Phe Asn Asn Tyr Phe
1               5

<210> SEQ ID NO 150
<211> LENGTH: 8
<212> TYPE: PRT
<213> ORGANISM: Artificial
<220> FEATURE:
<223> OTHER INFORMATION: Synthetic construct

<400> SEQUENCE: 150

Ile Ser Ala Asn Gly Glu Arg Ser
1               5

<210> SEQ ID NO 151
<211> LENGTH: 19
<212> TYPE: PRT
<213> ORGANISM: Artificial
<220> FEATURE:
<223> OTHER INFORMATION: Synthetic construct

<400> SEQUENCE: 151

Ala Arg Ala Gly Cys Asp Ser Thr Ser Cys Tyr Ala Arg Val Gly Trp
1               5                   10                  15

Phe Gly Pro

<210> SEQ ID NO 152
<211> LENGTH: 399
<212> TYPE: DNA
<213> ORGANISM: Artificial
<220> FEATURE:
<223> OTHER INFORMATION: Synthetic construct

<400> SEQUENCE: 152
atggtgttgc agacccaggt cttcatttct ctgttgctct ggatctctgg tgcctacggg      60
gacgtcgtga tgacccagtc tccagactcc ctggctgtgt ctctgggcga gagggccacc     120
ctcaactgca gtccagaga gagtgtttta tacactacca acaacaggaa ctacttagct      180
tggtaccagc agaaaccagg acagcctcct aagctcctca tttactgggc atctacccgg     240
gagtctgggg tccctgaccg attcagcggc agcgggtctg ggacagattt ctctctcacc     300
atcagcagcc tgcaggctga agatgtggca gtttattact gtcagcaata tcttacaact     360
cctccgacgt cggccaggg gaccaaggta gaaatcaaa                             399

<210> SEQ ID NO 153
<211> LENGTH: 133
<212> TYPE: PRT
<213> ORGANISM: Artificial
<220> FEATURE:
<223> OTHER INFORMATION: Synthetic construct

<400> SEQUENCE: 153

Met Val Leu Gln Thr Gln Val Phe Ile Ser Leu Leu Leu Trp Ile Ser
1               5                   10                  15

Gly Ala Tyr Gly Asp Val Val Met Thr Gln Ser Pro Asp Ser Leu Ala
            20                  25                  30

Val Ser Leu Gly Glu Arg Ala Thr Leu Asn Cys Lys Ser Arg Glu Ser
        35                  40                  45

Val Leu Tyr Thr Thr Asn Asn Arg Asn Tyr Leu Ala Trp Tyr Gln Gln
    50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Ser Leu Thr Ile Ser Ser Leu Gln Ala Glu Asp Val Ala Val Tyr
            100                 105                 110

Tyr Cys Gln Gln Tyr Leu Thr Thr Pro Pro Thr Phe Gly Gln Gly Thr
        115                 120                 125

Lys Val Glu Ile Lys
    130

<210> SEQ ID NO 154
<211> LENGTH: 12
<212> TYPE: PRT
<213> ORGANISM: Artificial
<220> FEATURE:
<223> OTHER INFORMATION: Synthetic construct

<400> SEQUENCE: 154

Glu Ser Val Leu Tyr Thr Thr Asn Asn Arg Asn Tyr
1               5                   10

<210> SEQ ID NO 155
<211> LENGTH: 4
<212> TYPE: PRT
<213> ORGANISM: Artificial
<220> FEATURE:
<223> OTHER INFORMATION: Synthetic construct

<400> SEQUENCE: 155

Trp Ala Ser Thr
1

<210> SEQ ID NO 156
<211> LENGTH: 9
<212> TYPE: PRT
<213> ORGANISM: Artificial
<220> FEATURE:
<223> OTHER INFORMATION: Synthetic construct

<400> SEQUENCE: 156

Gln Gln Tyr Leu Thr Thr Pro Pro Thr
1               5

<210> SEQ ID NO 157
<211> LENGTH: 435
<212> TYPE: DNA
<213> ORGANISM: Artificial
<220> FEATURE:
<223> OTHER INFORMATION: Synthetic construct

<400> SEQUENCE: 157
atggagtttg ggctgagctg gcttttctt gcggctattt taaaaggtgt ccagtgtgag      60
gtgttgctgg tggagtctgg gggagacttg gtccagccgg gggggtccct gagactctcc    120
tgtgcagcct ctggattccc ctttagcaac tttgccatga actgggtccg ccaggctcca    180

```
gggaaggggc tggagtgggt ctcaagtatt agcgatactg gtcttaaaac atatgctgca    240
gactccgtga agggccggtt caccatctcc agagacagtt ccaagaacac ggtggatctg    300
gaaatgaaca gcctgagagt cgaagacacg gccgtatatt actgtgcaaa aacgggctgt    360
gacagtagaa gctgctatgc ccgaactggg tggttgggca cgtggggcca gggaaccctg    420
gtcatcgtct cctca                                                    435

<210> SEQ ID NO 158
<211> LENGTH: 145
<212> TYPE: PRT
<213> ORGANISM: Artificial
<220> FEATURE:
<223> OTHER INFORMATION: Synthetic construct

<400> SEQUENCE: 158

Met Glu Phe Gly Leu Ser Trp Leu Phe Leu Ala Ala Ile Leu Lys Gly
1               5                   10                  15

Val Gln Cys Glu Val Leu Leu Val Glu Ser Gly Gly Asp Leu Val Gln
            20                  25                  30

Pro Gly Gly Ser Leu Arg Leu Ser Cys Ala Ala Ser Gly Phe Pro Phe
        35                  40                  45

Ser Asn Phe Ala Met Asn Trp Val Arg Gln Ala Pro Gly Lys Gly Leu
    50                  55                  60

Glu Trp Val Ser Ser Ile Ser Asp Thr Gly Leu Lys Thr Tyr Ala Ala
65                  70                  75                  80

Asp Ser Val Lys Gly Arg Phe Thr Ile Ser Arg Asp Ser Ser Lys Asn
                85                  90                  95

Thr Val Asp Leu Glu Met Asn Ser Leu Arg Val Glu Asp Thr Ala Val
            100                 105                 110

Tyr Tyr Cys Ala Lys Thr Gly Cys Asp Ser Arg Ser Cys Tyr Ala Arg
        115                 120                 125

Thr Gly Trp Leu Gly Thr Trp Gly Gln Gly Thr Leu Val Ile Val Ser
    130                 135                 140

Ser
145

<210> SEQ ID NO 159
<211> LENGTH: 8
<212> TYPE: PRT
<213> ORGANISM: Artificial
<220> FEATURE:
<223> OTHER INFORMATION: Synthetic construct

<400> SEQUENCE: 159

Gly Phe Pro Phe Ser Asn Phe Ala
1               5

<210> SEQ ID NO 160
<211> LENGTH: 8
<212> TYPE: PRT
<213> ORGANISM: Artificial
<220> FEATURE:
<223> OTHER INFORMATION: Synthetic construct

<400> SEQUENCE: 160

Ile Ser Asp Thr Gly Leu Lys Thr
1               5

<210> SEQ ID NO 161
<211> LENGTH: 19
```

```
<212> TYPE: PRT
<213> ORGANISM: Artificial
<220> FEATURE:
<223> OTHER INFORMATION: Synthetic construct

<400> SEQUENCE: 161

Ala Lys Thr Gly Cys Asp Ser Arg Ser Cys Tyr Ala Arg Thr Gly Trp
1               5                   10                  15

Leu Gly Thr

<210> SEQ ID NO 162
<211> LENGTH: 393
<212> TYPE: DNA
<213> ORGANISM: Artificial
<220> FEATURE:
<223> OTHER INFORMATION: Synthetic construct

<400> SEQUENCE: 162
atggaagccc cagctcagct tctcttcctc ctgctactct ggctcccaga tatcaccgga      60
gaaattgtgt tgacacagtc tccagccacc ctgtctttgt ctcctgggga aagagccacc     120
ctctcctgtc gggccagtca gagtgttagc agctacttag cctggtacca acagaaacct     180
ggccaggctc ccaggctcct catttatgat gcatctaaga gggccactgg catcccagcc     240
aggttcagtg gcagtgggtc tgggacagac ttcactctca ccatcagcag cctagagcct     300
gaagattttg cagtttattt ctgtcagctg cgtagcaact ggcctccgca cgagagggtc     360
actttcggcc ctgggaccaa agtggatttc aaa                                  393

<210> SEQ ID NO 163
<211> LENGTH: 131
<212> TYPE: PRT
<213> ORGANISM: Artificial
<220> FEATURE:
<223> OTHER INFORMATION: Synthetic construct

<400> SEQUENCE: 163

Met Glu Ala Pro Ala Gln Leu Leu Phe Leu Leu Leu Leu Trp Leu Pro
1               5                   10                  15

Asp Ile Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Lys Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Phe Cys Gln Leu Arg Ser
            100                 105                 110

Asn Trp Pro Pro His Glu Arg Val Thr Phe Gly Pro Gly Thr Lys Val
        115                 120                 125

Asp Phe Lys
    130

<210> SEQ ID NO 164
<211> LENGTH: 14
<212> TYPE: PRT
<213> ORGANISM: Artificial
<220> FEATURE:
```

<223> OTHER INFORMATION: Synthetic construct

<400> SEQUENCE: 164

Gln Leu Arg Ser Asn Trp Pro Pro His Glu Arg Val Thr Phe
1               5                   10

<210> SEQ ID NO 165
<211> LENGTH: 426
<212> TYPE: DNA
<213> ORGANISM: Artificial
<220> FEATURE:
<223> OTHER INFORMATION: Synthetic construct

<400> SEQUENCE: 165

```
atggactgga cctggaggtt cctctttgtg gtggcagcag ctacaggtgt ccagtcccag      60
gtgcagctgg tgcagtctgg ggctgaggtg aagaagcctg gtcctcggt gaaggtctcc      120
tgcaaggctt ctggaggcac cttcgccaac tctggtgtcg cctgggtgcg acaggcccct     180
ggacaagggc ttgagtggat gggaggactc atccctgtct ttggtgcagc tgattacgca     240
cagaagttcc ggggcagact ctcgattacc gcggacgaat cttcgaccac agccttcatg     300
gagctcgata gcctgagatc tgacgacacg gccgtctatt actgtgcgaa agatcatttc     360
acctacaata agtactttag ttggttcgac ccctggggcc agggaaccct ggtcatcgtc     420
tcctca                                                                 426
```

<210> SEQ ID NO 166
<211> LENGTH: 142
<212> TYPE: PRT
<213> ORGANISM: Artificial
<220> FEATURE:
<223> OTHER INFORMATION: Synthetic construct

<400> SEQUENCE: 166

Met Asp Trp Thr Trp Arg Phe Leu Phe Val Val Ala Ala Ala Thr Gly
1               5                   10                  15

Val Gln Ser Gln Val Gln Leu Val Gln Ser Gly Ala Glu Val Lys Lys
            20                  25                  30

Pro Gly Ser Ser Val Lys Val Ser Cys Lys Ala Ser Gly Gly Thr Phe
        35                  40                  45

Ala Asn Ser Gly Val Ala Trp Val Arg Gln Ala Pro Gly Gln Gly Leu
    50                  55                  60

Glu Trp Met Gly Gly Leu Ile Pro Val Phe Gly Ala Ala Asp Tyr Ala
65                  70                  75                  80

Gln Lys Phe Arg Gly Arg Leu Ser Ile Thr Ala Asp Glu Ser Ser Thr
                85                  90                  95

Thr Ala Phe Met Glu Leu Asp Ser Leu Arg Ser Asp Asp Thr Ala Val
            100                 105                 110

Tyr Tyr Cys Ala Lys Asp His Phe Thr Tyr Asn Lys Tyr Phe Ser Trp
        115                 120                 125

Phe Asp Pro Trp Gly Gln Gly Thr Leu Val Ile Val Ser Ser
    130                 135                 140

<210> SEQ ID NO 167
<211> LENGTH: 8
<212> TYPE: PRT
<213> ORGANISM: Artificial
<220> FEATURE:
<223> OTHER INFORMATION: Synthetic construct

<400> SEQUENCE: 167

```
Gly Gly Thr Phe Ala Asn Ser Gly
1               5
```

<210> SEQ ID NO 168
<211> LENGTH: 8
<212> TYPE: PRT
<213> ORGANISM: Artificial
<220> FEATURE:
<223> OTHER INFORMATION: Synthetic construct

<400> SEQUENCE: 168

```
Leu Ile Pro Val Phe Gly Ala Ala
1               5
```

<210> SEQ ID NO 169
<211> LENGTH: 16
<212> TYPE: PRT
<213> ORGANISM: Artificial
<220> FEATURE:
<223> OTHER INFORMATION: Synthetic construct

<400> SEQUENCE: 169

```
Ala Lys Asp His Phe Thr Tyr Asn Lys Tyr Phe Ser Trp Phe Asp Pro
1               5                   10                  15
```

<210> SEQ ID NO 170
<211> LENGTH: 402
<212> TYPE: DNA
<213> ORGANISM: Artificial
<220> FEATURE:
<223> OTHER INFORMATION: Synthetic construct

<400> SEQUENCE: 170

```
atgagtgtcc ccaccatggc ctggatgatg cttctcctcg gactccttgc ttatggatca     60
ggagtggatt ctcagactgt ggtgacccag agccatcgt tgtcagtgtc ccctggaggg    120
acagtcactc tcacttgtgc cttgagctct ggctcagtct cgactagcta ctaccccagc    180
tggtaccaac agaccccgg ccaggctcca cgcacgctca tctacagtac aaatcttcgc    240
tcttctgggg tccctgatcg cttctccggc tccatccttg gaacaaagc tgccctcacc    300
atcacggggg cccaggcaga tgatgaatgt gattattatt gtgtactctt tatgggcagt    360
ggcatttcga tgttcggcgg agggaccaag ttgaccgtcc ta                        402
```

<210> SEQ ID NO 171
<211> LENGTH: 134
<212> TYPE: PRT
<213> ORGANISM: Artificial
<220> FEATURE:
<223> OTHER INFORMATION: Synthetic construct

<400> SEQUENCE: 171

```
Met Ser Val Pro Thr Met Ala Trp Met Met Leu Leu Leu Gly Leu Leu
1               5                   10                  15

Ala Tyr Gly Ser Gly Val Asp Ser Gln Thr Val Val Thr Gln Glu Pro
            20                  25                  30

Ser Leu Ser Val Ser Pro Gly Gly Thr Val Thr Leu Thr Cys Ala Leu
        35                  40                  45

Ser Ser Gly Ser Val Ser Thr Ser Tyr Tyr Pro Ser Trp Tyr Gln Gln
    50                  55                  60

Thr Pro Gly Gln Ala Pro Arg Thr Leu Ile Tyr Ser Thr Asn Leu Arg
65                  70                  75                  80
```

```
Ser Ser Gly Val Pro Asp Arg Phe Ser Gly Ser Ile Leu Gly Asn Lys
                85                  90                  95

Ala Ala Leu Thr Ile Thr Gly Ala Gln Ala Asp Asp Glu Cys Asp Tyr
            100                 105                 110

Tyr Cys Val Leu Phe Met Gly Ser Gly Ile Ser Met Phe Gly Gly Gly
        115                 120                 125

Thr Lys Leu Thr Val Leu
        130

<210> SEQ ID NO 172
<211> LENGTH: 9
<212> TYPE: PRT
<213> ORGANISM: Artificial
<220> FEATURE:
<223> OTHER INFORMATION: Synthetic construct

<400> SEQUENCE: 172

Ser Gly Ser Val Ser Thr Ser Tyr Tyr
1               5

<210> SEQ ID NO 173
<211> LENGTH: 4
<212> TYPE: PRT
<213> ORGANISM: Artificial
<220> FEATURE:
<223> OTHER INFORMATION: Synthetic construct

<400> SEQUENCE: 173

Ser Thr Asn Leu
1

<210> SEQ ID NO 174
<211> LENGTH: 10
<212> TYPE: PRT
<213> ORGANISM: Artificial
<220> FEATURE:
<223> OTHER INFORMATION: Synthetic construct

<400> SEQUENCE: 174

Val Leu Phe Met Gly Ser Gly Ile Ser Met
1               5                   10

<210> SEQ ID NO 175
<211> LENGTH: 414
<212> TYPE: DNA
<213> ORGANISM: Artificial
<220> FEATURE:
<223> OTHER INFORMATION: Synthetic construct

<400> SEQUENCE: 175
atggactgga cctggaggat cctcttcttg gtggcggcag ccacaggtgt ccactcccag    60
gtgcagctgg tgcagtctgg ggctgaggtg acgaagcctg ggcctcagt gaaggtctcc   120 tgcaaggctt caggatacac cttcaccgaa tactatatgc actgggtgcg acaggcccct   180
ggacaaggcc ttgagtggat gggacggatc aaccctaaca gtggtggcac aaagtatgca   240
cagaaatttc agggcagggt caccatgact cgggacacga ccatcagtac agtctacatg   300
gagctgacca cgcccctatc tgacgacacg gccgtatatt cctgtgtgag ggccgataat   360
aatggttata cttacactta ctggggccag ggaaccctgg tcaccgtctc ttca         414

<210> SEQ ID NO 176
<211> LENGTH: 6
<212> TYPE: PRT
```

-continued

```
<213> ORGANISM: Artificial
<220> FEATURE:
<223> OTHER INFORMATION: Synthetic construct

<400> SEQUENCE: 176

Val Leu Pro Lys Lys Tyr
1               5

<210> SEQ ID NO 177
<211> LENGTH: 4
<212> TYPE: PRT
<213> ORGANISM: Artificial
<220> FEATURE:
<223> OTHER INFORMATION: Synthetic construct

<400> SEQUENCE: 177

Glu Asp Thr Lys
1

<210> SEQ ID NO 178
<211> LENGTH: 9
<212> TYPE: PRT
<213> ORGANISM: Artificial
<220> FEATURE:
<223> OTHER INFORMATION: Synthetic construct

<400> SEQUENCE: 178

Tyr Ser Thr Asp Ser Ser Gly Asn Phe
1               5

<210> SEQ ID NO 179
<211> LENGTH: 328
<212> TYPE: PRT
<213> ORGANISM: Artificial
<220> FEATURE:
<223> OTHER INFORMATION: Synthetic construct

<400> SEQUENCE: 179

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Leu Gly Thr Gln Thr Tyr
65                  70                  75                  80

Ile Cys Asn Val Asn His Lys Pro Ser Asn Thr Lys Val Asp Lys Lys
                85                  90                  95

Val Glu Pro Lys Ser Cys Asp Lys Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160
```

```
Val Asp Gly Val Glu Val His Asn Ala Lys Thr Lys Pro Arg Glu Glu
            165             170              175

Gln Tyr Asn Ser Thr Tyr Arg Val Val Ser Val Leu Thr Val Leu His
            180             185              190

Gln Asp Trp Leu Asn Gly Lys Glu Tyr Lys Cys Lys Val Ser Asn Lys
            195             200              205

Ala Leu Pro Ala Pro Ile Glu Lys Thr Ile Ser Lys Ala Lys Gly Gln
            210             215              220

Pro Arg Glu Pro Gln Val Tyr Thr Leu Pro Pro Ser Arg Asp Glu Leu
225             230             235              240

Thr Lys Asn Gln Val Ser Leu Thr Cys Leu Val Lys Gly Phe Tyr Pro
            245             250              255

Ser Asp Ile Ala Val Glu Trp Glu Ser Asn Gly Gln Pro Glu Asn Asn
            260             265              270

Tyr Lys Thr Thr Pro Pro Val Leu Asp Ser Asp Gly Ser Phe Phe Leu
            275             280              285

Tyr Ser Lys Leu Thr Val Asp Lys Ser Arg Trp Gln Gln Gly Asn Val
            290             295              300

Phe Ser Cys Ser Val Met His Glu Ala Leu His Asn His Tyr Thr Gln
305             310             315              320

Lys Ser Leu Ser Leu Ser Pro Gly
            325
```

HPV PROTEINS, ANTIBODIES, AND USES IN MANAGING ABNORMAL EPITHELIAL CELL GROWTH

CROSS-REFERENCE TO RELATED APPLICATIONS

This application is the National Stage of International Application No. PCT/US2019/018798 filed Feb. 20, 2019, which claims the benefit of U.S. Provisional Application No. 62/632,777 filed Feb. 20, 2018. The entirety of each of these applications is hereby incorporated by reference for all purposes.

STATEMENT REGARDING FEDERALLY SPONSORED RESEARCH OR DEVELOPMENT

This invention was made with government support under 5U19AI057266-14 awarded by the National Institutes of Health. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy and is hereby incorporated by reference into the specification. The name of the text file containing the Sequence Listing is 18001PCT_ST25.txt. The text file is 93,048 bytes, was created on Feb. 20, 2019, and is being submitted electronically via EFS-Web.

BACKGROUND

Human papillomaviruses (HPV) are small circular, double-stranded DNA viruses that infect epithelial tissues. HPV strains can be spread by direct skin-to-skin contact including oral contact and sexual intercourse. HPV infections have been linked to warts and can be a risk factor in the eventual development of a variety of epithelial tissue-based cancers such as cervical cancer in women. HPV types typically fall into low-risk and high-risk HPVs for causing cancer. For example, HPV types 6 and 11 cause warts. They are considered low-risk for causing cancer. On the other hand, HPV types 16 and 18 are consider high-risk. See Thomas et al. Oncogene. 2008, 27(55):7018-30 and Ruttkay-Nedecky et al. Int J Oncol. 2013, 43(6):1754-62.

Prophylactic HPV vaccines are currently available. However, these vaccines are not effective for treating existing established HPV infection. Thus, there is a need to identify improved methods for treating or preventing HPV-related diseases for infected individuals. See e.g., U.S. Pat. No. 8,420,103, US Published Application Nos. US2009/0312527, US2001/0034021, US2017/0028052, and WO2015149051.

Bechtold et al. report human papillomavirus 16 E2 protein has no effect on transcription from episomal viral DNA. J Virol, 2003, 77(3):2021-2028.

Paolini et al. report human papillomavirus 16 E2 interacts with neuregulin receptor degradation protein 1 affecting ErbB-3 expression in vitro and in clinical samples of cervical lesions. Eur J Cancer, 2016, 58:52-61.

Several clinical trials using HPV E6 and E7 specific T cells are reported. ClinicalTrials.gov Identifier: NCT02379520.

References cited herein are not an admission of prior art.

SUMMARY

This disclosure relates to HPV proteins, antibodies, and uses in managing abnormal epithelial cell growth. In certain embodiments, this disclosure relates to detecting an HPV protein in a sample and correlating the presence as an indication that a subject is at risk of developing an HPV-related disease or condition. In certain embodiments, the HPV protein is E2 and/or E6. In certain embodiments, this disclosure relates to vaccinating or treating a subject for an HPV infection or related condition optionally in combination with immune-checkpoint inhibitors. In certain embodiments, this disclosure relates to HPV protein specific antibodies and binding agents for uses reported herein.

In certain embodiments, this disclosure relates to methods of detecting HPV-infected cells comprising: obtaining a sample of human epithelial tissue from a subject and detecting an HPV protein in the epithelial tissue or a malignancy or pre-malignancy inside the epithelial tissue indicating an HPV infection. In certain embodiments, the HPV protein is E2 and/or E6. In certain embodiments, the subject is diagnosed with a malignancy or pre-malignancy in the epithelial tissue. In certain embodiments, the subject is not diagnosed with a malignancy or pre-malignancy in the epithelial tissue. In certain embodiments, the subject is diagnosed with genital warts. In certain embodiments, the subject is diagnosed with atypical squamous cells of undetermined significance. In certain embodiments, the sample does or does not comprise a malignancy or pre-malignancy inside the epithelial tissue. In certain embodiments, intact HPV virions are or are not found in the upper layers of the squamous epithelial tissue.

In certain embodiments, the samples are obtained from the surface of the skin or mucosal surfaces such as vagina, cervix, vulva, area around the outside of the vagina, anus, inner foreskin, urethra of the penis, inner lining of the nose, mouth, throat, trachea, and bronchi or inner eyelids.

In certain embodiments, this disclosure relates to methods of treating or preventing cancer in a subject comprising administering an effective amount of an anti-viral agent or anti-HPV therapy to the subject diagnosed as at risk of developing cancer. In certain embodiments, the anti-viral agent or anti-HPV therapy is a specific binding agent or antibody that binds an HPV protein, or other HPV protein, ranpirnase, imiquimod, carrageenan, and/or a chemotherapy agent. In certain embodiments, the HPV protein is E2 and/or E6.

In certain embodiments, this disclosure relates to methods for diagnosing and treating or preventing cancer in a subject comprising: obtaining a sample of human epithelial tissue from a subject, and detecting an HPV protein in the epithelial tissue or a malignancy or pre-malignancy inside the epithelial tissue; diagnosing the subject as a subject at risk of developing cancer, and administering an effective amount of an anti-viral agent, anti-HPV therapy, or a specific binding agent or antibody that binds the HPV protein to the subject diagnosed as at risk of developing cancer. In certain embodiments, the HPV protein is E2 and/or E6.

In certain embodiments, this disclosure contemplates the use of an HPV protein in a cellular immunotherapy. In certain embodiments, this disclosure relates to methods of vaccinating for HPV comprising administering the HPV protein or a vector comprising a nucleic acid encoding the HPV protein to a subject in an effective amount to vaccinate the subject. In certain embodiments, the HPV protein is E2 and/or E6. In certain embodiments, the HPV protein vaccine, protein or nucleic acid, is administered in combination with an anti-CTLA4 and/or anti-PD1/PD-L1 antibody.

In certain embodiments, this disclosure relates to methods of treating cancer comprising administering an effective amount of an antibody that binds HPV E2 or other HPV protein to a subject at risk of or diagnosed with HPV. In certain embodiments, the HPV protein-specific antibody is administered in combination with an anti-CTLA4 and/or anti-PD1/PD-L1 antibody. In certain embodiments, the HPV protein is E2 and/or E6.

In certain embodiments, this disclosure relates to methods of treating cancer comprising administering an effective amount of an antibody reported herein to a subject at risk of or diagnosed with HPV.

In certain embodiments, this disclosure relates to methods of treating or preventing cancer comprising: removing T cells from the blood of a subject; replicating the T cells outside the body providing replicated T cells; exposing the replicated T cells to antigen presenting cells presenting HPV protein derived peptides on the surface of the cells providing the HPV protein activated T cells; and administering the HPV protein activated T cells to the subject in need thereof. In certain embodiments, the HPV protein is E2 and/or E6. In certain embodiments, the HPV protein activated T cells are administered in combination with IL-2. In certain embodiments, the HPV protein activated T cells are administered in combination with an anti-CTLA4 and/or anti-PD1/PD-L1 antibody.

In certain embodiments, this disclosure relates to methods of treating or preventing cancer comprising: removing T cells from the blood of a subject; replicating the T cells outside the body providing replicated T cells; exposing the replicated T cells to a vector for expressing an a chimeric antigen receptor on the surface of the cells, wherein the chimeric antigen receptor binds to an HPV protein providing HPV protein targeted T-cells; and administering HPV protein targeted T cells to the subject in need thereof. In certain embodiments, the HPV protein is E2 and/or E6. In certain embodiments, the HPV protein targeted T cells are administered in combination with IL-2. In certain embodiments, the HPV protein is E2 and/or E6. In certain embodiments, the HPV E2 targeted T cells are administered in combination with an anti-CTLA4 and/or anti-PD1/PD-L1 antibody.

In certain embodiments, the immune-checkpoint inhibitors are anti-CTLA4 (e.g., ipilimumab, tremelimumab) antibodies and/or anti-PD1/PD-L1 (e.g., nivolumab, pidilizumab, pembrolizumab, atezolizumab, avelumab, durvalumab) antibodies.

In certain embodiments, the disclosure contemplates using methods disclosed herein in combination with surgical removal of malignant or pre-malignant cells, radiation, and chemotherapy.

In certain embodiments, this disclosure relates to antibodies reported herein and HPV protein binding fragments thereof. In certain embodiments, this disclosure relates to vaccine and pharmaceutical compositions comprising antibodies reported herein and HPV protein binding fragments thereof and pharmaceutically acceptable excipients.

In certain embodiments, this disclosure relates to chimeric antibodies that bind HPV16 E2 protein. In certain embodiments, the chimeric antibodies are selected from 22-1B10, 22-E2A2, 22-E2B2, 22-E2B8, 22-E2B9, 22-E2C5, 22-E2C9, 22-E2C11, 22-E2D4, 22-E2E7, 22-E2F7, 22-E2F10, and 22-E2G5.

In certain embodiments, this disclosure relates to chimeric antibodies that bind HPV16 E6 protein. In certain embodiments, the chimeric antibodies are selected from 21-1E2, 21-1E11, and 21-1H3.

In certain embodiments, this disclosure relates to chimeric antibodies or antigen binding fragments comprising six complementarity determining regions (CDRs) thereof, wherein the CDRs comprise the three light chain CDRs derived from an antibody selected from 21-1E2, 21-1E11, 21-1H3, 22-1B10, 22-E2A2, 22-E2B2, 22-E2B8, 22-E2B9, 22-E2C5, 22-E2C9, 22-E2C11, 22-E2D4, 22-E2E7, 22-E2F7, 22-E2F10, and 22-E2G5, and wherein the CDRs comprise the three heavy chain CDRs derived from an antibody selected from 21-1E2, 21-1E11, 21-1H3, 22-1B10, 22-E2A2, 22-E2B2, 22-E2B8, 22-E2B9, 22-E2C5, 22-E2C9, 22-E2C11, 22-E2D4, 22-E2E7, 22-E2F7, 22-E2F10, and 22-E2G5, and wherein the antibody or antigen binding fragment thereof specifically binds to an epitope of an HPV protein. In certain embodiments, the HPV protein is E2 and/or E6.

In certain embodiments, this disclosure relates to chimeric antibodies or antigen binding fragments comprising complementarity determining regions 3 (CDR3) of the heavy chain derived from an antibody selected from 21-1E2, 21-1E11, 21-1H3, 22-1B10, 22-E2A2, 22-E2B2, 22-E2B8, 22-E2B9, 22-E2C5, 22-E2C9, 22-E2C11, 22-E2D4, 22-E2E7, 22-E2F7, 22-E2F10 wherein the antibody or antigen binding fragment thereof specifically binds to an epitope of an HPV protein. In certain embodiments, the HPV protein is E2 and/or E6.

DETAILED DISCUSSION

Figure 1A:
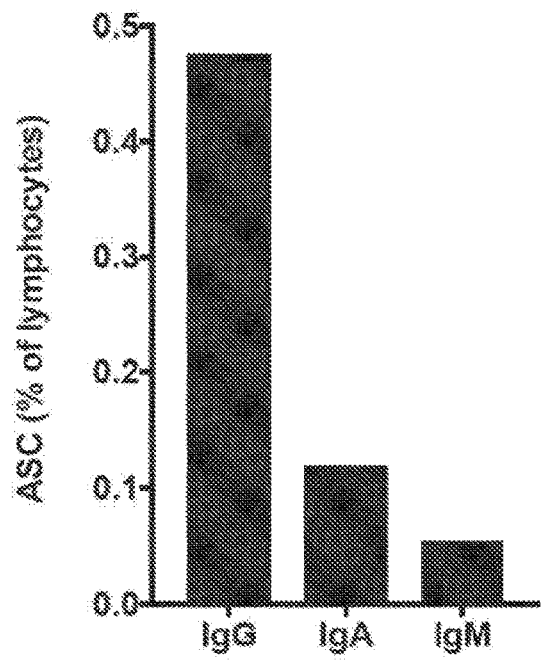
FIG. 1A shows data on the isotype profile of total antibody-secreting cells (ASCs) in the tumor-containing lymph node of a representative p16+ HNSCC patient.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

As used in this disclosure and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") have the meaning ascribed to them in U.S. Patent law in that they are inclusive or open-ended and do not exclude additional, unrecited elements or method steps. The term "comprising" in reference to a peptide having an amino acid sequence refers a peptide that may contain additional N-terminal (amine end) or C-terminal (carboxylic acid end) amino acids, i.e., the term is intended to include the amino acid sequence within a larger peptide. "Consisting essentially of" or "consists of" or the like, when applied to methods and compositions encompassed by the present disclosure refers to compositions like those disclosed herein that exclude certain prior art elements to provide an inventive feature of a claim, but which may contain additional composition components or method steps composition components or method steps, etc., that do not materially affect the basic and novel characteristic(s) of the compositions or methods, compared to those of the corresponding compositions or methods disclosed herein. The term "consisting of" in reference to a peptide having an amino acid sequence refers a peptide having the exact number of amino acids in the sequence and not more or having not more than a rage of amino acids expressly specified in the claim.

As used herein a "sample" refers to a composition taken from or originating from a subject. Examples of samples include cell samples, blood samples, tissue samples, hair samples, semen, and urine or excrement samples.

As used herein, a sample of "human epithelial tissue" is intended to include normal epithelial tissue and intended to include human epithelial tissue containing a malignancy or pre-malignancy inside the epithelial tissue and intended to include a malignancy or pre-malignancy derived from being in contact with the epithelial tissue.

The term "adjuvant" as used herein, generally means a substance that is added to the vaccine to increase the body's immune response to the vaccine. Adjuvants are inorganic or organic chemicals, macromolecules or entire cells of certain killed bacteria, which enhance the immune response to an antigen. They may be included in a vaccine to enhance the recipient's immune response to the supplied antigen, thus minimizing the amount of injected foreign material. In some embodiments, the adjuvants used in the methods of the present disclosure include alum, aluminum hydroxide, aluminum phosphate, calcium phosphate hydroxide, squalene, and toll-like receptor (TLR) ligands. In addition to imiquimod, other the TLR4 agonists are monophosphoryl lipid A (MPL), and the TLR2/4 agonist *bacillus* Calmette-Guerin (BCG). The TLR7/8 agonist, resiquimod, which is an imidazoquinoline like imiquimod, is also a contemplated adjuvant.

The terms "protein" and "polypeptide" refer to compounds comprising amino acids joined via peptide bonds and are used interchangeably. Amino acids may be naturally or non-naturally occurring. A "chimeric protein" or "fusion protein" is a molecule in which different portions of the protein are derived from different origins such that the entire molecule is not naturally occurring. A chimeric protein may contain amino acid sequences from the same species of different species as long as they are not arranged together in the same way that they exist in a natural state. Examples of a chimeric protein include sequences disclosed herein that contain one, two, or more amino acids attached to the C-terminal or N-terminal end that are not identical to any naturally occurring protein, such as in the case of adding an amino acid containing an amine side chain group, e.g., lysine, or an amino acid containing a carboxylic acid side chain group such as aspartic acid or glutamic acid, or a polyhistidine tag, e.g. typically four or more histidine amino acids. Contemplated chimeric proteins include those with self-cleaving peptides such as P2A-GSG. See Wang. Scientific Reports 5, Article number: 16273 (2015).

A "variant" refers to a chemically similar sequence because of amino acid changes or chemical derivative thereof. In certain embodiments, a variant contains one, two, or more amino acid deletions or substitutions. In certain embodiments, the substitutions are conserved substitutions. In certain embodiments, a variant contains one, two, or ten or more amino acid additions. The variant may be substituted with one or more chemical substituents.

One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs, for example, DNAStar software. Variants can be tested in functional assays. Certain variants have less than 10%, and preferably less than 5%, and still more preferably less than 2% changes (whether substitutions, deletions, and so on).

In certain embodiments, term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity.

In certain embodiments, sequence "identity" refers to the number of exactly matching amino acids (expressed as a percentage) in a sequence alignment between two sequences of the alignment calculated using the number of identical positions divided by the greater of the shortest sequence or the number of equivalent positions excluding overhangs wherein internal gaps are counted as an equivalent position. For example, the polypeptides GGGGGG and GGGGT have a sequence identity of 4 out of 5 or 80%. For example, the polypeptides GGGPPP and GGGAPPP have a sequence identity of 6 out of 7 or 85%. In certain embodiments, any recitation of sequence identity expressed herein may be substituted for sequence similarity. Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic—F Y W; hydrophobic—A V I L; Charged positive: R K H; Charged negative—D E; Polar—S T N Q. The amino acid groups are also considered conserved substitutions.

A "label" refers to a detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "label receptor" refers to incorporation of a heterologous polypeptide in the receptor. A label includes the incorporation of a radiolabeled amino acid or the covalent attachment of biotinyl moieties to a polypeptide that can be detected by marked avidin (for example, streptavidin containing a fluorescent marker or enzymatic activity that can be detected by optical or colorimetric methods). Examples of labels for polypeptides include, but are not limited to, the following: radioisotopes or radionucleotides (such as $^{18}$F, $^{35}$S, or $^{131}$I) fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

In certain embodiments, the disclosure relates to antibodies and antigen binding fragments comprising sequences disclosed herein or variants or fusions thereof wherein the amino terminal end or the carbon terminal end of the amino acid sequence are optionally attached to a heterologous amino acid sequence, label, or reporter molecule.

In certain embodiments, the disclosure relates to vectors comprising a nucleic acid encoding an antibody or antigen binding fragment disclosed herein or chimeric protein thereof. In certain embodiments, this disclosure relates to expression systems, e.g., in vitro or in vivo cells, comprising a nucleic acid or vector encoding an antibody or antigen binding fragment disclosed herein or chimeric protein thereof.

In certain embodiments, the vector optionally comprises a mammalian, human, insect, viral, bacterial, bacterial plasmid, yeast associated origin of replication or gene such as a gene or retroviral gene or lentiviral LTR, TAR, RRE, PE, SLIP, CRS, and INS nucleotide segment or gene selected from tat, rev, nef, vif, vpr, vpu, and vpx or structural genes selected from gag, pol, and env.

In certain embodiments, the vector optionally comprises a gene vector element (nucleic acid) such as a selectable marker region, lac operon, a CMV promoter, a hybrid chicken B-actin/CMV enhancer (CAG) promoter, tac promoter, T7 RNA polymerase promoter, SP6 RNA polymerase promoter, SV40 promoter, internal ribosome entry site (IRES) sequence, cis-acting woodchuck post regulatory element (WPRE), scaffold-attachment region (SAR), inverted terminal repeats (ITR), FLAG tag coding region, c-myc tag coding region, metal affinity tag coding region, streptavidin binding peptide tag coding region, polyHis tag coding region, HA tag coding region, MBP tag coding region, GST tag coding region, polyadenylation coding region, SV40 polyadenylation signal, SV40 origin of replication, Col E1 origin of replication, f1 origin, pBR322 origin, or pUC origin, TEV protease recognition site, loxP site, Cre recombinase coding region, or a multiple cloning site such as having 5, 6, or 7 or more restriction sites within a continuous segment of less than 50 or 60 nucleotides or having 3 or 4 or more restriction sites with a continuous segment of less than 20 or 30 nucleotides.

A "specific binding agent" may be a protein, peptide, nucleic acid, carbohydrate, lipid, or small molecular weight compound that specifically binds to an HPV protein. In certain embodiments, the HPV protein is E2 and/or E6. In a preferred embodiment, the specific binding agent according to the present disclosure is an antibody or binding fragment thereof (e.g., Fab, F(ab')$_2$), peptide or binding fragments thereof. WO00/24782 and WO03/057134 (incorporated herein by reference) describe and teach making binding agents that contain a randomly generated peptide which binds a desired target. A specific binding agent can be a proteinaceous polymeric molecule (a "large molecule") such as an antibody or Fc-peptide fusion, or a non-proteinaceous non-polymeric molecule typically having a molecular weight of less than about 1200 Daltons (a "small molecule").

The term "specifically binds" refers to the ability of a specific binding agent of the present disclosure, under specific binding conditions, to bind a target molecule such that its affinity is at least 10 times as great, but optionally 50 times as great, 100, 250 or 500 times as great, or even at least 1000 times as great as the average affinity of the same specific binding agent to a large collection of random peptides or polypeptides. A specific binding agent need not bind exclusively to a single target molecule but may specifically bind to a non-target molecule due to similarity in structural conformation between the target and non-target (e.g., paralogs or orthologs). Those of skill will recognize that specific binding to a molecule having the same function in a different species of animal (i.e., ortholog) or to a molecule having a substantially similar epitope as the target molecule (e.g., a paralog) is within the scope of the term "specific binding" which is determined relative to a statistically valid sampling of unique non-targets (e.g., random polypeptides).

As used herein, "subject" refers to any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity is reduced.

As used herein, the terms "treat" and "treating" are not limited to the case where the subject (e.g. patient) is cured and the disease is eradicated. Rather, embodiments of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

A "chemotherapy agent," "chemotherapeutic," "anti-cancer agent" or the like, refer to molecules that are recognized to aid in the treatment of a cancer. Contemplated examples include the following molecules or derivatives such as alemtuzumab, trastuzumab, ibritumomab tiuxetan, brentuximab vedotin, temozolomide, ado-trastuzumab emtansine, denileukin diftitox, blinatumomab, interferon alpha, aldesleukin, carmustine, bevacizumab, procarbazine, lomustine, vincristine, gefitinib, erlotinib, cisplatin, carboplatin, oxaliplatin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin, mithramycin, vinblastine, vindesine, vinorelbine, paclitaxel, taxol, docetaxel, etoposide, teniposide, amsacrine, topotecan, camptothecin, bortezomib, anagrelide, tamoxifen, toremifene, raloxifene, droloxifene, fulvestrant, bicalutamide, flutamide, nilutamide, cyproterone, goserelin, leuprorelin, buserelin, megestrol, anastrozole, letrozole, vorozole, exemestane, finasteride, marimastat, trastuzumab, cetuximab, dasatinib, imatinib, combretastatin, thalidomide, azacitidine, azathioprine, capecitabine, chlorambucil, cyclophosphamide, cytarabine, daunorubicin, doxifluridine, epothilone, irinotecan, mechlorethamine, mercaptopurine, mitoxantrone, pemetrexed, tioguanine, valrubicin, rituximab, and/or lenalidomide or combinations thereof such as cyclophosphamide, methotrexate, 5-fluorouracil (CMF); doxorubicin, cyclophosphamide (AC); mustine, vincristine, procarbazine, prednisolone (MOPP); adriamycin, bleomycin, vinblastine, dacarbazine (ABVD); cyclophosphamide, doxorubicin, vincristine, prednisolone (CHOP); rituximab, cyclophosphamide, doxorubicin, vincristine, prednisolone (RCHOP); bleomycin, etoposide, cisplatin (BEP); epirubicin, cisplatin, 5-fluorouracil (ECF); epirubicin, cisplatin, capecitabine (ECX); methotrexate, vincristine, doxorubicin, cisplatin (MVAC).

As used herein, the term "antibody" is intended to denote an immunoglobulin molecule that possesses a "variable region" antigen recognition site. The term "variable region" is intended to distinguish such domain of the immunoglobulin from domains that are broadly shared by antibodies (such as an antibody Fc domain). The variable region comprises a "hypervariable region" whose residues are responsible for antigen binding. The hypervariable region comprises amino acid residues from a "Complementarity Determining Region" or "CDR" (i.e., typically at approximately residues 24-34 (L1), 50-56 (L2) and 89-97 (L3) in the light chain variable domain and at approximately residues 27-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, J. Mol. Biol. 196:901-917). "Framework Region" or "FR" residues are those variable domain residues other than the hypervariable region residues as herein defined. The term antibody includes monoclonal antibodies, multi-specific antibodies, human antibodies, humanized antibodies, synthetic antibodies, chimeric antibodies, camelized antibodies (See e.g., Muyldermans et al., 2001, Trends Biochem. Sci. 26:230; Nuttall et al., 2000, Cur. Pharm. Biotech. 1:253; Reichmann and Muyldermans, 1999, J. Immunol. Meth. 231:25; International Publication Nos. WO 94/04678 and WO 94/25591; U.S. Pat. No. 6,005,079), single-chain Fvs (scFv) (see, e.g., see Pluckthun in The Pharmacology of Monoclonal Antibodies, vol. 113, Rosenburg and Moore eds. Springer-Verlag, New York, pp. 269-315 (1994)), single chain antibodies, disulfide-linked Fvs (sdFv), intrabodies, and anti-idiotypic (anti-Id) antibodies (including, e.g., anti-Id and anti-anti-Id antibodies to the disclosed B7-H5 antibodies). In particular, such antibodies include immunoglobulin molecules of any type (e.g., IgG, IgE, IgM, IgD, IgA and IgY), class (e.g., IgG1, IgG2, IgG3, IgG4, IgA1 and IgA2) or subclass.

As used herein, the term "antigen binding fragment" of an antibody refers to one or more portions of an antibody that contain the antibody's Complementarity Determining Regions ("CDRs") and optionally the framework residues that comprise the antibody's "variable region" antigen recognition site and exhibit an ability to immunospecifically bind an antigen. Such fragments include Fab', F(ab')2, Fv, single chain (ScFv), and mutants thereof, naturally occurring variants, and fusion proteins comprising the antibody's "variable region" antigen recognition site and a heterologous protein (e.g., a toxin, an antigen recognition site for a different antigen, an enzyme, a receptor or receptor ligand, etc.). As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino acid residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

Human, non-naturally occurring chimeric or humanized derivatives of anti-HPV protein antibodies are particularly preferred for in vivo use in humans, however, murine antibodies or antibodies of other species may be advantageously employed for many uses (for example, in vitro or in situ detection assays, acute in vivo use, etc.). A humanized antibody may comprise amino acid residue substitutions, deletions or additions in one or more non-human CDRs. The humanized antibody derivative may have substantially the same binding, stronger binding or weaker binding when compared to a non-derivative humanized antibody. In specific embodiments, one, two, three, four, or five amino acid residues of the CDR have been substituted, deleted or added (i.e., mutated). Completely human antibodies are particularly desirable for therapeutic treatment of human subjects.

Human antibodies can be made by a variety of methods including phage display methods described using antibody libraries derived from human immunoglobulin sequences (see U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741). Human antibodies can be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized using conventional methodologies with a selected antigen.

Monoclonal antibodies directed against the antigen can be obtained from the immunized, transgenic mice using conventional hybridoma technology (see, e.g., U.S. Pat. No. 5,916,771). The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM, and IgE antibodies. For an overview of this technology for producing human antibodies, see Lonberg and Huszar (1995, Int. Rev. Immunol. 13:65-93, which is incorporated herein by reference in its entirety). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661, 016, 5,545,806, 5,814,318, and 5,939,598, which are incorporated by reference herein in their entirety. In addition, companies such as Abgenix, Inc. (Freemont, Calif.) and Medarex (Princeton, N.J.) can be engaged to provide human antibodies directed against a selected antigen using technology similar to that described above.

A "chimeric antibody" is a molecule in which different portions of the antibody are derived from different immunoglobulin molecules such that the entire molecule is not naturally occurring. Examples of chimeric antibodies include those having a variable region derived from a non-human antibody and a human immunoglobulin constant region. The term is also intended to include antibodies having a variable region derived from one human antibody grafted to an immunoglobulin constant region of a predetermined sequence, or the constant region from another human for which there are allotypic differences residing in the constant regions of any naturally occurring antibody having the variable regions, e.g., CDRs 1, 2, and 3 of the light and heavy chain. Human heavy chain genes exhibit structural polymorphism (allotypes) that are inherited as a haplotype. The serologically defined allotypes differ within and between population groups. See Jefferis et al. mAb, 1 (2009), pp. 332-338.

Smith et al. report a protocol for the production of antigen-specific chimeric human monoclonal antibodies (hmAbs) wherein antibody-secreting cells (ASCs) are isolated from whole blood collected after vaccination and sorted by flow cytometry into single cell plates. Nat Protoc. 2009; 4(3):372-84. The antibody genes of the ASCs are then amplified by RT-PCR and nested PCR, cloned into expression vectors and transfected into a human cell line. Meijer et al. report methods for isolation of human antibody repertoires with preservation of the natural heavy and light chain pairing. J Mol Biol. 2006, 358(3):764-72. Wrammert et al. report using immunoglobulin variable regions isolated from sorted single ASCs to produce human monoclonal antibodies (mAbs) that bound with high affinity. Nature. 2008, 453(7195): 667-671.

Chimeric antibodies comprising one or more CDRs from a non-human species and framework regions from a human immunoglobulin molecule can be produced using a variety of techniques including, for example, CDR-grafting (EP 239,400; International Publication No. WO 91/09967; and U.S. Pat. Nos. 5,225,539, 5,530,101, and 5,585,089), veneering or resurfacing (EP 592,106; EP 519,596; Padlan, 1991, Molecular Immunology 28(4/5):489-498; Studnicka et al., 1994, Protein Engineering 7:805; and Roguska et al., 1994, Proc. Natl. Acad. Sci. USA 91:969), and chain shuffling (U.S. Pat. No. 5,565,332).

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies and is not to be construed as requiring production of the antibody by any particular method. For example, the monoclonal antibodies to be used in accordance with the present disclosure may be made by the hybridoma method first described by Kohler et al., Nature, 256:495 (1975), or may be made by recombinant DNA methods (see, e.g., U.S. Pat. No. 4,816, 567). The "monoclonal antibodies" may also be isolated from phage antibody libraries using the techniques described in Clackson et al., Nature, 352:624-628 (1991) and Marks et al. J. Mol. Biol., 222:581-597 (1991), for example.

The term "diabodies" refers to small antibody fragments with two antigen binding sites, which fragments comprise a variable heavy domain ($V_H$) connected to a variable light domain ($V_L$) in the same polypeptide chain ($V_H$-$V_L$). By using a linker that is too short to allow pairing between the two domains on the same chain, the domains are forced to pair with the complementary domains of another chain and create two antigen binding sites. Diabodies are described more fully in, for example, EP 404,097; WO 93/11161; and Hollinger et al., Proc. Natl. Acad. Sci. USA, 90:6444-6448 (1993).

A "full length antibody" is one which comprises an antigen binding variable region as well as a light chain constant domain (CO and heavy chain constant domains, $C_H1$, $C_H2$ and $C_H3$). The constant domains may be native sequence constant domains (e.g. human native sequence constant domains) or amino acid sequence variants thereof. In one aspect, the full length antibody has one or more effector functions.

An "amino acid sequence variant" antibody herein is an antibody with an amino acid sequence which differs from a main species antibody. Ordinarily, amino acid sequence variants will possess at least about 70%, at least about 80%, at least about 85%, at least about 90%, or at least about 95% homology with the main species antibody. The amino acid sequence variants possess substitutions, deletions, and/or additions at certain positions within or adjacent to the amino acid sequence of the main species antibody but retain antigen binding activity. Variations in sequence of the constant regions of the antibody will have less effect on the antigen binding activity than variations in the variable regions. In the variable regions, amino acid sequence variants will be at least about 90% homologous, at least about 95% homologous, at least about 97% homologous, at least about 98% homologous, or at least about 99% homologous with the main species antibody.

"Homology" is defined as the percentage of residues in the amino acid sequence variant that are identical after aligning the sequences and introducing gaps, if necessary, to achieve the maximum percent homology.

A "glycosylation variant" antibody herein is an antibody with one or more carbohydrate moieties attached thereto which differ from one or more carbohydrate moieties attached to a main species antibody. Examples of glycosylation variants herein include antibody with a G1 or G2 oligosaccharide structure, instead of a G0 oligosaccharide structure, attached to an Fc region thereof, antibody with one or two carbohydrate moieties attached to one or two light chains thereof, antibody with no carbohydrate attached to one or two heavy chains of the antibody, etc, and combinations of glycosylation alterations.

Antibody "effector functions" refer to those biological activities attributable to the Fc region (a native sequence Fc region or amino acid sequence variant Fc region) of an antibody. Examples of antibody effector functions include Clq binding; complement dependent cytotoxicity; Fc receptor binding; antibody-dependent cell-mediated cytotoxicity (ADCC); phagocytosis; down regulation of cell surface receptors (e.g. B cell receptor; BCR), and the like.

Depending on the amino acid sequence of the constant domain of their heavy chains, full length antibodies can be assigned to different "classes." There are five major classes of full-length antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called alpha, delta, epsilon, gamma, and mu, respectively. The "light chains" of antibodies from any vertebrate species can be assigned to one of two clearly distinct types, called kappa and lambda, based on the amino acid sequences of their constant domains.

The terms "Fc receptor" or "FcR" are used to describe a receptor that binds to the Fc region of an antibody. In one aspect, the FcR is a native sequence human FcR. In another aspect, the FcR is one which binds an IgG antibody (a gamma receptor) and includes receptors of the FcgammaRI, FcgammaRII, and FcgammaRIII subclasses, including allelic variants and alternatively spliced forms of these receptors. FcgammaRII receptors include FcgammaRIIA (an "activating receptor") and FcgammaRIIB (an "inhibiting receptor"), which have similar amino acid sequences that differ primarily in the cytoplasmic domains thereof. Activating receptor FcgammaRIIA contains an immunoreceptor tyrosine-based activation motif (ITAM) in its cytoplasmic domain. Inhibiting receptor FcgammaRIIB contains an immunoreceptor tyrosine-based inhibition motif (ITIM) in its cytoplasmic domain. (See review in M. Daeron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126:33-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

"Antibody-dependent cell-mediated cytotoxicity" and "ADCC" refer to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The primary cells for mediating ADCC, NK cells, express FcgammaRIII only, whereas monocytes express FcgammaRI, FcgammaRII and FcgammaRIII. To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. PNAS (USA) 95:652-656 (1998).

HPV and Cancer

HPV infections can be detected by testing a sample of cells to see if they contain viral DNA or RNA. HPV type 16 is responsible for many HPV-caused cancers. The genome of HPV 16 can be divided into 3 domains: an early region with 6 open reading frames (ORFs) E6, E7, E1, E2, E4 and E5; a late region with 2 ORFs, L1 (the major capsid protein) and L2 (the minor capsid protein). The E2 protein binds E1 and stimulates viral DNA replication while both the E6 and E7 proteins play a role in the cell transformation and immortalization.

E2 [Human papillomavirus type 16] is a regulatory protein identified with NCBI Reference Sequence: NP_041328.1: METLCQRLNVCQDKILTHYEND-STDLRDHIDYWKHMRLECAIYYKAREMGFKH-INHQV VPTLAVSKNKALQAIELQLTLETIYNSQYSNE-KWTLQDVSLEVYLTAPTGCIKKHGYTV EVQFDGD-ICNTMHYTNWTHIYICEEASVTVVEGQVDYYG-LYYVHEGIRTYFVQFKDDA EKYSKNKVWEVHAG-GQVILCPTSVFSSNEVSSPEIIRQHLANHPAATH-TKAVALGTEET QTTIQRPRSEPDTGNPCHTTKLLHR-DSVDSAPILTAFNSSSHKGRINCNSNTTPIVHLKGDA NTLKCLRYRFKKHCTLYTAVSSTWHWTGHNVKHK-SAIVTLTYDSEWQRDQFLSQVKIP KTITVSTGFMSI (SEQ ID NO: 1). Known variants include, but are not limited to D to N at position 25, A to T at position 105, T to K at 135, R to Q at 165; E to K at 185; I to T at 210, P to S at 219, T to K at 310, D to E at 344, and G to V at 361.

E6 [Human papillomavirus type 16] is a transforming protein identified with NCBI Reference Sequence: NP_041325.1: MHQKRTAMFQDPQERPRKLPQLCT-ELQTTIHDIILECVYCKQQLLRREVYDFAFRDLCIV YRDGNPYAVCDKCLKFYSKISEYRHYCYSLYGT-TLEQQYNKPLCDLLIRCINCQKPLCPE EKQRHLDK-KQRFHNIRGRWTGRCMSCCRSSRTRRETQL (SEQ ID NO: 15). Known variants include, but are not limited to I to L at position Q to E at position 10, K to R at position 19, Q to E at position 21, 34, L to V at position 35, L to V at position 74, L to V at position 90, Q to E at position 123, K to R at position 129, and R to K at position 154.

The molecular mechanism of HPV carcinogenesis was previously thought to be regulated by two viral oncogenes E6 and E7. The E6 and E7 genes are under the regulation of the E2 gene product. The E6 gene product binds to the p53 tumor suppressor gene. The association of E6 with p53 leads to the specific ubiquitination and degradation of p53 protein. E7 targets another tumor suppressor protein, the retinoblastoma gene product (pRb). Binding of the E7 to pRb alters its phosphorylation state and thereby functionally inactivates this protein, which, like p53, functions in the control of the cell cycle. Normally, pRb binds the transcription factor E2F, which functions in the progression of the cell cycle from G1 to the S phase. The binding of E7 to pRb results in creation of an inactive E7-pRb complex; on the other hand, disrupted binding of E2F to pRb allows E2F to bind DNA and induce the cell growth and proliferation.

Although it is not intended that embodiments of this disclosure be limited by any particular mechanism, the route of HPV infection through the epithelial mucosa basal cell layer believed to be by microtraumas. There is coordinate expression of the different viral gene products, with E6/E7 causing an expansion of S-phase competent cells. This allows viral genome amplification and, ultimately, the synthesis and shedding of new viral particles. In the case of persistent infection, lesions are not resolved, and high levels of viral DNA can be detected over extended periods of time. This ultimately pre-disposes the host to the development of a malignancy. This is characterized by a loss of differentiation, no viral replication, and high levels of E6 and E7 oncoprotein expression. There is abnormal cell growth leading to the formation of an area of precancerous cells and, ultimately, a cancerous tumor.

Genital warts, benign respiratory tract tumors, precancerous changes at the cervix, and cancers resulting from HPV infections can be treated. HPV-infected individuals who develop cancer generally receive the same treatment as patients whose tumors do not harbor HPV infections, according to the type and stage of their tumors. However, there is no medical treatment for persistent HPV infections that are not associated with visible abnormal cell changes.

It is believed that it can take between 10 and 30 years from the time of an initial HPV infection until tumors form. However, even when severely abnormal cells are seen on the cervix (a condition called cervical intraepithelial neoplasia 3, or CIN3), these do not always lead to cancer. Historically, cancer of the throat oropharynx (throat) was associated with the use of alcohol and tobacco, but most of cases are now associated with the HPV virus. More currently, most of oropharyngeal cancers in the US are caused by HPV with HPV 16 accounting for almost 90% of HPV mediated oropharyngeal cancers. The biology of HPV-positive oropharyngeal cancer is typified by p53 degradation, retinoblastoma protein (Rb) down-regulation and p16 up-regulation. By contrast, tobacco-related oropharyngeal cancer is characterized by p53 mutations, down-regulation of p16 and Rb up-regulation.

Therapeutic strategies for those already infected and/or have HPV-related cancers focus on eliciting cellular immune responses against the E6 and/or E7 oncogenes of HPV. There is a need to develop diagnostic and therapeutic agents that will work on other HPV targets. Immunohistochemistry (IHC) p16 is a current marker to detect HPV presence in head and neck squamous cell carcinoma (HNSCC). However, it can be associated with a high rate of false positive/false negative responses, prompting the need for new surrogate markers for oral HPV infection. HPV-specific antibodies that can be useful diagnostics as well as therapeutic agents for the treatment of HPV related cancers and a therapeutic vaccine.

Figure 1B:
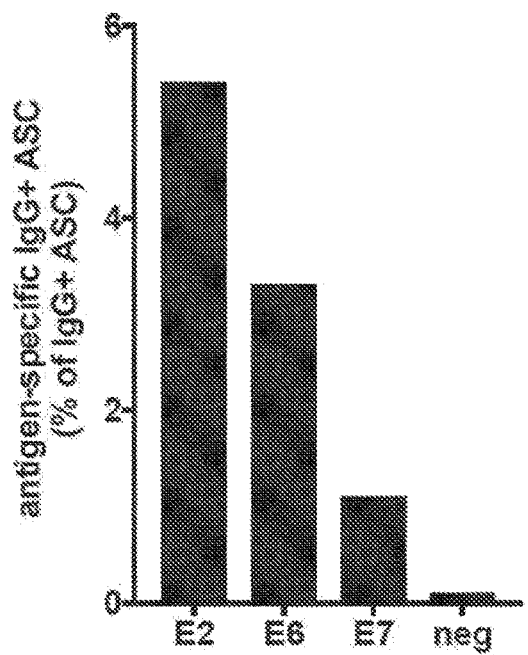
FIG. 1B shows data on antigen-specific IgG-secreting ASCs in the tumor-containing lymph node of a representative p16+ HNSCC patient. Wells were coated with 1 ug of recombinant maltose binding protein (MBP)—fusion protein. Neg=MBP protein alone.
Figure 2A:
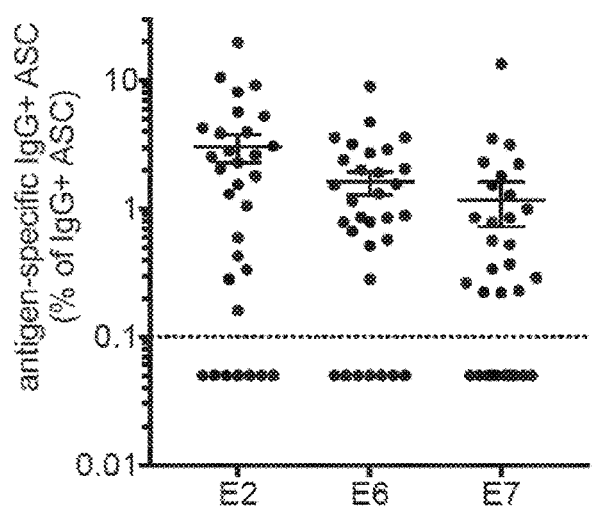
FIG. 2A shows summary of isotype profile of ASCs in tumor-containing lymph nodes of 31 p16+ HNSCC patients.
Figure 2B:
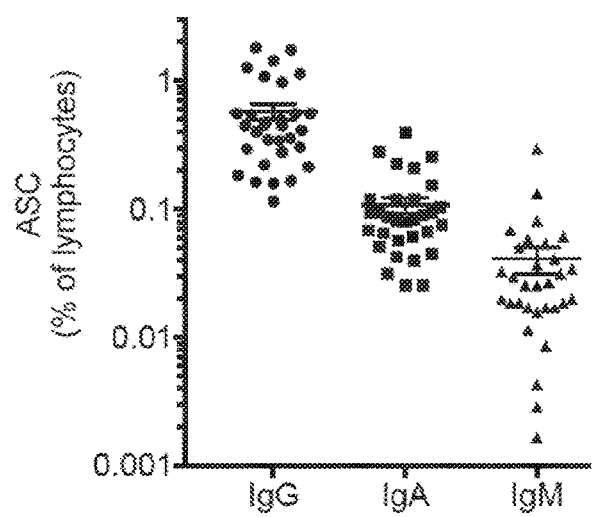
FIG. 2B shows summary of antigen-specific IgG-secreting ASCs in tumor-containing lymph nodes of 31 p16+ HNSCC patients.
Figure 3A:
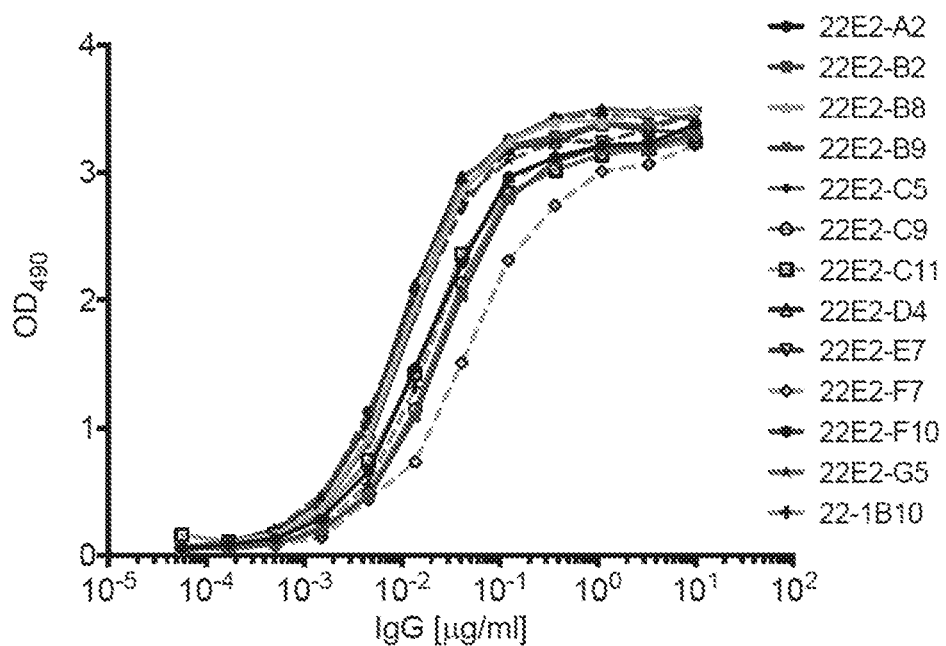
FIG. 3A shows ELISA binding data of E2-specific human monoclonal antibodies. ELISA plates coated with recombinant MBP-E2 fusion protein were incubated with purified human monoclonal antibodies.
Figure 3B:
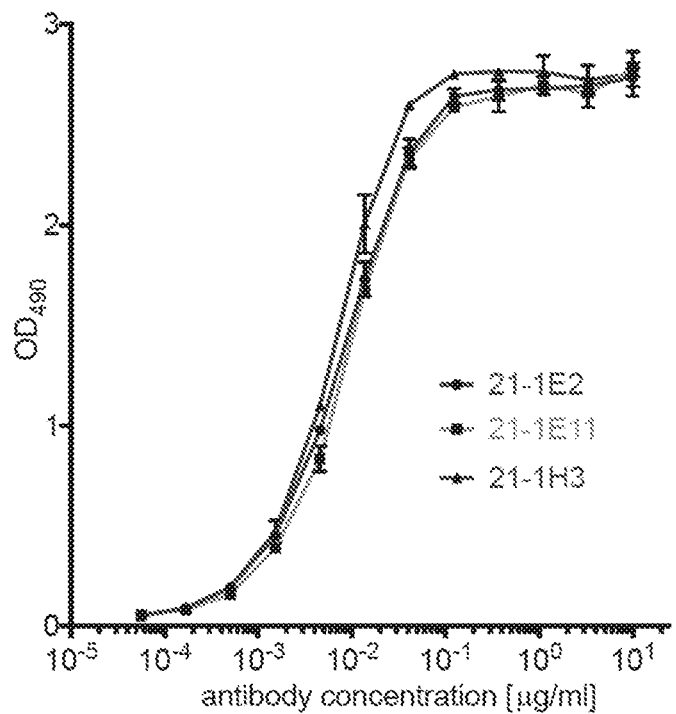
FIG. 3B shows ELISA binding data of E6-specific human monoclonal antibodies. ELISA plates coated with recombinant MBP-E6 fusion protein were incubated with purified human monoclonal antibodies.
Figure 3C:
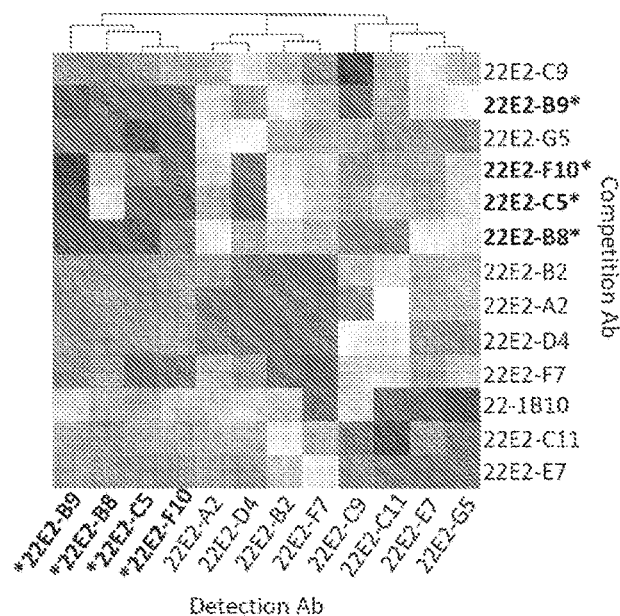
FIG. 3C shows binding pattern of E2-specific human monoclonal antibodies. ELISA plates coated with recombinant MBP-E2 fusion protein were first incubated with excess competing human monoclonal antibody, followed by incubation with E2-specific monoclonal antibodies (expressed with mouse IgG2a Fc) and a final detection step with an anti-mouse IgG antibody. E2-specific mAbs shown in bold and with an asterisk recognize linear epitopes of E2 as determined by Western Blot.
Figure 4:
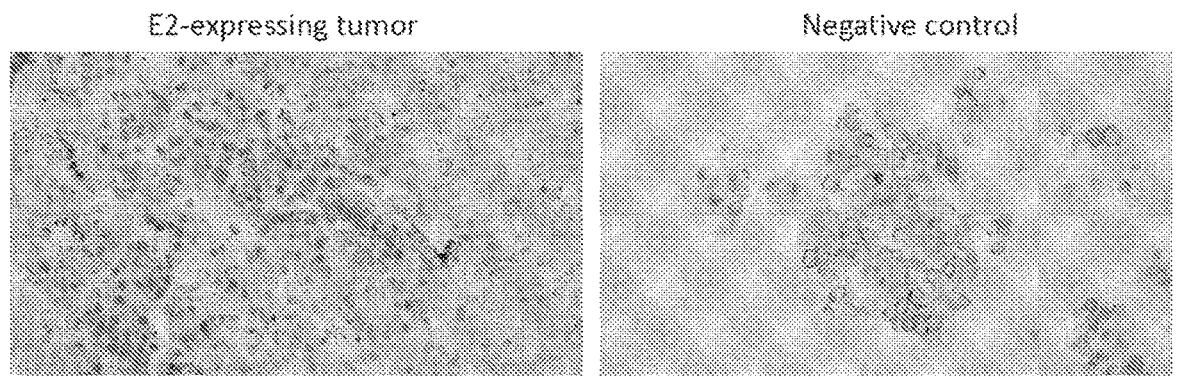
FIG. 4 shows data regarding the use of E2-specific human monoclonal antibodies for detection of E2-expressing tumor cells by immunohistochemistry (IHC). E2-expressing mouse tumor (left panel) was excised from a mouse, fixed in formalin and embedded in paraffin. The parental tumor cell line not expressing E2 was pelleted and treated accordingly (right panel). IHC with an E2-specific human monoclonal antibody was performed and E2 was detected in the nucleus (apparent as bright staining).
Figure 5:
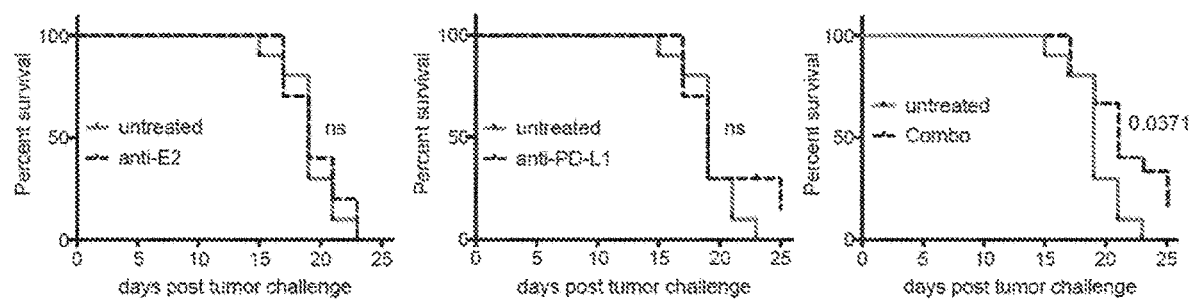
FIG. 5 shows survival of mice challenged with an E2-expressing tumor cell line and therapeutically treated with an E2-specific human monoclonal antibody (anti-E2; left panel), a PD-L1 blocking antibody (anti-PD-L1; middle panel) or a combination of an E2-specific human monoclonal antibody and PD-L1 blocking antibody (combo, right panel). Treatment was initiated on day 9 post tumor implantation and continued for 2 weeks (grey shaded area). Tumor growth was monitored, and mice were euthanized once reaching the defined endpoint of 1500 mm$^3$ tumor volume. Untreated group is shown in grey, treated group is indicated in the respective panel by dashed black line. n=10-15 mice per group. Log-rank (Mantel-Cox) test was used to compare survival curves. p value is indicated. ns=not significant.
Figure 6A:
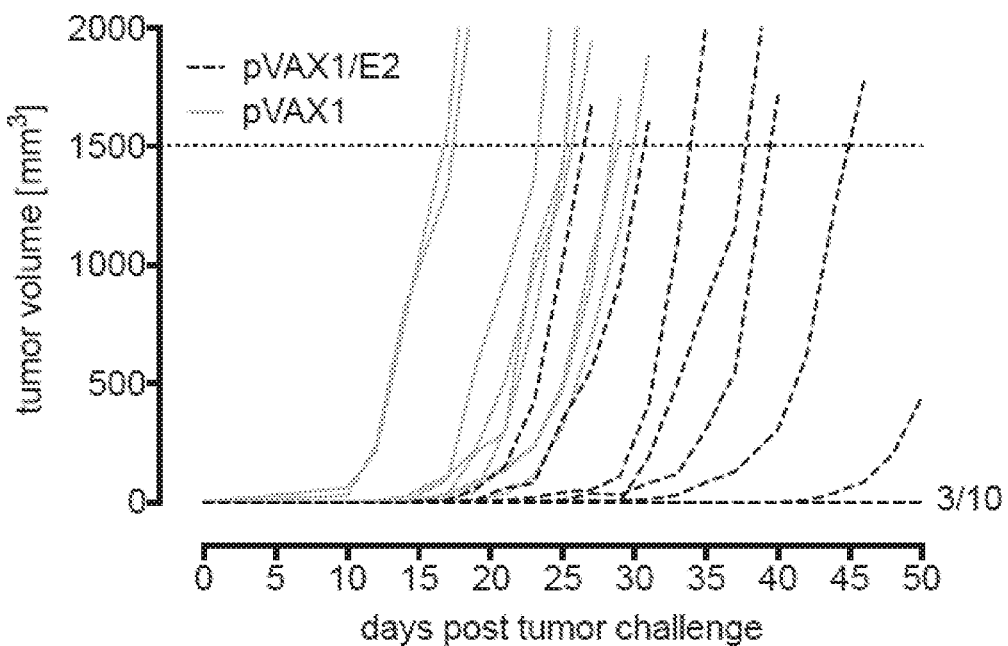
FIG. 6A shows growth of an E2-expressing tumor cell line in mice vaccinated with control plasmid (pVAX1; grey lines) or with E2-expressing plasmid (pVAX1/E2; dashed black lines). Defined endpoint of 1500 mm$^3$ tumor volume is indicated by dashed line. 9/9 mice immunized with the control plasmid reached the defined endpoint within 30 days, whereas 3/10 mice immunized with E2-expressing plasmid were completely protected for at least 50 days.
Figure 6B:
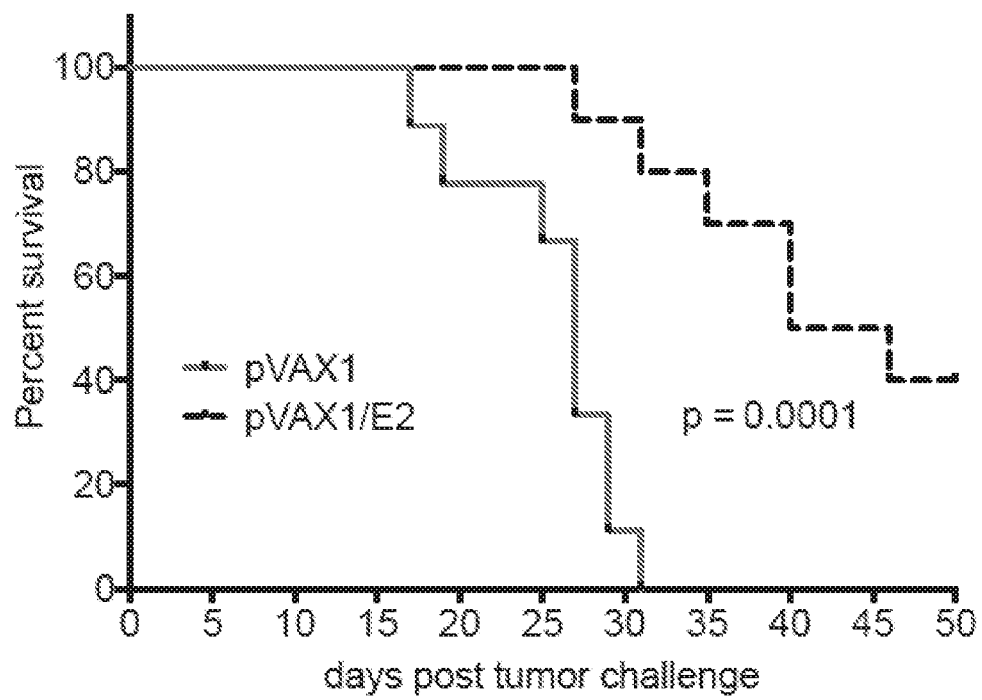
FIG. 6B shows survival curves of mice vaccinated with a control plasmid (pVAX1; grey lines) or with a E2-expressing plasmid (pVAX1/E2; dashed black lines) followed by challenge with a E2-expressing tumor cell line. Mice were euthanized once reaching the defined endpoint of 1500 mm$^3$ tumor volume. n=9-10 mice per group. Log-rank (Mantel-Cox) test was used to compare survival curves. p value is indicated.

Metastatic lymph node samples of 14 p16 positive head and neck squamous cell carcinoma (HNSCC) were identified in patients undergoing surgical resection. Lymphocytes were isolated by enzymatic and mechanic disruption. Antibody secreting cell (ASC) ELISPOT was performed to identify total as well as HPV specific antibody secreting plasmablasts (see FIGS. 1-2). Plasmablasts in the lymph nodes were mostly producing IgG antibodies. Plasmablasts specific for HPV E2, E6 and E7 were detected using bacterial fusion proteins. Plasmablasts specific for HPV E2, E6 or E7 could be detected and accounted for up to 10% of all IgG secreting plasmablasts in the lymph nodes. Patient samples showed significant plasmablast response directed against E2. It was unexpected to find such a large amount of E2 specific plasmablasts because E2 was not known as a structural protein.

Diagnostic Methods

In certain embodiments, this disclosure relates to detecting an HPV protein in a sample and correlating the presence as an indication that a subject is at risk of developing an HPV-related disease or condition. In certain embodiments, this disclosure relates to methods of detecting HPV-infected cells comprising: obtaining a sample of human epithelial tissue from a subject, and detecting an HPV protein in the epithelial tissue or a malignancy or pre-malignancy inside the epithelial tissue indicating an HPV 16 infection. In certain embodiments, the HPV protein is E2 and/or E6.

HPV antibodies can be used to perform immunoassays for different human subjects for comparison with positive and negative controls. Embodiments of the disclosure provide various antibodies against an HPV protein such that infection by high risk and low risk HPV types can be detected by an antibody. In certain embodiments, the HPV protein is E2 and/or E6. The disclosure also provides HPV type specific antibodies for detecting the high-risk HPV types. In addition, antibodies highly specific for an HPV protein are also provided. In certain embodiments, the HPV protein is E2 and/or E6.

These HPV antibodies can be used for one or more immunological assays to detect HPV infection and HPV-related cervical cancer and other diseases. In certain embodiments, the HPV protein is E2 and/or E6. The suitable immunological assay may include ELISA (enzyme linked immunosorbent assays), antigen assays for papillomavirus proteins, antibody assays for antibodies against papillomavirus proteins, assays for papillomavirus immunocomplexes, protein chip assays, radioimmunoprecipitation assays, rapid membrane immunochromatographic assays, rapid stick immunochromatographic assays, immunohistochemistry for tissues and/or cervical cells, and immunocytochemistry assays followed by flow cytometry.

In certain embodiments, HPV antibodies can be used to test various biological samples, cell lines, and/or clinical samples of various grades of epithelial lesions (cervical intraepithelial neoplasia (CIN) grade 2 and grade 3 (CIN2, and CIN3, respectively), low grade of squamous intraepithelial lesion (LSIL) or high grade of squamous intraepithelial lesion (HSIL), or atypical squamous cells of undetermined significance (ASCUS)) as well as different cervical cancers, squamous cell carcinoma (SCC, a type of common cancer) and adenocarcinoma (ADC, a type of gland cancer). In certain embodiments, the HPV protein is E2 and/or E6.

In certain embodiments, this disclosure relates to methods of screening a human subject of papillomavirus infection includes obtaining a clinical sample from the human subject and conducting one or more immunological assays on the clinical sample from the human subject using various HPV recombinant proteins and antibodies for the HPV proteins in order to detect and screen for the presence of HPV infection from the presence of HPV antibodies and HPV proteins in the human subject. In certain embodiments, the HPV protein is E2 and/or E6.

In certain embodiments, this disclosure relates to methods of detecting HPV-infected cells comprising: obtaining a sample from a subject and mixing the sample with a specific binding agent, such as an antibody that binds an HPV protein, and detecting the specific binding agent or antibody binding to the HPV protein indicating the sample contains cells comprising a nucleic acid encoding the HPV protein. In certain embodiments, the HPV protein is E2 and/or E6. In certain embodiments, the subject is not expressing symptoms of an active HPV infection. In certain embodiments, human epithelial tissue does not contain detectable amounts of infectious HPV virial particles. In some embodiments, the subject is known to be infected or suspected of being infected with HPV16.

In certain embodiments, the sample is an epithelial tissue. In certain embodiments, the sample comprises cells obtained from a pharynx, oropharynx, nasopharynx, lips, oral cavity, tongue, tonsil, soft palate, hard palate, jaw, esophagus, or larynx. In certain embodiments, the sample comprises cells obtained from a vagina, cervix, volva, penis, or anal canal.

The antibodies to an HPV protein may be present in various sources of biological samples. In certain embodiments, the HPV protein is E2 and/or E6. As an example, the antibodies to an HPV protein can be used as capture antibody to coat on microtiter plate and/or used as detection antibody as a sandwich format of ELISA (Enzyme Linked Immuno Sandwich Assay). The antibody to an HPV protein can be directly conjugated with label like biotin, alkaline phosphatase, HRP, fluorescent, etc., followed by color metric, chemiluminescent or fluorescent substrate for readout. The detection antibody for an HPV protein can be identified by a secondary antibody conjugated with label like biotin, alkaline phosphatase, HRP, fluorescent, etc. For direct EIA (Enzyme Immuno Assay), cells, samples or cultured cells to be tested may be collected and lysed to generate cell late as analyte. The HPV protein in the cell lysate may be quantitated and coated to microtiter plate using the same amount of protein for coating of each sample in each well followed by the detection antibody with specificity described herein.

In addition, detection of HPV protein antibodies by immunological assays can be used in general clinical screening for HPV infection and early diagnosis for cervical cancer and can be performed in a single rapid test or in multiplexed test. In certain embodiments, the HPV protein is E2 and/or E6. Comparative detection of altered levels of HPV proteins and host peptides can be performed in the same or different assays. It can also be used in diagnosing HPV-associated carcinomas of the uterine cervix, as well as those cases associated with epithelial cell abnormalities induced by HPV infection, pre-malignant and malignant HPV-associated epithelial cell lesions, and those at risk of developing HPV-associated cervical carcinoma and adenocarcinoma. The methods as described herein can be used independently or as an adjunct screening tool to convention cytological papanicolaou (Pap) smear tests or histological tests and the results thereof can be compared for follow-up patient management.

Therapeutic Intervention

In certain embodiments, this disclosure relates to methods of treating or preventing cancer in a subject comprising administering an effective amount of an anti-viral agent and/or an anti-HPV antibody therapy, or specific binding agent or antibody that binds an HPV protein to the subject diagnosed as at risk of developing cancer or spreading HPV. In certain embodiments, the HPV protein is E2 and/or E6. In certain embodiments, the administration is topical to the epithelial tissue, skin, genitals, penis, volva, vagina, anal opening, or anal canal. In certain embodiments, the administration by placement of a vaginal ring comprising agents disclosed herein.

In certain embodiments, this disclosure relates to methods for diagnosing and treating or preventing cancer in a subject comprising: obtaining a sample of human epithelial tissue from a subject, and detecting HPV protein in the epithelial tissue or a malignancy or pre-malignancy inside the epithelial tissue; diagnosing the subject as a subject at risk of developing cancer, and administering an effective amount of an anti-viral agent or anti-HPV therapy, or specific binding agent or antibody that binds the HPV protein to the subject diagnosed as at having or at risk of developing cancer or spreading HPV. In certain embodiments, the specific binding agent or antibody is conjugated to a toxin, cell lysing agent, or apoptosis inducing agent. In certain embodiments, the administration is topical to the epithelial tissue, skin, genitals, penis, volva, vagina, anus opening or anal canal. In certain embodiments, the HPV protein is E2 and/or E6.

In certain embodiments, the disclosure relates to methods for diagnosing and treating or preventing cancer in a subject comprising: obtaining a sample from a subject and mixing the sample with a specific binding agent that binds an HPV protein, detecting the specific binding agent binding to the HPV protein indicating the sample contains cells comprising a nucleic acid encoding the HPV protein, diagnosing the subject as a subject at risk of developing cancer, and administering an effective amount of an anti-viral agent or anti-HPV therapy, or specific binding agent or antibody that binds the HPV protein to the subject diagnosed as at risk of developing cancer. In certain embodiments, the HPV protein is E2 and/or E6. In certain embodiments, the subject is human diagnosed with HPV-related carcinoma, HPV-positive oropharyngeal carcinoma, HPV-positive cervical carcinoma, HPV-positive anal carcinoma HPV-positive vulvar carcinoma, or HPV-positive penile carcinoma.

In certain embodiments, this disclosure relates to methods for diagnosing and preventing cancer in a subject comprising: obtaining a sample of human epithelial tissue from a subject, and detecting an HPV protein in the epithelial tissue or a malignancy or pre-malignancy inside the epithelial tissue; diagnosing the subject as a subject at risk of developing cancer, and administering an effective amount of an anti-viral agent or anti-HPV therapy, or specific binding agent or antibody that binds the HPV protein to the subject diagnosed as at risk of developing cancer. In certain embodiments, the HPV protein is E2 and/or E6.

In certain embodiments, the subject is a female. In certain embodiments, the subject is older than 25, between 30-65, 25-40, or 40-65 years, as a follow-up to a Pap test that finds abnormal or malignant cells or when a Pap test results are unclear. In certain embodiments, the methods are performed on a subject in combination with a Pap test.

In certain embodiments, this disclosure relates to methods for diagnosing and treating or preventing cancer in a subject comprising: obtaining a sample from a subject and mixing the sample with an antibody that binds a HPV protein, detecting the antibody binding to the HPV protein indicating the sample contains cells comprising a nucleic acid encoding the HPV protein, diagnosing the subject as a subject at risk of developing cancer, and administering an effective amount of an anti-viral agent or anti-HPV therapy, or specific binding agent or antibody that binds HPV E2 protein to the subject diagnosed as at risk of developing cancer. In certain embodiments, the HPV protein is E2 and/or E6. In certain embodiments, the subject is not expressing symptoms of an active HPV infection.

In certain embodiments, the sample is an epithelial tissue. In certain embodiments, the sample comprises cells obtained from a pharynx, oropharynx, nasopharynx, lips, oral cavity, tongue, tonsil, soft palate, hard palate, jaw, esophagus, or larynx. In certain embodiments, the sample comprises cells obtained from a vagina, cervix, volva, penis, or anal canal.

In certain embodiments, this disclosure relates to method of treating cancer comprising administering an effective amount of an anti-viral agent or anti-HPV therapy, or specific binding agent or antibody that binds an HPV protein to a subject at risk of or diagnosed with HPV. In certain embodiments, the HPV protein is E2 and/or E6. In certain embodiments, the cancer is a head or neck cancer. In certain embodiments, the cancer is a vaginal, cervical, volva, penile, or anal cancer.

In certain embodiments, this disclosure relates to methods of treating or preventing genital warts comprising administering an effective amount of an anti-viral agent or anti-HPV therapy, or specific binding agent or antibody that binds an HPV protein to a subject at risk of or diagnosed with HPV. In certain embodiments, the HPV protein is E2 and/or E6.

In certain embodiments, this disclosure relates to methods of treating or preventing recurrent respiratory papillomatosis comprising administering an effective amount of an anti-viral agent or anti-HPV therapy, or specific binding agent or antibody that binds an HPV protein to a subject at risk of or diagnosed with HPV. In certain embodiments, the HPV protein is E2 and/or E6.

In certain embodiments, this disclosure relates to methods of treating cancer comprising administering an effective amount of an antibody that binds an HPV protein to a subject at risk of or diagnosed with HPV. In certain embodiments, the HPV protein is E2 and/or E6. In certain embodiments, the antibody that binds the HPV protein is administered in combination with an anti-CTLA4 or anti-PD1/PD-L1 antibody.

In certain embodiments, the antibody is capable of antibody-dependent cell-mediated cytotoxicity (ADCC) antibody-dependent cell-mediated phagocytosis, complement-dependent cell-mediated cytotoxicity (CDCC), and complement-dependent cell-mediated phagocytosis (CDCP). In certain embodiments, the specific binding agent or antibody is conjugated to a toxin, cell lysing agent, radionuclide, or apoptosis inducing agent.

Engineering of the fragment crystallizable (Fc) of an antibody by modifying the amino acid sequence (Fc protein engineering) or the glycosylation pattern (Fc glyco-engineering) allows enhancing effector functions of tumor targeting antibodies. Thus, in certain embodiments, the antibodies disclosed herein have a variant carrying the EFTAE modification (S267E/H268F/S324T/G236A/I332E) as well as glyco-engineered, non-fucosylated derivatives. See Moore et al. Engineered Fc variant antibodies with enhanced ability to recruit complement and mediate effector functions. MAbs. 2010, 2:181-189.

In certain embodiments, the disclosure relates to methods of preventing or treating an HPV infection comprising administering an effective amount of a pharmaceutical composition comprising an antibody or antigen binding fragment disclosed herein to a subject in need thereof. Treatment of a subject with a therapeutically or prophylactically effective amount of antibody or antibody binding fragment can include a single treatment or, preferably, can include a series of treatments. In certain embodiments, the subject is at risk of, exhibiting symptoms of, or diagnosed with an HPV infection.

In certain embodiments, the antibody or antigen binding fragment is administered in combination with another or second therapeutic agent or antiviral agent.

In certain embodiments, the antiviral agent(s) is abacavir, acyclovir, acyclovir, adefovir, amantadine, amprenavir, ampligen, arbidol, atazanavir, atripla, boceprevir, cidofovir, combivir, darunavir, delavirdine, didanosine, docosanol, dolutegravir, edoxudine, efavirenz, emtricitabine, enfuvirtide, entecavir, famciclovir, fomivirsen, fosamprenavir, foscarnet, fosfonet, ganciclovir, ibacitabine, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir, peginterferon alfa-2a, penciclovir, peramivir, pleconaril, podophyllotoxin, raltegravir, ribavirin, rimantadine, ritonavir, saquinavir, stavudine, tenofovir, tenofovir disoproxil, tenofovir alafenamide fumarate, tipranavir, trifluridine, trizivir, tromantadine, valaciclovir, valganciclovir, vicriviroc, vidarabine, viramidine, zalcitabine, zanamivir, or zidovudine, and combinations thereof.

Dosage amounts and frequencies of administration provided herein are encompassed by the terms therapeutically effective and prophylactically effective. The dosage and frequency further will typically vary according to factors specific for each patient depending on the specific therapeutic or prophylactic agents administered, the severity, the route of administration, as well as age, body weight, response, and the past medical history of the patient. Suitable regimens can be selected by one skilled in the art by considering such factors and by following, for example, dosages reported in the literature and recommended in the Physician's Desk Reference (56th Ed., 2002).

Various delivery systems can be used to administer the therapeutic or prophylactic compositions, e.g., encapsulation in liposomes, microparticles, microcapsules, recombinant cells capable of expressing the antibody or fusion protein, receptor-mediated endocytosis (see, e.g., Wu and Wu, 1987, J. Biol. Chem. 262:4429-4432), construction of a nucleic acid as part of a retroviral or other vector, etc.

Methods of administering antibodies and antigen binding fragments include, but are not limited to, parenteral administration (e.g., intradermal, intramuscular, intraperitoneal, intravenous and subcutaneous), epidural, and mucosal (e.g., intranasal and oral routes). In a specific embodiment, the antibodies or fusion proteins are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985,20; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903. In a specific embodiment, it may be desirable to administer the pharmaceutical compositions locally to the area in need of treatment; this may be achieved by, for example, and not by way of limitation, local infusion, by injection, or by means of an implant, said implant being of a porous, non-porous, or gelatinous material, including membranes, such as silastic membranes, or fibers.

In some embodiments, the antibodies or antigen binding fragments are formulated in liposomes for targeted delivery of the antibodies or fusion proteins. Liposomes are vesicles comprised of concentrically ordered phospholipid bilayers which encapsulate an aqueous phase. Liposomes typically comprise various types of lipids, phospholipids, and/or surfactants. The components of liposomes are arranged in a bilayer configuration, similar to the lipid arrangement of biological membranes. Liposomes are particularly preferred delivery vehicles due, in part, to their biocompatibility, low immunogenicity, and low toxicity. Methods for preparation of liposomes and are encompassed within the disclosure, see, e.g., Epstein et al., 1985, Proc. Natl. Acad. Sci. USA, 82: 3688; Hwang et al., 1980 Proc. Natl. Acad. Sci. USA, 77: 4030-4; U.S. Pat. Nos. 4,485,045 and 4,544,545.

Methods of preparing liposomes with a prolonged serum half-life, i.e., enhanced circulation time, such as those disclosed in U.S. Pat. No. 5,013,556 can be used to make liposomes-antibody compositions. Preferred liposomes are not rapidly cleared from circulation, i.e., are not taken up into the mononuclear phagocyte system (MPS). Although not intending to be bound by a particular mechanism of action, sterically stabilized liposomes contain lipid components with bulky and highly flexible hydrophilic moieties, which reduces the unwanted reaction of liposomes with serum proteins, reduces opsonization with serum components and reduces recognition by MPS. Sterically stabilized liposomes are preferably prepared using polyethylene glycol. For preparation of liposomes and sterically stabilized liposome, see, e.g., Bendas et al., 2001 BioDrugs, 15(4): 215-224; Allen et al., 1987 FEBS Lett. 223: 42-6; Klibanov et al., 1990 FEBS Lett., 268: 235-7; Blum et al., 1990, Biochim. Biophys. Acta., 1029: 91-7; Torchilin et al., 1996, J. Liposome Res. 6: 99-116; Litzinger et al., 1994, Biochim. Biophys. Acta, 1190: 99-107; Maruyama et al., 1991, Chem. Pharm. Bull., 39: 1620-2; Klibanov et al., 1991, Biochim Biophys Acta, 1062; 142-8; Allen et al., 1994, Adv. Drug Deliv. Rev, 13: 285-309. The disclosure also encompasses liposomes that are adapted for specific organ targeting, see, e.g., U.S. Pat. No. 4,544,545, or specific cell targeting, see, e.g., U.S. Patent Application Publication No. 2005/0074403. Particularly useful liposomes for use in the disclosed compositions and methods can be generated by reverse phase evaporation method with a lipid composition comprising phosphatidylcholine, cholesterol, and PEG derivatized phosphatidylethanolamine (PEG-PE). Liposomes are extruded through filters of defined pore size to yield liposomes with the desired diameter. In some embodiments, a fragment of an antibody, e.g., F(ab'), may be conjugated to the liposomes using previously described methods, see, e.g., Martin et al., 1982, J. Biol. Chem. 257: 286-288.

The antibodies, or antigen binding fragments may also be formulated as immunoliposomes. Immunoliposomes refer to a liposomal composition, wherein an antibody or a fragment thereof is linked, covalently or non-covalently to the liposomal surface. The chemistry of linking an antibody to the liposomal surface is encompassed within the disclosure, see, e.g., U.S. Pat. No. 6,787,153; Allen et al., 1995, Stealth Liposomes, Boca Rotan: CRC Press, 233-44; Hansen et al., 1995, Biochim. Biophys. Acta, 1239: 133-144. In most preferred embodiments, immunoliposomes for use in the disclosed methods and compositions are further sterically stabilized. Preferably, the antibodies or antigen binding fragments are linked covalently or non-covalently to a hydrophobic anchor, which is stably rooted in the lipid bilayer of the liposome. Examples of hydrophobic anchors include, but are not limited to, phospholipids, e.g., phosphatidylethanolamine (PE), phosphatidylinositol (PI). To achieve a covalent linkage between an antibody and a hydrophobic anchor, biochemical strategies may be used, see, e.g., J. Thomas August, ed., 1997, Gene Therapy: Advances in Pharmacology, Volume 40, Academic Press, San Diego, Calif., p. 399-435. For example, a functional group on an antibody molecule may react with an active group on a liposome associated hydrophobic anchor, e.g., an amino group of a lysine side chain on an antibody may be coupled to liposome associated N-glutaryl-phosphatidylethanolamine activated with water-soluble carbodiimide; or a thiol group of a reduced antibody can be coupled to liposomes via thiol reactive anchors, such as pyridylthiopropionylphosphatidylethanolamine. See, e.g., Dietrich et al., 1996, Biochemistry, 35: 1100-1105; Loughrey et al., 1987, Biochim. Biophys. Acta, 901: 157-160; Martin et al., 1982, J. Biol. Chem. 257: 286-288; Martin et al., 1981, Biochemistry, 20: 4429-38. Although not intending to be bound by a particular mechanism of action, immunoliposomal formulations including an antibody or fusion protein are particularly effective as therapeutic agents, since they deliver the antibody or fusion protein to the cytoplasm of the target cell, i.e., the cell comprising the receptor to which the antibody or fusion protein binds. The immunoliposomes preferably have an increased half-life in blood, specifically target cells, and can be internalized into the cytoplasm of the target cells thereby avoiding loss of the therapeutic agent or degradation by the endolysosomal pathway.

The immunoliposomal compositions include one or more vesicle forming lipids, an antibody or a fragment or derivative thereof or a fusion protein, and, optionally, a hydrophilic polymer. A vesicle forming lipid is preferably a lipid with two hydrocarbon chains, such as acyl chains and a polar head group. Examples of vesicle forming lipids include phospholipids, e.g., phosphatidylcholine, phosphatidylethanolamine, phosphatidic acid, phosphatidylinositol, sphingomyelin, and glycolipids, e.g., cerebrosides, gangliosides. In some embodiments, the immunoliposomal compositions further comprise a hydrophilic polymer, e.g., polyethylene glycol, and ganglioside GM1, which increases the serum half-life of the liposome. Methods of conjugating hydrophilic polymers to liposomes are encompassed within the disclosure. For a review of immunoliposomes and methods of preparing them, see, e.g., U.S. Patent Application Publication No. 2003/0044407; PCT International Publication No. WO 97/38731, Vingerhoeads et al., 1994, Immunomethods, 4: 259-72; Maruyama, 2000, Biol. Pharm. Bull. 23(7): 791-799; Abra et al., 2002, Journal of Liposome Research, 12(1&2): 1-3; Park, 2002, Bioscience Reports, 22(2): 267-281; Bendas et al., 2001 BioDrugs, 14(4): 215-224, J. Thomas August, ed., 1997, Gene Therapy: Advances in Pharmacology, Volume 40, Academic Press, San Diego, Calif., p. 399-435.

The antibodies and antigen binding fragments can be packaged in a hermetically sealed container, such as an ampoule or sachette, indicating the quantity of antibody. In one embodiment, the antibodies are supplied as a dry sterilized lyophilized powder or water free concentrate in a hermetically sealed container and can be reconstituted, e.g., with water or saline to the appropriate concentration for administration to a subject. Preferably, the antibodies or fusion proteins are supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, or at least 75 mg. The lyophilized antibodies or antigen binding fragments should be stored at between 2 and 8 degrees C. in their original container and the antibodies should be administered within 12 hours, preferably within 6 hours, within 5 hours, within 3 hours, or within 1 hour after being reconstituted. In an alternative embodiment, antibodies or fusion proteins are supplied in liquid form in a hermetically sealed container indicating the quantity and concentration of the antibody, fusion protein, or conjugated molecule. Preferably, the liquid form of the antibodies or fusion proteins are supplied in a hermetically sealed container at least 1 mg/ml, more preferably at least 2.5 mg/ml, at least 5 mg/ml, at least 8 mg/ml, at least 10 mg/ml, at least 15 mg/kg, at least 25 mg/ml, at least 50 mg/ml, at least 100 mg/ml, at least 150 mg/ml, at least 200 mg/ml of the antibodies of fusion proteins.

The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems. For antibodies and fusion proteins, the dosage administered to a patient is typically 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies or fragments thereof, or fusion proteins may be reduced by enhancing uptake and tissue penetration of the antibodies or fusion proteins by modifications such as, for example, lipidation.

HPV Protein Antibodies

In certain embodiments, this disclosure relates to antibodies reported herein and HPV protein binding fragments thereof. In certain embodiments, this disclosure relates to vaccine and pharmaceutical compositions comprising antibodies reported herein and HPV protein binding fragments thereof and pharmaceutically acceptable excipients.

In certain embodiments, the antibody or fragment comprises CDR3 region of the of the heavy chain. Xu et al. report that the diversity in the CDR3 region of V(H) is sufficient for most antibody specificities. Immunity. 2000 July; 13(1):37-45. See also D'Angelo et a. which report immunoglobulin heavy-chain complementarity-determining region 3 (HCDR3) is taken as an antibody molecule's most important component in conferring binding activity and specificity. Front Immunol, 2018; 9: 395.

In certain embodiments, this disclosure relates to antibodies or antigen binding fragments comprising six complementarity determining regions (CDRs) or consensus sequences thereof, wherein the CDRs comprise the three light chain CDRs derived from an antibody selected from 21-1E2, 21-1E11, 21-1H3, 22-1B10, 22-E2A2, 22-E2B2, 22-E2B8, 22-E2B9, 22-E2C5, 22-E2C9, 22-E2C11, 22-E2D4, 22-E2E7, 22-E2F7, 22-E2F10, and 22-E2G5, and wherein the CDRs comprise the three heavy chain CDRs derived from an antibody selected from 21-1E2, 21-1E11, 21-1H3, 22-1B10, 22-E2A2, 22-E2B2, 22-E2B8, 22-E2B9, 22-E2C5, 22-E2C9, 22-E2C11, 22-E2D4, 22-E2E7, 22-E2F7, 22-E2F10, and 22-E2G5, and wherein the antibody or antigen binding fragment thereof specifically binds to an epitope of an HPV protein. In certain embodiments, the HPV protein is E2 and/or E6.

The antibodies of the present disclosure may be produced by any method useful for the production of polypeptides, e.g., in vitro synthesis, recombinant DNA production, and the like. Preferably, the antibodies are produced by recombinant DNA technology. The HPV antibodies may be produced using recombinant immunoglobulin expression technology. The recombinant production of immunoglobulin molecules, including humanized antibodies are described in U.S. Pat. No. 4,816,397 (Boss et al.), U.S. Pat. Nos. 6,331,415 and 4,816,567 (both to Cabilly et al.), U.K. patent GB 2,188,638 (Winter et al.), and U.K. patent GB 2,209,757. Techniques for the recombinant expression of immunoglobulins, including humanized immunoglobulins, can also be found, in Goeddel et al., Gene Expression Technology Methods in Enzymology Vol. 185 Academic Press (1991), and Borreback, Antibody Engineering, W. H. Freeman (1992). Additional information concerning the generation, design and expression of recombinant antibodies can be found in Mayforth, Designing Antibodies, Academic Press, San Diego (1993).

Host cells may be co-transfected with such expression vectors, which may contain different selectable markers but, with the exception of the heavy and light chain coding sequences, are preferably identical. This procedure provides for equal expression of heavy and light chain polypeptides. Alternatively, a single vector may be used which encodes both heavy and light chain polypeptides. The coding sequences for the heavy and light chains may comprise cDNA or genomic DNA or both. The host cell used to express the recombinant HPV antibody can be either a bacterial cell such as *Escherichia coli*, or more preferably a eukaryotic cell (e.g., a Chinese hamster ovary (CHO) cell or a HEK-293 cell). The choice of expression vector is dependent upon the choice of host cell and may be selected so as to have the desired expression and regulatory characteristics in the selected host cell. Other cell lines that may be used include, but are not limited to, CHO-K1, NSO, and PER.C6 (Crucell, Leiden, Netherlands).

Any of the antibodies disclosed herein can be used to generate anti-idiotype antibodies (see, e.g., Greenspan, N. S. et al. (1989) "Idiotypes: Structure and Immunogenicity," FASEB J. 7:437-444; and Nisinoff, A. (1991) "Idiotypes: Concepts and Applications," J. Immunol. 147(8):2429-2438).

Phage display technology can be used to increase the affinity of an antibody for HPV. This technique would be useful in obtaining high affinity antibodies that could be used in the disclosed combinatorial methods. This technology, referred to as affinity maturation, employs mutagenesis or CDR walking and re-selection using such receptors or ligands (or their extracellular domains) or an antigenic fragment thereof to identify antibodies that bind with higher affinity to the antigen when compared with the initial or parental antibody (See, e.g., Glaser, S. M. et al. (1992) "Antibody Engineering by Codon-Based Mutagenesis in a Filamentous Phage Vector System," J. Immunol. 149:3903-3913). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased binding affinity for the antigen can be screened by contacting the immobilized mutants with labeled antigen.

The disclosure contemplates the use of random mutagenesis to identify improved CDRs. Phage display technology can alternatively be used to increase (or decrease) CDR affinity. This technology, referred to as affinity maturation, employs mutagenesis or "CDR walking" and re-selection uses the target antigen or an antigenic fragment thereof to identify antibodies having CDRs that bind with higher (or lower) affinity to the antigen when compared with the initial or parental antibody (see, e.g., Glaser, S. M. et al. (1992) "Antibody Engineering By Codon-Based Mutagenesis In A Filamentous Phage Vector System," J. Immunol. 149:3903-3913). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased (or decreased) binding affinity for the antigen can be screened by contacting the immobilized mutants with labeled antigen.

In certain embodiments, the antibody, antigen binding fragment, the light chain, or the heavy chain comprises a non-naturally occurring chimeric amino acid sequence such that there is at least one mutation that is not present in naturally occurring antibodies comprising the six CDRs.

In certain embodiments, the antibody, antigen binding fragment, or heavy chain, comprises a human constant domain from an immunoglobulin constant region (Fc) having one, two, three, four, five, six, or more of the following mutations G236A, S239D, A330L, I332E, S267E, L328F, P238D, H268F, S324T, S228P, G236R, L328R, L234A, L235A, M252Y, S254T, T256E, M428L, N434S. With regard to IgG-1 Fc mutations reported herein the sequences are in reference to following amino acid sequence starting at amino acid 119:

(SEQ ID NO: 179)
STKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTCV

VVDVSHEDPEVKFNWYVDGVEVHNAKTKPREEQYNSTYRVVSVLTVLH

QDWLNGKEYKCKVSNKALPAPIEKTISKAKGQPREPQVYTLPPSRDEL

TKNQVSLTCLVKGFYPSDIAVEWESNGQPENNYKTTPPVLDSDGSFFL

YSKLTVDKSRWQQGNVFSCSVMHEALHNHYTQKSLSLSPG.

In certain embodiments, this disclosure relates to antibodies reported wherein the constant region comprises a mutation that activates immune responses such as those selected from the constant region comprises as least one, two, three, or more mutations in the Fc domain selected from S239D, I332E, G236A, A330L, or combinations thereof.

FcgRIIb has immunosuppressive function. In certain embodiments, this disclosure relates to antibodies reported wherein the constant region comprises a mutation that suppressed immune responses those selected from the constant region comprises as least one, two, three, or more mutations in the Fc domain selected from S267E, L328F, P238D, or combinations thereof.

Antibodies interact with the complement cascade through C1q binding enabling antibodies to activate complement-dependent cytotoxicity (CDC). In certain embodiments, this disclosure relates to antibodies reported wherein the constant region comprises a mutation that effectively active complement-dependent cytotoxicity such as those selected from S267E, H268F, S324T, and combinations thereof.

In certain embodiment interaction with the immune system through Fc receptors may be unnecessary or undesirable, i.e., immune-silent antibodies. In certain embodiments, this disclosure relates to antibodies reported wherein the constant region comprises a mutation that bind the antigen but do not bind to FcgRs such as those selected from S228P, G236R, L328R, L234A, L235A, or combinations thereof.

In certain embodiments, is may be desirable to have antibodies wherein constant region of the Fc has been to increase or decrease antibody half-life. In certain embodiments, this disclosure relates to antibodies reported wherein the constant region comprises a mutation that increases or decreases the antibodies half-life such as those selected from M252Y, S254T, T256E, M428L, N434S or combinations thereof.

The disclosure particularly contemplates the production and use of "derivatives" of any of the above-described antibodies and their antigen-binding fragments. The term "derivative" refers to an antibody or antigen-binding fragment thereof that immunospecifically binds to an antigen but which comprises, one, two, three, four, five or more amino acid substitutions, additions, deletions or modifications relative to a "parental" (or wild-type) molecule. Such amino acid substitutions or additions may introduce naturally occurring (i.e., DNA-encoded) or non-naturally occurring amino acid residues. The term "derivative" encompasses, for example, chimeric or humanized variants of any of antibodies, as well as variants having altered CH1, hinge, CH2, CH3 or CH4 regions, so as to form, for example antibodies, etc., having variant Fc regions that exhibit enhanced or impaired effector or binding characteristics.

The term "derivative" additionally encompasses non-amino acid modifications, for example, amino acids that may be glycosylated (e.g., have altered mannose, 2-N-acetylglucosamine, galactose, fucose, glucose, sialic acid, 5-N-acetylneuraminic acid, 5-glycolneuraminic acid, etc. content), acetylated, pegylated, phosphorylated, amidated, derivatized by protecting/blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In a specific embodiment, the altered carbohydrate modifications enhance antibody mediated effector function relative to the antibody lacking the carbohydrate modification.

In some embodiments, a humanized antibody is a derivative. Such a humanized antibody comprises amino acid residue substitutions, deletions or additions in one or more CDRs. The humanized antibody derivative may have substantially the same binding, better binding, or worse binding when compared to a non-derivative humanized antibody. In specific embodiments, one, two, three, four, or five amino acid residues of the CDR have been substituted, deleted or added (i.e., mutated).

A derivative antibody or antibody fragment may be modified by chemical modifications including, but not limited to, specific chemical cleavage, acetylation, formulation, metabolic synthesis of tunicamycin, etc. In one embodiment, an antibody derivative will possess a similar or identical function as the parental antibody. In another embodiment, an antibody derivative will exhibit an altered activity relative to the parental antibody. For example, a derivative antibody (or fragment thereof) can bind to its epitope more tightly or be more resistant to proteolysis than the parental antibody.

Derivatized antibodies may be used to alter the half-lives (e.g., serum half-lives) of parental antibodies in a mammal, preferably a human. Preferably such alteration will result in a half-life of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the humanized antibodies of the present disclosure or fragments thereof in a mammal, preferably a human, results in a higher serum titer of said antibodies or antibody fragments in the mammal, and thus, reduces the frequency of the administration of said antibodies or antibody fragments and/or reduces the concentration of said antibodies or antibody fragments to be administered. Antibodies or fragments thereof with increased in vivo half-lives can be generated by modifying (e.g., substituting, deleting or adding) amino acid residues identified as involved in the interaction between the Fc domain and the FcRn receptor. The HPV antibodies can be engineered to increase biological half-lives (see, e.g. U.S. Pat. No. 6,277,375). For example, HPV antibodies can be engineered in the Fc-hinge domain to have increased in vivo or serum half-lives.

Antibodies or fragments thereof with increased in vivo half-lives can be generated by attaching to said antibodies or antibody fragments polymer molecules such as high molecular weight polyethylene glycol (PEG). PEG can be attached to said antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

One embodiment encompasses modification of framework residues of the antibodies. Framework residues in the framework regions may be substituted with the corresponding residue from the CDR donor antibody to alter, preferably improve, antigen binding. These framework substitutions are identified by methods, e.g., by modeling of the interactions of the CDR and framework residues to identify framework residues important for antigen binding and sequence comparison to identify unusual framework residues at particular positions. (See, e.g., U.S. Pat. No. 5,585,089; and Riechmann, L. et al. (1988) "Reshaping Human Antibodies for Therapy," Nature 332:323-327).

Yet another embodiment encompasses antibodies (and more preferably, humanized antibodies) and antigen-binding fragments thereof that are recombinantly fused or chemically conjugated (including both covalently and non-covalently conjugations) to a heterologous molecule (i.e., an unrelated molecule). The fusion does not necessarily need to be direct, but may occur through linker sequences.

In one embodiment such heterologous molecules are polypeptides having at least 10, at least 20, at least 30, at least 40, at least 50, at least 60, at least 70, at least 80, at least 90 or at least 100 amino acids. Such heterologous molecules may alternatively be enzymes, hormones, cell surface receptors, drug moieties, such as: toxins (such as abrin, ricin A, *Pseudomonas* exotoxin (i.e., PE-40), diphtheria toxin, ricin, gelonin, or pokeweed antiviral protein), proteins (such as tumor necrosis factor, interferon (e.g., alpha-interferon, beta-interferon), nerve growth factor, platelet derived growth factor, tissue plasminogen activator, or an apoptotic agent (e.g., tumor necrosis factor-alpha, tumor necrosis factor-bet.)), biological response modifiers (such as, for example, a lymphokine (e.g., interleukin-1 ("IL-1"), interleukin-2 ("IL-2"), interleukin-6 ("IL-6")), granulocyte macrophage colony stimulating factor ("GM-CSF"), granulocyte colony stimulating factor ("G-CSF"), or macrophage colony stimulating factor, ("M-CSF")), or growth factors (e.g., growth hormone ("GH"))), cytotoxins (e.g., a cytostatic or cytocidal agent, such as paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof), antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, BiCNU™ (carmustine; BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), or anti-mitotic agents (e.g., vincristine and vinblastine).

In one embodiment, the antibodies or fusion molecules include an Fc portion. The Fc portion of such molecules may be varied by isotype or subclass, may be a chimeric or hybrid, and/or may be modified, for example to improve effector functions, control of half-life, tissue accessibility, augment biophysical characteristics such as stability, and improve efficiency of production (and less costly). In some embodiments, the Fc region is the native IgG1, IgG2, or IgG4 Fc region. In some embodiments, the Fc region is a hybrid, for example a chimeric consisting of IgG2/IgG4 Fc constant regions. Modifications to the Fc region include, but are not limited to, IgG4 modified to prevent binding to Fc gamma receptors and complement, IgG1 modified to improve binding to one or more Fc gamma receptors, IgG1 modified to minimize effector function (amino acid changes), IgG1 with altered/no glycan (typically by changing expression host). The Fc region may include the entire hinge region, or less than the entire hinge region.

In a preferred embodiment, the Fc domain contains amino acid insertions, deletions or substitutions that enhance binding to CD16A. Exemplary variants of human IgG1 Fc domains with reduced binding to CD32B and/or increased binding to CD16A contain F243L, R929P, Y300L, V305I or P296L substitutions. These amino acid substitutions may be present in a human IgG1 Fc domain in any combination. In one embodiment, the human IgG1 Fc domain variant contains a F243L, R929P and Y300L substitution. In another embodiment, the human IgG1 Fc domain variant contains a F243L, R929P, Y300L, V305I and P296L substitution. In another embodiment, the human IgG1 Fc domain variant contains an N297Q substitution, as this mutation abolishes FcR binding.

Substitutions, additions or deletions in the derivatized antibodies may be in the Fc region of the antibody and may thereby serve to modify the binding affinity of the antibody to one or more Fc R. In one particular embodiment, the modification of the Fc region results in an antibody with an altered antibody-mediated effector function, an altered binding to other Fc receptors (e.g., Fc activation receptors), an altered antibody-dependent cell-mediated cytotoxicity (ADCC) activity, an altered C1q binding activity, an altered complement-dependent cytotoxicity activity (CDC), a phagocytic activity, or any combination thereof.

In some embodiments, the disclosure encompasses antibodies whose Fc region will have been modified so that the molecule will exhibit altered Fc receptor (FcR) binding activity, for example to exhibit decreased activity toward activating receptors such as FcgammaRIIA or FcgammaRIIIA, or increased activity toward inhibitory receptors such as FcgammaRIIB. Preferably, such antibodies will exhibit decreased antibody-dependent cell-mediated cytotoxicity (ADCC) or complement dependent cytotoxicity (CDC) activities (relative to a wild-type Fc receptor).

HPV E2-Specific Antibodies

The nucleotide sequence of heavy chain variable region of 22-1B10 is:

```
                                        (SEQ ID NO: 26)
ATGGACTGGACCTGGAGGATCCTCTTCTTGGTGGCAGCAGCAACAGGT

GTCCACTCCCAGGTGCAGCTGGTGCAATCTGGGTCTGAGTTGAGGAAG

CCTGGGGCCTCAGTGACGGTTTCCTGCAAGGCCTCTGGATACACCTTC

AGTAACCATGATATGAGTTGGGTGCGACAGGCCCCTGGACAAGGACTT

GAGTGGATGGGATGGATCAACAGCAACACTGGGAACCCGACATATGCC
```

-continued

CAGGGCTTCACAGGACGGTTTGTCTTCTCCTTGGACACCTCTGTCAGC

ACGGCATATCTGCAGATCAGTAGTCTGAAGTCTGAGGACACTGCCGTC

TATTACTGTGCGAAAGGGGGGGGGATCTGTAGTGGTAGTAGATGTTAT

TCCGGATGGTTTGACAGTTGGGGCAAGGGAACCCTGGTCGCCGTCTCC

TCA.

The amino acid sequence is (SEQ ID NO: 27)
MDWTWRILFLVAAATGVHSQVQLVQSGSELRKPGASVTVSCKASGYTFS

NHDMSWVRQAPGQGLEWMGWINSNTGNPTYAQGFTGRFVFSLDTSVSTA

YLQISSLKSEDTAVYYCAKGGGICSGSRCYSGWFDSWGKGTLVAVSS.

The CDR1 is GYTFSNHD (SEQ ID NO: 28), CDR2 is INSNTGNP (SEQ ID NO: 29), and CDR3 is AKGGG-ICSGSRCYSGWFDS (SEQ ID NO: 30).

The nucleotide sequence of light chain variable region of 22-1B10 is (SEQ ID NO: 31)
ATGGCTTGGACCCCACTCCTCTTCCTCACCCTCCTCCTCCACTGCACAG

GGTCTCTCTCCCAGCTTGTGCTGACTCAATCGCCCTCTGCCTCTGCCTC

CCTGGGAGCCTCGGTCAAACTCACCTGCACTCTGAGCAGTGGGCACAGC

GGCTACGCCATCGCATGGCATCAGCAGCAGCCGGAGAAGGGCCCTCGGT

ACTTGATGAAGCTTAACAGTGATGGCACCCACACCAAGGGGGACGGGAT

CCCTGATCGCTTCTCAGGCTCCAGCTCTGGGGCTGAGCGCTACCTCACC

ATCTCCAGCCTCCAGTCTGAGGATGAGGCTGACTATTACTGTCAGACCT

GGGGCACTGGCATTCAAGTCTTCGGAACTGGGACCAAGGTCACCATCCT

AGGT.

The amino acid sequence is (SEQ ID NO: 32)
MAWTPLLFLTLLLHCTGSLSQLVLTQSPSASASLGASVKLTCTLSSGHS

GYAIAWHQQQPEKGPRYLMKLNSDGTHTKGDGIPDRFSGSSSGAERYLT

ISSLQSEDEADYYCQTWGTGIQVFGTGTKVTILG.

The CDR1 is SGHSGYA (SEQ ID NO: 33), CDR2 is LNSDGTH (SEQ ID NO: 34), and CDR3 is QTWGTGIQV (SEQ ID NO: 35).

The nucleotide sequence of heavy chain variable region of 22-E2A2 is (SEQ ID NO: 175)
ATGGACTGGACCTGGAGGATCCTCTTCTTGGTGGCGGCAGCCACAGGTG

TCCACTCCCAGGTGCAGCTGGTGCAGTCTGGGGCTGAGGTGACGAAGCC

TGGGGCCTCAGTGAAGGTCTCCTGCAAGGCTTCAGGATACACCTTCACC

GAATACTATATGCACTGGGTGCGACAGGCCCCTGGACAAGGCCTTGAGT

GGATGGGACGGATCAACCCTAACAGTGGTGGCACAAAGTATGCACAGAA

ATTTCAGGGCAGGGTCACCATGACTCGGGACACGACCATCAGTACAGTC

TACATGGAGCTGACCAGCGCCCTATCTGACGACACGGCCGTATATTCCT

GTGTGAGGGCCGATAATAATGGTTATACTTACACTTACTGGGGCCAGGG

AACCCTGGTCACCGTCTCTTCA.

The amino acid sequence is (SEQ ID NO: 36)
MDWTWRILFLVAAATGVHSQVQLVQSGAEVTKPGASVKVSCKASGYTFTE

YYMHWVRQAPGQGLEWMGRINPNSGGTKYAQKFQGRVTMTRDTTISTVYM

ELTSALSDDTAVYSCVRADNNGYTYTYWGQGTLVTVSS.

The CDR1 is GYTFTEYY (SEQ ID NO: 37), CDR2 is INPNSGGT (SEQ ID NO: 38), and CDR3 is VRADNNGYTYTY (SEQ ID NO: 39).

The nucleotide sequence of light chain variable region of 22-E2A2 is (SEQ ID NO: 40)
ATGGAAGCCCCAGCTCAGCTTCTCTTCCTCCTGCTACTCTGGCTCCCAGA

TATCACCGGAGAAATTGTGTTGACACAGTCTCCAGCCACCCTGTCTTTGT

CTCCTGGGGAAAGAGCCACCCTCTCCTGTCGGGCCAGTCAGAGTGTTAGC

AGCTACTTAGCCTGGTACCAACAGAAACCTGGCCAGGCTCCCAGGCTCCT

CATTTATGATGCATCTAAGAGGGCCACTGGCATCCCAGCCAGGTTCAGTG

GCAGTGGGTCTGGGACAGACTTCACTCTCACCATCAGCAGCCTAGAGCCT

GAAGATTTTGCAGTTTATTTCTGTCAGCTGCGTAGCAACTGGCCTCCGCA

CGAGAGGGTCACTTTCGGCCCTGGGACCAAAGTGGATTTCAAA.

The amino acid sequence is (SEQ ID NO: 41)
MEAPAQLLFLLLLWLPDITGEIVLTQSPATLSLSPGERATLSCRASQSVS

SYLAWYQQKPGQAPRLLIYDASKRATGIPARFSGSGSGTDFTLTISSLEP

EDFAVYFCQLRSNWPPHERVTFGPGTKVDFK.

The CDR1 is QSVSSY (SEQ ID NO: 42), CDR2 is DASK (SEQ ID NO: 43), and CDR3 is QLRSNWPPHE (SEQ ID NO: 44).

The nucleotide sequence of heavy chain variable region of 22-E2B2 is (SEQ ID NO: 45)
ATGGACTGGACCTGGAGGATCCTCTTCTTGGTGGCAGCAGCCACAGGAGC

CCACTCCCAGGTGCAGCTGGTGCAGTCTGGGACTGAGGTGAAAAAGCCTG

GGGCCTCAGTGAGGGTCTCCTGCAAGGCTTCTGGATACACCTTCACCGAG

TACTATTTGCACTGGGTGCGACAGGCCCCAGGACAAGGCCTTGAGTGGAT

GGGACGGATCAACCCTAACAGTGGCAACACAAACTATGCACAGAAATTTA

ACGGAAGGGTCACCATGACCAGTGATACGTCCGTCAATTTAGCCTATTTG

GAGGTGAGCGGGCTGACATCTGACGACACGGCCATATATTATTGTACGAG

AGACGATAGTGGGGCTTTCGTTTACTGGGGCCAGGGAACCCTGGTCACCG

TCTCTTCA.

The amino acid sequence is (SEQ ID NO: 46)
MDWTWRILFLVAAATGAHSQVQLVQSGTEVKKPGASVRVSCKASGYTFTE

YYLHWVRQAPGQGLEWMGRINPNSGNTNYAQKFNGRVTMTSDTSVNLAYL

EVSGLTSDDTAIYYCTRDDSGAFVYWGQGTLVTVSS.

The CDR1 is GYTFTEYY (SEQ ID NO: 37), the CDR2 is INPNSGNT (SEQ ID NO: 48), and the CDR3 is TRDDSGAFVY (SEQ ID NO: 49).

The nucleotide sequence of light chain variable region of 22-E2B2 is (SEQ ID NO: 50)
ATGGAAGCCCCAGCTCAGCTTCTCTTCCTCCTGCTACTCTGCCTCCCAGT

TTCAGAGACCACCGGAGAGACTGTGTTGACACAGTCTCCAGCCACCCTGT

CTTTGTCTCCAGGAGAAAGAGCCACCCTCTCCTGCAGGTCCAGTCAGGTT

ATCAGCAGCTACTTAGCCTGGTTCCAACAAAAACCTGGCCAGGCTCCCAG

GCTCCTCATCTATGATACATCCAACAGGGCCACTGGCATCCCAGCCAGGT

TCAGTGGCAGTGGGTCTGGGACAGACTTCACTCTCACCATCAGTAGCCTA

GAGCCTGAGGATTTTGCCGTTTATTACTGTCAGCAGCGTACCAACTGGCC

TCCGCGCGAGAAAATCACTTTCGGCCCTGGGACCAAAGTGGATATCAAG.

The amino acid sequence is (SEQ ID NO: 51)
MEAPAQLLFLLLLCLPVSETTGETVLTQSPATLSLSPGERATLSCRSSQV

ISSYLAWFQQKPGQAPRLLIYDTSNRATGIPARFSGSGSGTDFTLTISSL

EPEDFAVYYCQQRTNWPPREKITFGPGTKVDIK.

The CDR1 is QVISSY (SEQ ID NO: 52), CDR2 is DTSN (SEQ ID NO: 53), and CDR3 is QQRTNWPPREKIT (SEQ ID NO: 54).

The nucleotide sequence of heavy chain variable region of 22-E2B8 is (SEQ ID NO: 55)
ATGGTGATCAGGACTGAACAGAGAGAACTCACCATGGAGTTTGGGCTGAA

CTGGCTTTTTCTTGTGGCTATTTTAAAAGGAGTCCAGTGTGAGGCGCAGT

TGTTCCAGTCTGGGGGGGGCTTGGTCCAGCCGGGGGGTCCCTGAGACTC

ACCTGTGCAACCTCTGGCTTCACCTTCACGAATTATGCCCTAAGCTGGGT

CCGCCAGGCTCCAGGGAGGGGGCTGGAGTGGGTCTCTTCTATTACCGATA

ACGCTGATGCCACATACTACGCAGACTCCGTGAGGGGCCGCTTCACCATC

TCCAGAGACAATCCCAAAAACACCCTATATCTGCAGATGGACAGCCTAAC

AGCCCACGACACGGCCATTTATTTCTGTGCGAAACACCACCACAGAGACG

ATGCTTTTGATGTCTGGGGCCAAGGGACAATGATCACCGTCTCTTCA.

The amino acid sequence:

(SEQ ID NO: 56)
MVIRTEQRELTMEFGLNWLFLVAILKGVQCEAQLFQSGGGLVQPGGSLRL

TCATSGFTFTNYALSWVRQAPGRGLEWVSSITDNADATYYADSVRGRFTI

SRDNPKNTLYLQMDSLTAHDTAIYFCAKHEIHRDDAFDVWGQGTMITVS

S.

The CDR1 is GFTFTNYA (SEQ ID NO: 57), CDR2 is ITDNADAT (SEQ ID NO: 58), and CDR3 is AKHHHRD-DAFDV (SEQ ID NO: 59).

The nucleotide sequence of light chain variable region of 22-E2B8 is (SEQ ID NO: 60)
ATGGCTTGGACCCCACTCCTCTTCCTCACCCTCCTCCTCCACTGCACAGG

GTCTCTCTCCCAGCCTGTGGTGACTCAATCGCCCTCTGCCTCTGCCTCCC

TGGGAGCCTCGGTCAGGCTCACCTGCACTCTGAGTAGTGGCCGCACAACC

TTCGCCGTCGCATGGCATCAGCAGCAGCCACAGAAGGCCCCTCGATTCTT

GATGAGAATTTATAATGATGGCAGCCACTTCAAGGGGGCCGGGATTCCTG

ATCGCTTCTCAGGCTCCAGTTCTGGGGCTGAGCGCTACCTCACCATCTCC

AGCCTCCAGTCTGATGATGAGGCTGACTATTACTGTCAGACGTGGGGCAG

TGGCAGTGTAATGTTCGGCGGAGGGACCAAGGTGACCGTCCTAGGT.

The amino acid sequence is (SEQ ID NO: 61)
MAWTPLLFLTLLLHCTGSLSQPVVTQSPSASASLGASVRLTCTLSSGRTT

FAVAWHQQQPQKAPRFLMRIYNDGSHFKGAGIPDRFSGSSSGAERYLTIS

SLQSDDEADYYCQTWGSGSVMFGGGTKVTVLG.

The CDR1 is SGRTTFA (SEQ ID NO: 62), CDR2 is IYNDGSH (SEQ ID NO: 63), and CDR3 is QTWGSGSVM (SEQ ID NO: 64).

The nucleotide sequence of heavy chain variable region of 22-E2B9 is (SEQ ID NO: 65)
ATGGACTGGACCTGGAGGATCCTCTTCTTGGTGGCAGCAGCAACAGGTGT

CCACTCCCAGATGCAGCTGGAACAATCTGGGTCTGAGTTGAAGAAGCCTG

GGGCCTCAGTGAAGGTCTCCTGCAAGGCTTCTGGATACACGTTCACTAGT

TATCCTATGAATTGGGTGCGACAGGCCCCTGGACAAGGACTTGAGTGGAT

GGGATGGATCAACACCAACAACGGGAACCCAACCTATGCCCGGGACTTCA

CAGGACGATTTGTCTTCTCCTTGGACGCCTCTGTCAACACGGCACATCTG

CAGATCACCAGCCTAGAGGCTGAGGACACCGCCGTCTATTACTGTGCGAG

AGCCGGTTTCGAAATATATGGTGATGCGTTCACCTACTACGGGATGGACG

TCTGGGGCCAGGGAACCACGGTCACCGTCTCTTCA.

The amino acid sequence is (SEQ ID NO: 66)
MDWTWRILFLVAAATGVHSQMQLEQSGSELKKPGASVKVSCKASGYTFTS

YPMNWVRQAPGQGLEWMGWINTNNGNPTYARDFTGRFVFSLDASVNTAHL

QITSLEAEDTAVYYCARAGFEIYGDAFTYYGMDVWGQGTTVTVSS.

The CDR1 is GYTFTSYP (SEQ ID NO: 67), CDR2 is INTNNGNP (SEQ ID NO: 68), and CDR3 is ARAG-FEIYGDAFTYYGMDV (SEQ ID NO: 69).

The nucleotide sequence of light chain variable region of 22-E2B9 is (SEQ ID NO: 70)
ATGGCCTGGGCTCTGCTGCTCCTCACCCTCCTCACTCAGGGCACAGGGTC

CTGGGCCCAGTCTGCCCTGACTCAGCCTGCCTCCGTGTCTGGGTCTCCTG

GACAGTTGATCACCATCTCCTGCATTGGATCCACCGGAGACATTGGCGCT

TATAAATTTGTCTCCTGGTACCAACAATACCCCGGGAAGGCCCCCAAGCT

CATGATTTATGAGGTCAGTAATCGGCCCTCAGGAATCTCTAGTCGCTTCT

CTGGCTCCAAGTCTGGCAATACGGCCTCCCTGACCATCTCTGGGCTGCAG

GTGGACGACGAGGCTGATTATTATTGTAGTTCATATAGAGGCAACACTAC

TCTCTTCGGCGGAGGGACCAAGCTGACCGTCCTAGGT.

The amino acid sequence is (SEQ ID NO: 71)
MAWALLLLTLLTQGTGSWAQSALTQPASVSGSPGQLITISCIGSTGDIGA

YKFVSWYQQYPGKAPKLMIYEVSNRPSGISSRFSGSKSGNTASLTISGLQ

VDDEADYYCSSYRGNTTLFGGGTKLTVLG.

The CDR1 is TGDIGAYKF (SEQ ID NO: 72), CDR2 is EVSN (SEQ ID NO: 73), and CDR3 is SSYRGNTTL (SEQ ID NO: 74).

The nucleotide sequence of heavy chain variable region of 22-E2C5 is (SEQ ID NO: 75)
ATGGACTGGACCTGGAGGGTCTTCTGCTTGCTGGCTGTAGCTCCAGGTGC

TCACTCCCAGGTGCAGTTGGTGCAGTCTGGGGCTGAGGTGAAGAAGCCTG

GGGCCTCAGTGAAGGTTTCCTGCAGGACATCTGGATACAGTTTCACTAGG

TACTATATTCACTGGGTGCGACAGTCTCCTGGGCGGGGCTTGAGTGGAT

GGGAATAATCGATCCTAACAATGGTGGCACAACGTCCGCAAAGACCTTGC

TGGGCAAGGTCTCCATGACCAGAGACACGTCCACGAGCACAGCACACCTG

GAGTTGACCAGCCTGGGACCTGAAGACACGGCCGTCTATTATTGTGCTAT

TTTGTACAGTAACGGCTTGGAGGTCTGGGACTACTGGGGCCAGGGCACCC

TGGTCACCGTCTCCTCA.

The amino acid sequence is (SEQ ID NO: 76)
MDWTWRVFCLLAVAPGAHSQVQLVQSGAEVKKPGASVKVSCRTSGYSFTR

YYIHWVRQSPGRGLEWMGIIDPNNGGTTSAKTLLGKVSMTRDTSTSTAHL

ELTSLGPEDTAVYYCAILYSNGLEVWDYWGQGTLVTSS.

The CDR1 is GYSFTRYY (SEQ ID NO: 77), CDR2 is IDPNNGGT (SEQ ID NO: 78), and CDR3 is AILYSNGLEVWDY (SEQ ID NO: 79).

The nucleotide sequence of light chain variable region of 22-E2C5 is (SEQ ID NO: 80)
ATGGCCTGGACCCCTCTCCTGCTCCCCCTCCTCACTTTCTGCACAGTCTC

TGCGGCCTCCCATGAGCTGACACAGCCTCCCTCGGTGTCAGTGTCCCCAG

GACAAACGGCCCAGATCACCTGCTCTGGAGATACTTTGCCAGATAATTAT

GCTTATTGGTACCAGCAGAGGTCAGGCCAGGCCCCTGTACTGGTCGTCTA

TGAGGACAACAAACGACCCTCCGGGATCCCTGAGAGATTCTCTGGCTCCA

GCTCAGGGACAATGGCCACCTTGACTATCAGTGGGGCCCAGGTGGAGGAT

GATGCTGACTACTATTGTTACTCATCAGACAGAAGTAACAACTTCTTCGG

CGGAGGGACCAAGTTGACCGTCCTGAGT.

The amino acid sequence is (SEQ ID NO: 81)
MAWTPLLLPLLTFCTVSAASHELTQPPSVSVSPGQTAQITCSGDTLPDNY

AYWYQQRSGQAPVLVVYEDNKRPSGIPERFSGSSSGTMATLTISGAQVED

DADYYCYSSDRSNNFFGGGTKLTVLS.

The CDR1 is TLPDNY (SEQ ID NO: 82), the CDR2 is EDNK (SEQ ID NO: 83), and the CDR3 is YSSDRSNNF (SEQ ID NO: 84).

The nucleotide sequence of heavy chain variable region of 22-E2C9 is (SEQ ID NO: 85)
ATGGAGTTTGGGCTGAGCTGGCTTTTTCTTGCGGCTATTTTAAAAGGGAT

GCACTGTGAGGTGCAGTTGTTGGAGTCTGGGGGAGGCTTGGTACAGCCGG

GGGGGTCCCTAAGACTCTCCTGTGCAGCCTCTGGATTCGCCTTCAGTAGT

TTTGGCATGAGTTGGGTCCGCCAGGCTCCAGGGAAGGGGCTGGAGTGGGT

CTCAAGTATTAGTGACGGCGGTGTTGACACATACAACGCAGACTCCGTGA

AGGGCCGCTTCACCATCTCCAGAGACAAGTCCAACAGAGTGTATCTGCAA

ATGACCAGCCTGAGAGCCGAGGACACGGCCGTGTATTACTGTGCGAGAAT

TCGACCTAATTATGTCACGGTCAACCGTGTGGGCCTGGACTACTGGGGCC

AGGGAATCCAGGTCACCGTCTCTTCA.

The amino acid sequence is (SEQ ID NO: 86)
MEFGLSWLFLAAILKGMHCEVQLLESGGGLVQPGGSLRLSCAASGFAFSS

FGMSWVRQAPGKGLEWVSSISDGGVDTYNADSVKGRFTISRDKSNRVYLQ

MTSLRAEDTAVYYCARIRPNYVTVNRVGLDYWGQGIQVTSS.

The CDR1 is GFAFSSFG (SEQ ID NO: 87), The CDR2 is ISDGGVD (SEQ ID NO: 88), and the CDR3 is ARIRPNYVTVNRVGLDY (SEQ ID NO: 89).

The nucleotide sequence of light chain variable region of 22-E2C9 is (SEQ ID NO: 90)
ATGAGGCTCCCTGCTCAGCTCCTGGGGCTGCTAATGCTCTGGGTCTCTGG

ATCCAGTGGGGATATTGTGATGACTCAGTCTTCACTCTCCCTGCCCGTCA

CCCCTGGAGAGCCGGCCTCCATCTCCTGCAGGTCTAGTCAGAGCCTCCTG

CATAGTAATGGATACAACTATTTGGATTGGTACCTGCAGAAGCCAGGGCA

GTCTCCACAGCTCCTGATCTATTTGACTTCTTATCGGGCCCCCGGGGTCC

CTGACAGGTTCAGTGGCAGTGGATCAGGCACAGATTTCACACTGAAAATC

AGCAGAGTGGAGGCTGAGGATGTTGGGGTTTATTACTGCATGCAAGCTCT

ACAAAGTCCTCCCACTTTCGGCCCTGGGACCAAAGTGGATATCAAA.

The amino acid sequence is (SEQ ID NO: 91)
MRLPAQLLGLLMLWVSGSSGDIVMTQSSLSLPVTPGEPASISCRSSQSLL

HSNGYNYLDWYLQKPGQSPQLLIYLTSYRAPGVPDRFSGSGSGTDFTLKI

SRVEAEDVGVYYCMQALQSPPTFGPGTKVDIK.

The CDR1 is QSLLHSNGYNY (SEQ ID NO: 92), The CDR2 is LTSY (SEQ ID NO: 93), and CDR3 is MQALQSPPT (SEQ ID NO: 94).

The nucleotide sequence of heavy chain variable region of 22-E2C11 is (SEQ ID NO: 95)
ATGGAGTTTGGGCTGAGCTGGGTTTTCCTCGTTGCTCTTTTAAGAGCTGT

CCAGTGTCAGGTGCAGCTGGAGGAGTCTGGGGGAGGCGTGGTCCAGCCTG

GGAGGTCCCTGAGACTCTCCTGTGCAGCCTCTGGATTCACCTTCAGTAGA

TTTGGCATGCACTGGGTCCGCCAGGCTCCAGGCAGGGGGCTGGAGTGGGT

GGCAGTTATATCAAATGATGGAAATTATAAATATTCTGCTGACTCCGTGA

GGGGCCGATTCACCATCTCCAGAGACAATTCCAGGAACACCCTGTATCTC

CAAATGAACAGCCTGAGAATTGAGGACACGGCTGTGTATTACTGTGCGAA

AGTCATGTATGACTTCGGTCCTTACTACTACTACGGTCTCGACGTCTGGG

GCCAAGGGGCCACGGTCACCGTCTCTTCA.

The amino acid sequence is (SEQ ID NO: 96)
MEFGLSWVFLVALLRAVQCQVQLEESGGGVVQPGRSLRLSCAASGFTFSR

FGMHWVRQAPGRGLEWVAVISNDGNYKYSADSVRGRFTISRDNSRNTLYL

QMNSLRIEDTAVYYCAKVMYDFGPYYYYGLDVWGQGATVTVSS.

The CDR1 is GFTFSRFG (SEQ ID NO: 97), CDR2 is ISNDGNYK (SEQ ID NO: 98), CDR3 is AKV-MYDFGPYYYYGLDV (SEQ ID NO: 99).

The nucleotide sequence of light chain variable region of 22-E2C11 is (SEQ ID NO: 100)
ATGGCCTGGACCGTTCTCCTCCTCGGCCTCCTCTCTCACTGCACAGGCTC

TGTGACCTCCTATGTGCTGACTCAGCCACCCTCGGTGTCAGTGGCCCCAG

GACAGACGGCCAGGATTACCTGTGGGGGAAACAACATTGGAAATAATAGA

ATACACTGGTACCAGCAGAAGCCAGGCCAGGCCCCTGTGCTGGTCGTCTA

TGCCAATATCGACCGGCCCTCAGGGATCCCTGAGCGATTTTCTGGCTCCA

ACTCTGGGAACACGGCCACCCTGACCATCAATAGGGTCGAGGCCGGGGAT

GAGGCCGACTATTACTGTCAGGTGTGGGATAGTGGTAGTGATCATTGGGT

GTTCGGCGGAGGGACCATGCTGACCGTCCTAGGT.

The amino acid sequence is (SEQ ID NO: 101)
MAWTVLLLGLLSHCTGSVTSYVLTQPPSVSVAPGQTARITCGGNNIGNNR

IHWYQQKPGQAPVLVVYANIDRPSGIPERFSGSNSGNTATLTINRVEAGD

EADYYCQVWDSGSDHWVFGGGTMLTVLG.

The CDR1 is NIGNNR (SEQ ID NO: 102), the CDR2 is ANID (SEQ ID NO: 103), and the CDR3 is QVWDSGSDHWV (SEQ ID NO: 104).

The nucleotide sequence of heavy chain variable region of 22-E2D4 is (SEQ ID NO: 105)
ATGGACTGGACCTGGAGGTTCCTCTTTGTGGTGGCAGCAGCTACAGGTGT

CCAGTCCCAGGTCCAGCTGGTGCAGTCTGGGGCTGAGGTGAAGAGGCCTG

GGTCCTCGGTGAAAGTCTCCTGCAAGGCTTCTGGAGACAACTTCAACAAC

TATGCCTTCCACTGGGTGCGCCAGGCCCCTGGACAAGGGCTTGAGTGGAT

GGGGCGGACCATCCCTTTCCTTGGTTTAACAAGCTACTCACCGAATATCC

AGGGCAGAGTCTCCATTTCCGCGGACAAATCCACGGCCACAGCCTTCATG

GAGATGAGCGGCCTGAGGTCTGAGGACACGGCCATGTATTACTGTGCGAG

CAGCATTCGATTGGGGGACTTTTTATATAGAGCCTCTTACTACTACTCCT

CCCCTCTGGACGTCTGGGGCCAAGGGACCACGGTCACCGTCTCCTCA.

The amino acid sequence is (SEQ ID NO: 106)
MDWTWRFLFVVAAATGVQSQVQLVQSGAEVKRPGSSVKVSCKASGDNFNN

YAFHWVRQAPGQGLEWMGRTIPFLGLTSYSPNIQGRVSISADKSTATAFM

EMSGLRSEDTAMYYCASSIRLGDFLYRASYYYSSPLDVWGQGTTVTVSS.

The CDR1 is GDNFNNYA (SEQ ID NO: 107), CDR2 is TIPFLGLT (SEQ ID NO: 108), and CDR3 is ASSIRLGD-FLYRASYYYSSPLDV (SEQ ID NO: 109).

The nucleotide sequence of light chain variable region of 22-E2D4 is (SEQ ID NO: 110)
ATGGAAACCCCAGCGCAGCTTCTCCTCCTCCTGCTACTCTGGCTCCCAGA

TACCACCGGAGAAGTTGTGTTGACGCAGTCTCCAGGCACCCTGTCTTTGT

CTCCAGGGGATAGAGCCACCCTGACCTGCAGGGCCGGTCAGACTATTAGC

AACAGTTACTTAGCCTGGTACCAGCAGAAACCTGGCCAGGCTCCCAGGCT

CCTCATCTCTGGTGTGTCCAGTAGGGCCACTGGCATCCCAGACAGGTTCA

GTGGCAGTGGGTCTGGGACAGACTTCACTCTCACCATCAGCAGACTGGAG

CCTGAAGATTTTGCAGTATATTACTGTCAGCTGTATGGTAACTCACCCTC

TTTCGGCCAAGGGACACGACTGGAGATTAAA.

The amino acid sequence is (SEQ ID NO: 111)
METPAQLLLLLLLWLPDTTGEVVLTQSPGTLSLSPGDRATLTCRAGQTIS

NSYLAWYQQKPGQAPRLLISGVSSRATGIPDRFSGSGSGTDFTLTISRLE

PEDFAVYYCQLYGNSPSFGQGTRLEIK.

The CDR1 is QTISNSY (SEQ ID NO: 112), CDR2 is GVSS (SEQ ID NO: 113), and CDR3 is QLYGNSPS (SEQ ID NO: 114).

The nucleotide sequence of heavy chain variable region of 22-E2E7 is (SEQ ID NO: 115)
ATGGAGTTTGGGCTGAGCTGGGTTTTCCTTGTTGCAATGTTAAAAGGTGT

CCAGTGCGAGGTGCAGGTGGTGGAGTCTGGGGGAGGCTTGGTCCAGCCGG

GGGGGTCCATGAGACTCTCCTGTGCAGCCTCTGGATTCACCGTCAATAGC

AAATTCATGACCTGGGTCCGCCAGGCTCCAGGGACGGGGCTGGAGTGCGT

CTCGATTATTTATAACGATGGTACCACATACTATAAAGACTCCGTGAAGG

GCCGGTTCACCATCTCCAGAGACAATTCCAAGAACACGTTGTATCTTCAA

ATGAACAGGCTGAGACCTGAGGACACGGCTGTCTATTTCTGTGCGAGAAG

GGGATTTTTCGGGGGGAATGAAGCTTTTGATATCTGGGGCCAAGGGACAC

TGGTCACCGTCTCTTCA.

The amino acid sequence is (SEQ ID NO: 116)
MEFGLSWVFLVAMLKGVQCEVQVVESGGGLVQPGGSMRLSCAASGFTVNS

KFMTWVRQAPGTGLECVSIIYNDGTTYYKDSVKGRFTISRDNSKNTLYLQ

MNRLRPEDTAVYFCARRGFFGGNEAFDIWGQGTLVTVSS.

The CDR1 is GFTVNSKF (SEQ ID NO: 117), The CDR2 is IYNDGTT (SEQ ID NO: 118), the CDR3 is ARRGFFGG-NEAFDI (SEQ ID NO: 119).

The nucleotide sequence of light chain variable region of 22-E2E7 is (SEQ ID NO: 120)
ATGGAAACCCCAGCGCAGCTTCTCTTCCTCCTGCTACTCTGGCTCCCAGA

TACTACCGGAGAAATTGTGTTGACGCAGTCTCCAGGCACCCTGTCTTTGT

CTCCAGGGGAAAGAGCCACCCTCTCCTGCAGGGCCGGTCAGAGTGTTAGC

AGCAGCTACTTAGCCTGGTACCAACAGAGACCTGGCCAGCCTCCCAGGCT

CCTCGTCTATGGTACATCCAACAGGGCCACTGGCGTCCCAGACAGATTCA

GTGGCAGCGGGTCTGGGACAGACTCCACTCTCACCATCAGCAGACTGGAG

CCTGAAGATTTTGCAGTCTATTACTGTCACCAGTATAGTAGCTCACTTCC

GACGTTCGGCCCAGGGACCAAGGTGGAAATCAAA.

The amino acid sequence is (SEQ ID NO: 121)
METPAQLLFLLLLWLPDTTGEIVLTQSPGTLSLSPGERATLSCRAGQSVS

SSYLAWYQQRPGQPPRLLVYGTSNRATGVPDRFSGSGSGTDSTLTISRLE

PEDFAVYYCHQYSSSLPTFGPGTKVEIK.

The CDR1 is QSVSSSY (SEQ ID NO: 122), CDR2 is GTSN (SEQ ID NO: 123), and CDR3 is HQYSSSLPT (SEQ ID NO: 124).

The nucleotide sequence of heavy chain variable region of 22-E2F7 is (SEQ ID NO: 125)
ATGGACTGGACCTGGAGGATCCTCTTCTTGGTGGCAGCAGCCACAGGAGC

CCACTCCCAGGTGCAGCTGGTGCAGTCTGGGACTGAGGTGAAAAAGCCTG

GGGCCTCAGTGAGGGTCTCCTGCAAGGCTTCTGGATACAGCTTCACCGAG

TACTATTTGCACTGGGTGCGACAGGCCCCAGGACAAGGCCTTGAGTGGAT

GGGACGGATCAACCCTAAGAGTGGCAACACAAACTATGCACAGAAACTTA

ACGGAAGGGTCACCATGACCAGTGATACGTCCGTCAATGTAGCCTATTTG

GAGGTGAGCGGGCTGACATCTGACGACACGGCCATATATTATTGTACGAG

AGACGATAATGGGGCTTTCGTTTACTGGGGCCAGGGAACCCTGGTCACCG

TCTCCTCA.

The amino acid sequence is (SEQ ID NO: 126)
MDWTWRILFLVAAATGAHSQVQLVQSGTEVKKPGASVRVSCKASGYSFTE

YYLHWVRQAPGQGLEWMGRINPKSGNTNYAQKLNGRVTMTSDTSVNVAYL

EVSGLTSDDTAIYYCTRDDNGAFVYWGQGTLVTVSS.

The CDR1 is GYSFTEYY (SEQ ID NO: 127), CDR2 is INPKSGNT (SEQ ID NO: 128), CDR3 is TRDDNGAFVY (SEQ ID NO: 129).

The nucleotide sequence of light chain variable region of 22-E2F7 is (SEQ ID NO: 130)
ATGGAAGCCCCAGCTCAGCTTCTCTTCCTCCTGCTACTCTGCCTCCCAGT

TTCAGAGACCACCGGAGAGACTGTGTTGACACAGTCTCCAGCCACCCTGT

CTTTGTCTCCAGGAGAAAGAGCCACCCTCTCCTGCAGGTCCAGTCAGGTT

ATCAGCAGCTACTTAGCCTGGTTCCAACAAAAACCTGGCCAGGCTCCCAG

GCTCCTCATCTATGATACATCCAACAGGGCCACTGGCATCCCAGCCAGGT

TCAGTGGCAGTGGGTCTGGGACAGACTTCACTCTCACCATCAGTAGCCTA

GAGCCTGAGGATTTTGCCGTTTATTACTGTCAGCAGCGTATCAACTGGCC

TCCGCGCGAGAAAATCACCTTCGGCCCTGGGACCAAGGTGGATATCAGG.

The amino acid sequence is (SEQ ID NO: 131)
MEAPAQLLFLLLLCLPVSETTGETVLTQSPATLSLSPGERATLSCRSSQV

ISSYLAWFQQKPGQAPRLLIYDTSNRATGIPARFSGSGSGTDFTLTISSL

EPEDFAVYYCQQRINWPPREKITFGPGTKVDIR.

The CDR1 is QVISSY (SEQ ID NO: 52), CDR2 is DTSN (SEQ ID NO: 53), CDR3 is QQRINWPPREKIT (SEQ ID NO: 47).

The nucleotide sequence of heavy chain variable region of 22-E2F10 is (SEQ ID NO: 132)
ATGGACTGGACCTGGAGGGTCTTCTGCTTGCTGGCTGTAGCTCCAGGTGC

TCACTCCCAGGTGCAGATGGTGCAATCTGGGACTGAGGTGAAGAAGCCTG

GGGCCTCAGTGAAGGTTTCCTGCAAGGCGTCTGGATACGACTTCGCCAAA

TACTATATATCCTGGGTGCGACAGGCCCCCGGACAGGGGCTAGAGTGGAT

GGGAATGATCAACCCTCAGAACGGAGTCACAACCTACACACAGAAAGTCC

AGGGCAGGGTCACCCTGACCAGGGACACGTCCACGACCACAGTTTACATG

GAGCTCAGCAGCCTGAGATTTGAGGACACGGCCGTCTATTATTGTAATAT

TCTCTATATCAGTGGTTCGAACGTTTGGGATTATTGGGGCCAGGGAACCC

TGGTCACCGTCTCTTCA.

The amino acid sequence is (SEQ ID NO: 133)
MDWTWRVFCLLAVAPGAHSQVQMVQSGTEVKKPGASVKVSCKASGYDFAK

YYISWVRQAPGQGLEWMGMINPQNGVTTYTQKVQGRVTLTRDTSTTTVYM

ELSSLRFEDTAVYYCNILYISGSNVWDYWGQGTLVTSS.

The CDR1 is GYDFAKYY (SEQ ID NO: 134), CDR2 is INPQNGVT (SEQ ID NO: 135), and CDR3 is NILYISGSNVWDY (SEQ ID NO: 136).

The nucleotide sequence of light chain variable region of 22-E2F10 is (SEQ ID NO: 137)
ATGGCCTGGACCCCTCTCCTGCTCCCCCTCCTCACTTTCTGCACAGTCTC

TGAGGCCTCCTCTGAGCTGACACAGCCACCCTCGGTGTCAGTTTCCCCAG

GACAAACGGCCAGGATCACCTGCTCTGGAGATGTTTTGCCAAAAAAATAT

GCTTATTGGTACCAACAGAAGTCAGGCCAGGCCCCTGTGCTGGTCGTCTA

TGAGGACACCAAACGACCCTCCGGGATCCCTGAGAGATTCTCTGGCTCCA

GCTCAGGGACAATGGCCACCTTGACTATCAGTGGGGCCCAGGTGGGTGAT

GAAGGTGACTACTACTGTTACTCAACAGACAGTAGTGGTAATTTCTTCGG

TGGAGGGACCAAGTTGACCGTCCTAGGT.

The amino acid sequence is (SEQ ID NO: 138)
MAWTPLLLPLLTFCTVSEASSELTQPPSVSVSPGQTARITCSGDVLPKKY

AYWYQQKSGQAPVLVVYEDTKRPSGIPERFSGSSSGTMATLTISGAQVGD

EGDYYCYSTDSSGNFFGGGTKLTVLG.

The CDR1 is VLPKKY (SEQ ID NO: 176), CDR2 is EDTK (SEQ ID NO: 177), and CDR3 is YSTDSSGNF (SEQ ID NO: 178).

The nucleotide sequence of heavy chain variable region of 22-E2G5 is (SEQ ID NO: 139)
ATGGAGTCTGGGCTGAGCTGGGTTTTCCTTGTTGCAATCTTAAAAGGTGT

CCAGTGTGAGGTGCAGGTGGTGGAGTCTGGGGGAGGCTTGGTCCAGCCGG

GGGGGTCCCTGAGACTCTCCTGTGCAGCCTCTGGATTCACCGTCAATAGC

AAATTCATGACCTGGGTCCGCCAGGCTCCAGGGACGGGGCTGGAGTGCGT

CTCGATTATTTATAACGATGGCAGCACATACTATGCAGACTCTGTGAAGG

GCCGGTTCACCATCTCCAGAGACAATTCCAAGAACACGTTGTATCTTCAA

ATGAACAGGCTGCGACCTGAGGACACGGCTGTGTATTTTTGTGCGAGAAG

GGCATTTTTCGGGGGAAATGATGATTTTGATATCTGGGGCCAAGGGACAC

TGGTCACCGTCTCTTCA.

The amino acid sequence is (SEQ ID NO: 140)
MESGLSWVFLVAILKGVQCEVQVVESGGGLVQPGGSLRLSCAASGFTVNS

KFMTWVRQAPGTGLECVSIIYNDGSTYYADSVKGRFTISRDNSKNTLYLQ

MNRLRPEDTAVYFCARRAFFGGNDDFDIWQGTLVTVSS.

The CDR1 is GFTVNSKF (SEQ ID NO: 117), CDR2 is IYNDGST (SEQ ID NO: 141), and CDR3 is ARRAFFGGNDDFDI (SEQ ID NO: 142).

The nucleotide sequence of light chain variable region of 22-E2G5 is (SEQ ID NO: 143)
ATGGAAACCCCAGCGCAGCTTCTCTTCCTCCTGCTACTCTGGCTCCCA

GATACCAGCGGAGAAATTGTGTTGACGCAGTCTCCAGGCACCCTGTCT

TTGTCTCCAGGGGACAGAGCCACCCTCTCCTGCAGGGCCGGTCAGAGT

GTTAGCAGCAGCTTCTTAGCCTGGTACCAACAGAGACCTGGCCAGCCT

CCCAGGCTCCTCATCTATGGTGCATCCAGCAGGGCCACTGACATCCCA

GACAGATTCAGTGGCAGCGGGTCTGGGACAGACTTCACTCTCACCATC

AGCAGACTGGAGCCTGAAGATTTTGCAGTCTATTACTGTCATCAGTAT

AGTAGCTCACTTCCGACGTTCGGCCCAGGGACCAAGGTGGAAATCAAA.

The amino acid sequence is (SEQ ID NO: 144)
METPAQLLFLLLLWLPDTSGEIVLTQSPGTLSLSPGDRATLSCRAGQS

VSSSFLAWYQQRPGQPPRLLIYGASSRATDIPDRFSGSGSGTDFTLTI

SRLEPEDFAVYYCHQYSSSLPTFGPGTKVEIK.

The CDR1 is QSVSSSF (SEQ ID NO: 145), CDR2 is GASS (SEQ ID NO: 146), and CDR3 is HQYSSSLPT (SEQ ID NO: 124).

HPV16 E6-Specific Antibodies

The nucleotide sequence of heavy chain variable region of 21-1E2 is (SEQ ID NO: 147)
ATGGAGTTTGGGCTGAGCTGGCTTTTTCTTGTGGCTATTTTAAAAGGT

GTCCAGTGTGACGTGCAGCTGGCGGAGTCTGGGGGAGGCCTGGTACAA

TCCCGGGGATTCCCGACACTCTCCTGTGCAGCCTCTGGATTCATCTTT

AACAATTATTTCATGAGTTGGGTCCGCCAGACTCCAGGGAAGGGGCTG

GAGTGGGTCTCAGGGATTAGTGCTAATGGTGAGAGGTCGATATACGCA

GACTCCGTGAAGGGCCGGTTCACCATCTCCAGAGACAATTCCAAGAAA

ACAGTGTCTCTCCAAATGAACAGCCTGAGCGCCGAGGACACGGCCATA

TATTACTGTGCGAGAGCGGGCTGTGACAGCACCAGCTGCTATGCCCGA

GTTGGGTGGTTCGGCCCCTGGGGCCAGGGAATCCTGGTCACCGTCTCC

TCA.

The amino acid sequence is (SEQ ID NO: 148)
MEFGLSWLFLVAILKGVQCDVQLAESGGGLVQPGDSLTLSCAASGFIFN

NYFMSWVRQTPGKGLEWVSGISANGERSIYADSVKGRFTISRDNSKKTV

SLQMNSLSAEDTAIYYCARAGCDSTSCYARVGWFGPWGQGILVTVSS.

The CDR1 is GFIFNNYF (SEQ ID NO: 149), CDR2 is ISANGERS (SEQ ID NO: 150), and CDR3 is ARAGCDSTSCYARVGWFGP (SEQ ID NO: 151).

The nucleotide sequence of light chain variable region of 21-1E2 is (SEQ ID NO: 152)
ATGGTGTTGCAGACCCAGGTCTTCATTTCTCTGTTGCTCTGGATCTCTG

GTGCCTACGGGGACGTCGTGATGACCCAGTCTCCAGACTCCCTGGCTGT

GTCTCTGGGCGAGAGGGCCACCCTCAACTGCAAGTCCAGAGAGAGTGTT

TTATACACTACCAACAACAGGAACTACTTAGCTTGGTACCAGCAGAAAC

CCAGGACAGCCTCCTAAGCTCCTCATTTATGGGCATCTACCCGGGAGTC

TGGGGTCCCTGACCGATTCAGCGGCAGCGGGTCTGGGACAGATTTCTCT

ACTCACCATCAGCAGCCTGCAGGCTGAAGATGTGGCAGTTTATTCTGTC

AGCAATATCTTACAACTCCTCCGACGTTCGGCCAGGGGACCAAGGTAGA

AATCAAA.

The amino acid sequence is (SEQ ID NO: 153)
MVLQTQVFISLLLWISGAYGDVVMTQSPDSLAVSLGERATLNCKSRESVL

YTTNNRNYLAWYQQKPGQPPKLLIYWASTRESGVPDRFSGSGSGTDFSLT

ISSLQAEDVAVYYCQQYLTTPPTFGQGTKVEIK.

The CDR1 is ESVLYTTNNRNY (SEQ ID NO: 154), CDR2 is WAST (SEQ ID NO: 155), and CDR3 is QQYLTTPPT (SEQ ID NO: 156).

The nucleotide sequence of heavy chain variable region of 21-1E11 is (SEQ ID NO: 157)
ATGGAGTTTGGGCTGAGCTGGCTTTTTCTTGCGGCTATTTTAAAAGGT

GTCCAGTGTGAGGTGTTGCTGGTGGAGTCTGGGGGAGACTTGGTCCAG

CCGGGGGGGTCCCTGAGACTCTCCTGTGCAGCCTCTGGATTCCCCTTT

AGCAACTTTGCCATGAACTGGGTCCGCCAGGCTCCAGGGAAGGGGCTG

GAGTGGGTCTCAAGTATTAGCGATACTGGTCTTAAAACATATGCTGCA

GACTCCGTGAAGGGCCGGTTCACCATCTCCAGAGACAGTTCCAAGAAC

ACGGTGGATCTGGAAATGAACAGCCTGAGAGTCGAAGACACGGCCGTA

TATTACTGTGCAAAAACGGGCTGTGACAGTAGAAGCTGCTATGCCCGA

ACTGGGTGGTTGGGCACGTGGGGCCAGGGAACCCTGGTCATCGTCTCC

TCA.

The amino acid sequence is (SEQ ID NO: 158)
MEFGLSWLFLAAILKGVQCEVLLVESGGDLVQPGGSLRLSCAASGFPFS

NFAMNWVRQAPGKGLEWVSSISDTGLKTYAADSVKGRFTISRDSSKNTV

DLEMNSLRVEDTAVYYCAKTGCDSRSCYARTGWLGTWGQGTLVIVSS.

The CDR1 is GFPFSNFA (SEQ ID NO: 159), CDR2 is ISDTGLKT (SEQ ID NO: 160), and CDR3 is AKTGCDSRSCYARTGWLGT (SEQ ID NO: 161).

The nucleotide sequence of light chain variable region of 21-1E11 is (SEQ ID NO: 162)
ATGGAAGCCCCAGCTCAGCTTCTCTTCCTCCTGCTACTCTGGCTCCCA

GATATCACCGGAGAAATTGTGTTGACACAGTCTCCAGCCACCCTGTCT

TTGTCTCCTGGGGAAAGAGCCACCCTCTCCTGTCGGGCCAGTCAGAGT

GTTAGCAGCTACTTAGCCTGGTACCAACAGAAACCTGGCCAGGCTCCC

AGGCTCCTCATTTATGATGCATCTAAGAGGGCCACTGGCATCCCAGCC

AGGTTCAGTGGCAGTGGGTCTGGGACAGACTTCACTCTCACCATCAGC

AGCCTAGAGCCTGAAGATTTTGCAGTTTATTTCTGTCAGCTGCGTAGC

AACTGGCCTCCGCACGAGAGGGTCACTTTCGGCCCTGGGACCAAAGTG

GATTTCAAA.

The amino acid sequence is (SEQ ID NO: 163)
MEAPAQLLFLLLLWLPDITGEIVLTQSPATLSLSPGERATLSCRASQS

VSSYLAWYQQKPGQAPRLLIYDASKRATGIPARFSGSGSGTDFTLTIS

SLEPEDFAVYFCQLRSNWPPHERVTFGPGTKVDFK.

The CDR1 is QSVSSY (SEQ ID NO: 42), CDR2 is DASK (SEQ ID NO: 43), and CDR3 is QLRSNWP-PHERVTF (SEQ ID NO: 164).

The nucleotide sequence of heavy chain variable region of 21-1H3 is (SEQ ID NO: 165)
ATGGACTGGACCTGGAGGTTCCTCTTTGTGGTGGCAGCAGCTACAGGTG

TCCAGTCCCAGGTGCAGCTGGTGCAGTCTGGGGCTGAGGTGAAGAAGCC

TGGGTCCTCGGTGAAGGTCTCCTGCAAGGCTTCTGGAGGCACCTTCGCC

AACTCTGGTGTCGCCTGGGTGCGACAGGCCCCTGGACAAGGGCTTGAGT

GGATGGGAGGACTCATCCCTGTCTTTGGTGCAGCTGATTACGCACAGAA

GTTCCGGGGCAGACTCTCGATTACCGCGGACGAATCTTCGACCACAGCC

TTCATGGAGCTCGATAGCCTGAGATCTGACGACACGGCCGTCTATTACT

GTGCGAAAGATCATTTCACCTACAATAAGTACTTTAGTTGGTTCGACCC

CTGGGGCCAGGGAACCCTGGTCATCGTCTCCTCA.

The amino acid sequence is (SEQ ID NO: 166)
MDWTWRFLFVVAAATGVQSQVQLVQSGAEVKKPGSSVKVSCKASGGTFA

NSGVAWVRQAPGQGLEWMGGLIPVFGAADYAQKFRGRLSITADESSTTA

FMELDSLRSDDTAVYYCAKDHFTYNKYFSWFDPWGQGTLVIVSS.

The CDR1 is GGTFANSG (SEQ ID NO: 167), CDR2 is LIPVFGAA (SEQ ID NO: 168), and CDR3 is AKDHFTYNKYFSWFDP (SEQ ID NO: 169).

The nucleotide sequence of light chain variable region of 21-1H3 is (SEQ ID NO: 170)
ATGAGTGTCCCCACCATGGCCTGGATGATGCTTCTCCTCGGACTCCTT

GCTTATGGATCAGGAGTGGATTCTCAGACTGTGGTGACCCAGGAGCCA

TCGTTGTCAGTGTCCCCTGGAGGGACAGTCACTCTCACTTGTGCCTTG

AGCTCTGGCTCAGTCTCGACTAGCTACTACCCCAGCTGGTACCAACAG

ACCCCCGGCCAGGCTCCACGCACGCTCATCTACAGTACAAATCTTCGC

TCTTCTGGGGTCCCTGATCGCTTCTCCGGCTCCATCCTTGGGAACAAA

GCTGCCCTCACCATCACGGGGGCCCAGGCAGATGATGAATGTGATTAT

TATTGTGTACTCTTTATGGGCAGTGGCATTTCGATGTTCGGCGGAGGG

ACCAAGTTGACCGTCCTA.

The amino acid sequence is (SEQ ID NO: 171)
MSVPTMAWMMLLLGLLAYGSGVDSQTVVTQEPSLSVSPGGTVTLTCA

LSSGSVSTSYYPSWYQQTPGQAPRTLIYSTNLRSSGVPDRFSGSILG

NKAALTITGAQADDECDYYCVLFMGSGISMFGGGTKLTVL.

The CDR1 is SGSVSTSYY (SEQ ID NO: 172), the CDR2 is STNL (SEQ ID NO: 173), and the CDR3 is VLFMGSGISM (SEQ ID NO: 174).

Vaccination

In certain embodiments, this disclosure relates to methods of vaccinating for HPV comprising administering an HPV protein or a nucleic acid such as a nucleic acid (DNA or RNA) vaccine encoding the HPV protein to a subject in an effective amount to vaccinate the subject. In certain embodiments, the HPV protein is E2 and/or E6. In certain embodiments, the HPV protein or vector comprising nucleic acid encoding HPV protein is administered in combination with an anti-CTLA4 and/or anti-PD1/PD-L1 antibody, such as an anti-CTLA4 (e.g., ipilimumab, tremelimumab) and/or an anti-PD1/PD-L1 (e.g., nivolumab, pembrolizumab, atezolizumab, avelumab, durvalumab).

In some embodiments, the present disclosure provides compositions and methods for treatment of HPV-related disease comprising administering immunological compositions followed by administration of an adjuvant, such as the toll-like receptor 7 agonist, imiquimod. In certain embodiments, this disclosure contemplates therapeutic HPV nucleic acid (DNA or RNA) vaccine, HPV 16 protein linked to calreticulin (CRT/E7), a heat shock-related chaperone protein.

In certain embodiments, this disclosure relates to methods for generating an immune response against human papillomavirus (HPV)-associated disease in a subject comprising administering systemically to the subject a therapeutically effective amount of a vaccine composition comprising a nucleic acid encoding an HPV protein and administering to the subject an effective amount of a composition comprising an adjuvant to the site of the HPV-related disease or infection in the subject an adjuvant, such as the toll-like receptor 7 agonist, imiquimod. In certain embodiments, the HPV protein is E2 and/or E6. In certain embodiments, the method further comprises administering an anti-CTLA4 and/or anti-PD1/PD-L1 antibody to the subject. In certain embodiments, the nucleic acid (DNA or RNA) plasmid is administered in combination with an anti-CTLA4 and/or anti-PD1/PD-L1 antibody.

In certain embodiments, this disclosure relates to methods of generating an immune response against human papillomavirus (HPV)-associated disease in a subject comprising administering to the subject a composition comprising a DNA plasmid encoding an HPV protein and subsequently administering to the subject an effective amount of a composition comprising an adjuvant to the site of the HPV-related disease or infection in the subject. In certain embodiments, the HPV protein is E2 and/or E6.

Immunotherapy

In some embodiments, the present disclosure concerns the development of immune cells (including cytotoxic T-lymphocytes (CTLs, also referred to as cytotoxic T-cells)) that target an HPV protein that elicits an immune response in an individual. In certain embodiments, the HPV protein is E2 and/or E6. In certain embodiments, this disclosure relates to methods of developing cytotoxic T-cells that target a HPV protein antigen. In certain embodiments, this disclosure relates to methods and compositions for providing therapy to individuals infected with HPV or that have HPV-associated diseases, including cancers, for example. In specific embodiments, the disclosure regards methods and compositions for adoptive cellular immunotherapy that can target HPV-associated, e.g., HPV16-associated, medical conditions (including cancer) and are therapeutic therefor.

In certain embodiments, this disclosure relates to methods of treating or preventing cancer comprising: removing T cells from the blood of a subject; replicating the T cells outside the body providing replicated T cells; exposing the replicated T cells to antigen presenting cells expressing an HPV protein and presenting the HPV protein derived peptides on the cell surface providing HPV protein activated T cells; and administering HPV protein activated T cells to the subject in need thereof. In certain embodiments, the HPV protein is E2 and/or E6. In certain embodiments, the HPV protein activated T cells are administered in combination with IL-2. In certain embodiments, the HPV protein activated T cells are administered in combination with an anti-CTLA4 and/or anti-PD1/PD-L1 antibody. In certain embodiments, the HPV protein is E2 and/or E6.

In certain embodiments, this disclosure relates to methods of treating or preventing cancer comprising: removing T cells from the blood of a subject; replicating the T cells outside the body providing replicated T cells; exposing the replicated T cells to a vector for expressing an a chimeric antigen receptor on the surface of the cells, wherein the chimeric antigen receptor binds to a HPV protein providing HPV protein targeted T-cells; and administering the HPV protein targeted T cells to the subject in need thereof. In certain embodiments, the HPV protein is E2 and/or E6. In certain embodiments, the HPV protein targeted T cells are administered in combination with IL-2. In certain embodiments, the HPV protein targeted T cells are administered in combination with an anti-CTLA4 or anti-PD1/PD-L1 antibody.

In specific embodiments of part of the method, HPV protein peptides, e.g., HPV16 protein peptides are loaded onto antigen-presenting cells (APCs). The antigenic peptides may be provided to the antigen-presenting cells in a library of peptide mixtures, which may be referred to as pepmixes. In certain aspects of the disclosure, there is pooling of a variety of pepmixes for exposure to the APCs. APCs that present HPV protein derived peptides may be exposed to peripheral blood T cells under certain conditions to result in stimulation of T cells specific for HPV. In certain embodiments, the HPV protein is E2 and/or E6.

In certain embodiments, the present disclosure concerns the generation and/or expansion of HPV protein specific T cells. In certain embodiments, the HPV protein is E2 and/or E6. In certain embodiments, this disclosure relates to methods for stimulating peripheral blood cells, preferably peripheral blood T cells, wherein the method comprises stimulating peripheral blood T cells with antigen presenting cells in the presence of interleukin (IL)-2, IL-4, IL-4, IL-6, IL-7, IL-12, IL-15, and/or IL-18 and wherein the antigen presenting cells are currently or were previously exposed a HPV protein or HPV derived peptide. In certain embodiments, the HPV protein is E2 and/or E6.

In certain embodiments, the present disclosure concerns methods of producing therapeutic T-cells for human papillomavirus (HPV)-associated disease(s), the method comprising the step of stimulating peripheral blood T-cells with antigen presenting cells in the presence of one or more of (IL)-2, IL-4, IL-6, IL-7, IL-12, IL-15, and/or IL-18 wherein the antigen presenting cells were previously exposed an HPV protein or HPV derived peptide, wherein the stimulating produces T-cells therapeutic for HPV-associated diseases. In certain embodiments, the HPV protein is E2 and/or E6.

In certain embodiments, this disclosure contemplates the use of an HPV protein for immunotherapy. In certain embodiments, the HPV protein is E2 and/or E6. In certain embodiments, this disclosure relates to methods of treating or preventing cancer comprising: removing T cells from the blood of a subject with or without an HPV-related cancer; replicating the T cells outside the body providing replicated T cells; exposing the replicated T cells to cells expressing the HPV protein and presenting the HPV protein derived peptides on the surface of the cell providing HPV protein activated T cells and/or a HPV protein peptide; and administering the HPV protein activated T cells to the subject. In certain embodiments, the HPV protein is E2 and/or E6. In certain embodiments, cells presenting HPV protein derived peptides on the surface of the cell are antigen presenting cells. In certain embodiments, the antigen presenting cells were previously exposed to the HPV protein derived peptide.

In certain embodiments, antigen presenting cells or cells expressing an HPV protein and presenting HPV protein derived peptides on the surface of the cell are dendritic cells. In certain embodiments, the HPV protein is E2 and/or E6. Antigens such as the HPV protein located in peripheral tissues are brought to lymph nodes by migratory DCs, which present the antigens on MHC class II molecules. These antigens can be transferred to resident CD8+ DCs, which then present the antigens on MHC class II molecules, and also cross-present them through the MHC class I pathway. In some embodiments, peripheral blood T cells may be present in a population of peripheral blood mononuclear cells (PBMCs) or are obtained or isolated therefrom. The PBMCs in the population may be non-adherent PBMCs. The antigen presenting cells may be activated T cells, dendritic cells, B-blasts, or PBMCs, for example.

In certain embodiments, exposing the replicated T cells to HPV protein derived peptides or cells expressing an HPV protein providing HPV protein activated T cells is in combination with immunostimulatory agents such as IL-2, IL-4, IL-6, IL-7, IL-12, IL-15, and/or IL-18.

In certain embodiments, the replicated T cells are engineered to express a mutant TGF-beta receptor.

In certain embodiments, the HPV protein activated T cells are administered in combination with an immunotherapy agent. In certain embodiments, the immunotherapy agent is an anti-PD-1, anti-CTLA4 antibody or combinations thereof, such as an anti-CTLA4 (e.g., ipilimumab, tremelimumab) and anti-PD1/PD-L1 (e.g., nivolumab, pembrolizumab, atezolizumab, avelumab, durvalumab). In certain embodiments, the method of administration is in a subject with a lymphodepleted environment. In certain embodiments, lymphodepleting agents (e.g., cyclophosphamide and fludarabine) are administered prior to administering HPV protein activated T cells to the subject.

In certain embodiments, the HPV E2 derived peptide consists of one of the following amino-acid sequences:

```
                                         (SEQ ID NO: 2)
DKILTHYENDSTDLRDHI, (SEQ ID NO: 3)
DLRDHIDYWKH, (SEQ ID NO: 4)
AIYYKAREMGFKHINHQVVPTLA, (SEQ ID NO: 5)
AIYYKAREMGFKHINHQVVPTLAVSKKAL, (SEQ ID NO: 6)
YYKAREMGFKHINHQVVPTLAVSKN, (SEQ ID NO: 7)
INHQVVPTLAVSKNKALQAI, (SEQ ID NO: 8)
INHQVVPTLAVSKNKAL, (SEQ ID NO: 9)
TLAVSKNKALQAIELQLTLETIYNSQYSNEKWTLQDV, (SEQ ID NO: 10)
QLTLETIYNSQYSNEKWTLQDVSLE, (SEQ ID NO: 11)
TLETIYNSQYSNEK, (SEQ ID NO: 12)
TSVFSSNEVSSPEII, (SEQ ID NO: 13)
VFSSNEVSSPEIIRQHLANHPAATHTKAVALGTEET, (SEQ ID NO: 14)
EIIRQHLANHPAATHTKAVALGTEETQTTIQRPRSEP.
```

In certain embodiments, the HPV E6 derived peptide consists of one of the following amino-acid sequences:

```
                                         (SEQ ID NO: 16)
MHQKRTAMFQDPQERPRK, (SEQ ID NO: 17)
LPQLCTELQTTIHDIILEC, (SEQ ID NO: 18)
VYCKQQLLRREVYD, (SEQ ID NO: 19)
FAFRDLCIVYRDGNPYA, (SEQ ID NO: 20)
VCDKCLKFYSKISEYRHY, (SEQ ID NO: 21)
CYSLYGTTLEQQYNK, (SEQ ID NO: 22)
PLCDLLIRCINCQKPL, (SEQ ID NO: 23)
CPEEKQRHLDKKQRF, (SEQ ID NO: 24)
HNIRGRWTGRCMS,
and (SEQ ID NO: 25)
CCRSSRTRRETQL.
```

In certain embodiments, this disclosure relates to methods of treating a cancer in a subject, the method comprising: (1) isolating T cells from a subject; (2) generating or expanding a population of T cells specific for a human papillomavirus (HPV) by a method comprising: (i) stimulating the T-cells with antigen presenting cells in the presence of interleukin such as IL-2, IL-4, IL-6, IL-7, IL-12, IL-15, and/or IL-18, wherein the antigen presenting cells, such as dendritic cells or plasmablast cells, were previously exposed to one or more peptides, wherein the peptides comprise sequence that corresponds to at least part of the sequence of an HPV protein; (ii) stimulating T-cells obtained from (i) with antigen presenting cells in the presence of IL-2, IL-4, IL-6, IL-7, IL-12, IL-15, and/or IL-18, wherein the antigen presenting cells were previously exposed to one or more peptides, wherein the peptides comprise sequence that corresponds to at least part of the sequence of the HPV protein, wherein (ii) is optionally repeated one or more times; and (iii) stimulating T-cells obtained from (ii) with antigen presenting cells in the presence of IL-2, IL-4, IL-6, IL-7, IL-12, IL-15, and/or IL-18 and in the presence of co-stimulatory cells, wherein the antigen presenting cells were previously exposed to one or more peptides, wherein the peptides comprise sequence that corresponds to at least part of the sequence of the HPV protein, wherein (iii) is optionally repeated one or more times, (3) administering the generated or expanded population of T cells to a subject. In certain embodiments, the HPV protein is E2 and/or E6.

In certain embodiments, the disclosure contemplates methods of treating cancer comprising administering T cells comprising a vector configured to express a chimeric antigen receptor that bind an HPV protein, e.g., the cells have been infected with a recombinant virus that has a nucleic acid that codes a chimeric antigen receptor. In certain embodiments, the HPV protein is E2 and/or E6.

In certain embodiments, this disclosure relates to methods of treating or preventing cancer comprising: removing T cells from the blood of a subject; replicating the T cells outside the body providing replicated T cells; exposing the replicated T cells to a vector for expressing an a chimeric antigen receptor on the surface of the cells, wherein the chimeric antigen receptor binds to an HPV protein providing HPV protein targeted T cells; and administering HPV protein targeted T cells to the subject in need thereof. In certain embodiments, the HPV protein targeted T cells are administered in combination with IL-2. In certain embodiments, the HPV protein targeted T cells are administered in combination with an anti-CTLA4 or anti-PD1/PD-L1 antibody. In certain embodiments, the HPV protein is E2 and/or E6.

In certain embodiments, the chimeric antigen receptor comprises cancer targeting sequence to an HPV protein, a transmembrane domain, a T cell costimulatory molecule domain, and a signal-transduction component of a T-cell antigen receptor domain. In certain embodiments, the HPV protein is E2 and/or E6.

In order to improve the ability of immune cells to kill cancerous cells, T cells can be isolated from the blood of a patient and genetically altered to express chimeric antigen receptors (CARs) to specifically target proteins expressed on the surface of cancerous cells and stimulate an immune response. When put back into the patient, the cells attack the cancerous cells. In certain embodiment, this disclosure contemplates using CAR T cells that target the HPV protein antigen. Brentjens et al. report that T cells altered to bind CD19 can induce remissions of cancer in adults with chemotherapy-refractory acute lymphoblastic leukemia. Sci Transl Med, 2013, 5(177):177ra38.

In a typical procedure, T cells are purified and isolated from blood or bone marrow. For example, T cells are collected via apheresis, a process that withdraws blood from the body and removes one or more blood components (such as plasma, platelets or other white blood cells). The remaining blood is then returned back into the body. The cells are exposed to a recombinant vector, such as a lentiviral vector, that infects the cells in a way that a CAR protein is produced to be present in the cell membrane. Before and/or after infecting the isolated cells with the recombinant vector, the cells may be induced to replicate using methods disclosed herein. The genetically modified T cells may be expanded by growing cells in the laboratory until there are sufficient number of them. Optionally, these CAR T cells are frozen. The modified cells are then administered back to the patient. Various T cell subsets, as well as T cell progenitors and other immune cells such as natural killer (NK) cells, can be targeted with a CAR.

In certain embodiments, the targeting sequence in a chimeric antigen receptor refers to any variety of polypeptide sequences capable of selectively binding to an HPV protein. In certain embodiments, the HPV protein is E2 and/or E6. The targeting sequences may be variable binding regions of antibodies, single chain antibodies, and antibody mimetic. In certain embodiments, targeting is achieved via a single-chain variable fragment (scFv) derived from an antibody. The targeting sequence it typically connected to the intracellular domains by a hinge/transmembrane region, commonly derived from CD8 or IgG4. The intracellular domains may contain co-stimulatory domains such as CD80, CD86, 4-1BBL, OX40L and CD70 and/or CD28 linked to the cytoplasmic signaling domain of CD3zeta. See Sadelain et al. The basic principles of chimeric antigen receptor (CAR) design, Cancer Discov. 2013, 3(4): 388-398.

Peripheral blood mononuclear cells (PBMCs) may be isolated by leukapheresis. T cells can be enriched by mononuclear cells elutriation and expanded by addition of anti-CD3/CD28 coated paramagnetic beads for activation of T cells. A lentiviral vector encoding an HPV protein capable of expression on the cells may be added at the time of cell activation. Cells may be expanded, harvested and cryopreserved in infusible medium sometime after the subject has had an allogeneic stem-cell transplantation.

Cells may be obtained by isolation from peripheral blood and optionally purified by fluorescent activated cells sorting e.g., mixing cells with fluorescent antibodies or other fluorescent agents (molecular beacons) and separating the cells by flow cytometry based fluorescent sorting. Another option for cells sorting is to provide magnetic particles that are conjugated to specific binding agents, such as antibodies against a particular antigen on a target cells surface. After mixing with a sample, the antibody bound cells are put through a purification column containing a matrix composed of ferromagnetic spheres. When placed on a magnetic separator, the spheres amplify the magnetic field. The unlabeled cells pass through while the magnetically labeled cells are retained within the column. The flow-through can be collected as the unlabeled cells fraction. After a short washing step, the column is removed from the separator, and the magnetically labeled cells are eluted from the column.

CD3 is expressed on T cells as it is associated with the T cells receptor (TCR). The majority of TCR are made up of alpha beta chains (alpha beta T-cells). Alpha beta T-cells typically become double-positive intermediates (CD4+CD8+) which mature into single-positive (CD4+CD8−) T helper cells or (CD4−CD8+) cytotoxic T cells. T helper cells interact with antigen presenting dendritic cells and B cells. Upon activation with cognate antigen by dendritic cells, antigen-specific CD4 T cells can differentiate to become various types of effector CD4 T cells with specific roles in promoting immune responses. Mature gamma delta T cells are CD4−CD8− double-negative.

T cells may be isolated and separated from a human sample (blood or PBMCs or bone marrow) based on the expression of alpha beta T cells receptor (TCR), gamma delta T cells receptor, CD2, CD3, CD4, CD8, CD4 and CD8, NK1.1, CD4 and CD25 and other combinations based on positive or negative selection.

In certain embodiments, the immune cells are CD8+, CD4+, alpha beta T cells, delta gamma T cells, natural killer cells and/or double-negative alpha beta T cells. Wilhelm et al., report infusion of gamma delta T cells. J Transl Med, 2014, 12: 45. Peripheral blood mononuclear cells (leukapheresis product) were depleted of CD4 and CD8 T-cells using anti-CD4 and anti-CD8 antibodies conjugated to paramagnetic particles. The procedure provides purified gamma delta T cells, NK cells, and double-negative alpha beta T cells.

What is claimed is:

1. A chimeric antibody that specifically binds HPV16 E2 protein wherein the antibody comprises a light chain and a heavy chain, wherein the light chain CDR1 is GYTFTSYP (SEQ ID NO: 67), CDR2 is INTNNGNP (SEQ ID NO: 68), and CDR3 is ARAGFEIYGDAFTYYGMDV (SEQ ID NO: 69); and wherein the heavy chain CDR1 is TGDIGAYKF (SEQ ID NO: 72), CDR2 is EVSN (SEQ ID NO: 73), and CDR3 is SSYRGNTTL (SEQ ID NO: 74).

2. The chimeric antibody of claim 1, wherein the light chain comprises the amino acid sequence of (SEQ ID NO: 71)
   MAWALLLLTLLTQGTGSWAQSALTQPASVSGSPGQLITISCIGSTGDIG

AYKFVSWYQQYPGKAPKLMIYEVSNRPSGISSRFSGSKSGNTASLTISG

LQVDDEADYYCSSYRGNTTLFGGGTKLTVLG.

3. The chimeric antibody of claim 1, wherein the heavy chain comprises the amino acid sequence of (SEQ ID NO: 66)
   MDWTWRILFLVAAATGVHSQMQLEQSGSELKKPGASVKVSCKASGYTFT

SYPMNWVRQAPGQGLEWMGWINTNNGNPTYARDFTGRFVFSLDASVNTA

HLQITSLEAEDTAVYYCARAGFEIYGDAFTYYGMDVWGQGTTVTVSS.

4. The chimeric antibody of claim 1, wherein the heavy chain comprises one or more of the following Fc mutations G236A, S239D, A330L, I332E, S267E, L328F, P238D, H268F, S324T, S228P, G236R, L328R, L234A, L235A, M252Y, S254T, T256E, M428L, and N434S wherein the Fc mutations are in reference to following amino acid sequence starting at amino acid 119:

(SEQ ID NO: 179)
   STKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVE

PKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWL

NGKEYKCKVSNKALPAPIEKTISKAKGQPREPQVYTLPPSRDELTKNQV

SLTCLVKGFYPSDIAVEWESNGQPENNYKTTPPVLDSDGSFFLYSKLTV

DKSRWQQGNVFSCSVMHEALHNHYTQKSLSLSPG.

5. A chimeric antibody that specifically binds HPV16 E2 protein wherein the antibody comprises a light chain and a heavy chain, wherein the light chain CDR1 is SGRTTFA (SEQ ID NO: 62), CDR2 is IYNDGSH (SEQ ID NO: 63), and CDR3 is QTWGSGSVM (SEQ ID NO: 64); and wherein the heavy chain CDR1 is GFTFTNYA (SEQ ID NO: 57), CDR2 is ITDNADAT (SEQ ID NO: 58), and CDR3 is AKHHHRDDAFDV (SEQ ID NO: 59).

6. The chimeric antibody of claim 5, wherein the light chain comprises the amino acid sequence of (SEQ ID NO: 61)
   MAWTPLLFLTLLLHCTGSLSQPVVTQSPSASASLGASVRLTCTLSSGRT

TFAVAWHQQQPQKAPRFLMRIYNDGSHFKGAGIPDRFSGSSSGAERYLT

ISSLQSDDEADYYCQTWGSGSVMFGGGTKVTVLG.

7. The chimeric antibody of claim 5, wherein the heavy chain comprises the amino acid sequence of (SEQ ID NO: 56)
MVIRTEQRELTMEFGLNWLFLVAILKGVQCEAQLFQSGGGLVQPGGSLR

LTCATSGFTFTNYALSWVRQAPGRGLEWVSSITDNADATYYADSVRGRF

TISRDNPKNTLYLQMDSLTAHDTAIYFCAKHHHRDDAFDVWGQGTMITV

SS.

8. The chimeric antibody of claim 5, wherein the heavy chain comprises one or more of the following Fc mutations G236A, S239D, A330L, I332E, S267E, L328F, P238D, H268F, S324T, S228P, G236R, L328R, L234A, L235A, M252Y, S254T, T256E, M428L, and N434S
wherein the Fc mutations are in reference to following amino acid sequence starting at amino acid 119:

(SEQ ID NO: 179)
STKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVE

PKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWL

NGKEYKCKVSNKALPAPIEKTISKAKGQPREPQVYTLPPSRDELTKNQV

SLTCLVKGFYPSDIAVEWESNGQPENNYKTTPPVLDSDGSFFLYSKLTV

DKSRWQQGNVFSCSVMHEALHNHYTQKSLSLSPG.

9. A chimeric antibody that specifically binds HPV16 E2 protein wherein the antibody comprises a light chain and a heavy chain,
wherein the light chain CDR1 is VLPKKY (SEQ ID NO: 176), CDR2 is EDTK (SEQ ID NO: 177), and CDR3 is YSTDSSGNF (SEQ ID NO: 178); and
wherein the heavy chain CDR1 is GYDFAKYY (SEQ ID NO: 134), CDR2 is INPQNGVT (SEQ ID NO: 135), and CDR3 is NILYISGSNVWDY (SEQ ID NO: 136).

10. The chimeric antibody of claim 9, wherein the light chain comprises the amino acid sequence of (SEQ ID NO: 138)
MAWTPLLLPLLTFCTVSEASSELTQPPSVSVSPGQTARITCSGDVLPKK

YAYWYQQKSGQAPVLVVYEDTKRPSGIPERFSGSSSGTMATLTISGAQV

GDEGDYYCYSTDSSGNFFGGGTKLTVLG.

11. The chimeric antibody of claim 9, wherein the heavy chain comprises the amino acid sequence of (SEQ ID NO: 133)
MDWTWRVFCLLAVAPGAHSQVQMVQSGTEVKKPGASVKVSCKASGYDFA

KYYISWVRQAPGQGLEWMGMINPQNGVTTYTQKVQGRVTLTRDTSTTTV

YMELSSLRFEDTAVYYCNILYISGSNVWDYWGQGTLVTVSS.

12. The chimeric antibody of claim 9, wherein the heavy chain comprises one or more of the following Fc mutations G236A, S239D, A330L, I332E, S267E, L328F, P238D, H268F, S324T, S228P, G236R, L328R, L234A, L235A, M252Y, S254T, T256E, M428L, and N434S
wherein the Fc mutations are in reference to following amino acid sequence starting at amino acid 119:

(SEQ ID NO: 179)
STKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVE

PKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWL

NGKEYKCKVSNKALPAPIEKTISKAKGQPREPQVYTLPPSRDELTKNQV

SLTCLVKGFYPSDIAVEWESNGQPENNYKTTPPVLDSDGSFFLYSKLTV

DKSRWQQGNVFSCSVMHEALHNHYTQKSLSLSPG.

\* \* \* \* \*